US 8,569,282 B2

(12) United States Patent
Ben-Zeev et al.

(10) Patent No.: US 8,569,282 B2
(45) Date of Patent: Oct. 29, 2013

(54) CARBOXAMIDE COMPOUNDS AND THEIR USE

(75) Inventors: Efrat Ben-Zeev, K. Motzkin (IL); Dongli Chen, Brighton, MA (US); Merav Fichman, Modi'in (IL); Shomir Ghosh, Brookline, MA (US); Steffi Koerner, Medford, MA (US); Jian Lin, Acton, MA (US); Yael Marantz, Kadima (IL); Rosa E. Melendez, Toronto (CA); Pradyumna Mohanty, Woburn, MA (US); Sharon Shacham, Chestnut Hill, MA (US); Zhaoda Zhang, Andover, MA (US)

(73) Assignee: CytoPathfinder, Inc., Tokyo (JP)

( * ) Notice: Subject to any disclaimer, the term of this patent is extended or adjusted under 35 U.S.C. 154(b) by 165 days.

(21) Appl. No.: 12/747,109

(22) PCT Filed: Dec. 11, 2008

(86) PCT No.: PCT/US2008/086388
§ 371 (c)(1),
(2), (4) Date: Aug. 26, 2010

(87) PCT Pub. No.: WO2009/076512
PCT Pub. Date: Jun. 18, 2009

(65) Prior Publication Data
US 2010/0324035 A1  Dec. 23, 2010

Related U.S. Application Data

(60) Provisional application No. 61/012,819, filed on Dec. 11, 2007, provisional application No. 61/036,675, filed on Mar. 14, 2008.

(51) Int. Cl.
C07D 471/04 (2006.01)
A61K 31/4375 (2006.01)

(52) U.S. Cl.
USPC ... 514/210.18; 514/312; 514/320; 514/230.5; 514/309; 514/403; 514/375; 514/321; 514/253.1; 544/105; 544/364; 546/157; 546/196; 546/141; 548/362.5; 548/221

(58) Field of Classification Search
USPC ......... 514/210.18, 312, 320, 230.5, 309, 403, 514/375, 321, 253.1; 544/105, 364; 546/157, 196, 141; 548/362.5, 221
See application file for complete search history.

(56) References Cited

U.S. PATENT DOCUMENTS

| 3,262,850 A | 7/1966 | Jones et al. |
| 3,383,281 A | 5/1968 | Wolf et al. |
| 3,674,836 A | 7/1972 | Creger |
| 3,692,895 A | 9/1972 | Nelson et al. |
| 3,781,328 A | 12/1973 | Witte et al. |
| 3,803,237 A | 4/1974 | Lednicer et al. |
| 4,058,552 A | 11/1977 | Mieville |
| 4,243,666 A | 1/1981 | Campbell et al. |
| 4,405,644 A | 9/1983 | Kabbe et al. |
| 4,452,813 A | 6/1984 | Fujii et al. |
| 4,598,089 A | 7/1986 | Hadvary et al. |
| 4,716,175 A | 12/1987 | Hoefle et al. |
| 4,847,271 A | 7/1989 | Chabala et al. |
| 4,885,302 A | 12/1989 | George et al. |
| 4,945,096 A | 7/1990 | George et al. |
| 5,011,859 A | 4/1991 | Jarvi et al. |
| 5,015,644 A | 5/1991 | Roth et al. |
| 5,026,554 A | 6/1991 | Bartizal et al. |
| 5,041,432 A | 8/1991 | Gaylor et al. |
| 5,051,534 A | 9/1991 | Angelastro et al. |
| 5,064,856 A | 11/1991 | Garrity et al. |
| 5,064,864 A | 11/1991 | Jarvi et al. |
| 5,084,461 A | 1/1992 | Wannamaker et al. |
| 5,102,915 A | 4/1992 | Angelastro et al. |
| 5,120,729 A | 6/1992 | Chabala et al. |
| 5,227,389 A | 7/1993 | Ask et al. |
| 5,274,143 A | 12/1993 | Ramig et al. |
| 5,278,171 A | 1/1994 | Wannamaker et al. |
| 5,360,805 A | 11/1994 | Ask et al. |
| 5,364,867 A | 11/1994 | DeHaven-Hudkins et al. |
| 5,391,571 A | 2/1995 | Mewshaw et al. |
| 5,420,305 A | 5/1995 | Ramig et al. |

(Continued)

FOREIGN PATENT DOCUMENTS

| DE | 27 08 913 | 9/1977 |
| EP | 0 306 375 | 3/1989 |

(Continued)

OTHER PUBLICATIONS

U.S. Appl. No. 12/445,134, filed Mar. 25, 2010, Carboxamide Compounds and Their Use.
U.S. Appl. No. 12/747,106, filed Aug. 26, 2010, Carboxamide Compounds and Their Use.
Boswell et al., "(1978) [1-[3-(Phenothiazin-10-yl)propyl]-4-piperidinyl] phenylmethanones, a Novel Class of Long-Acting Neuroleptic Agents," *J. Med. Chem.*, 21:136-139.
Bruzzese et al., (1966) "A New Naphthylacetamide Derivative," *J. Med. Chem.*, 9:264.

(Continued)

Primary Examiner — Kahsay Habte
(74) Attorney, Agent, or Firm — Goodwin Procter LLP

(57) ABSTRACT

Chemokine receptor antagonists, in particular, compounds of Formula (I-A) that act as antagonists of the chemokine CCR2 receptor, including pharmaceutical compositions and uses thereof to treat or prevent diseases associated with monocyte accumulation, lymphocyte accumulation or leukocyte accumulation are described herein.

(I-A)

35 Claims, No Drawings

(56) References Cited

U.S. PATENT DOCUMENTS

| | | | |
|---|---|---|---|
| 5,475,109 | A | 12/1995 | Selnick et al. |
| 5,510,379 | A | 4/1996 | Lee et al. |
| 5,512,548 | A | 4/1996 | Kushwaha et al. |
| 5,512,565 | A | 4/1996 | Mewshaw et al. |
| 5,540,917 | A | 7/1996 | Isler et al. |
| 5,576,313 | A | 11/1996 | Fisher et al. |
| 5,580,881 | A | 12/1996 | Binet et al. |
| 5,602,151 | A | 2/1997 | Mewshaw et al. |
| 5,618,830 | A | 4/1997 | Selnick et al. |
| 5,635,510 | A | 6/1997 | Burkholder et al. |
| 5,643,874 | A | 7/1997 | Bremer et al. |
| 5,648,366 | A | 7/1997 | Burkholder et al. |
| 5,688,960 | A | 11/1997 | Shankar |
| 5,696,267 | A | 12/1997 | Reichard et al. |
| 5,756,520 | A | 5/1998 | Ask et al. |
| 5,824,690 | A | 10/1998 | Burkholder et al. |
| 5,861,417 | A | 1/1999 | Burkholder et al. |
| 5,919,795 | A | 7/1999 | Chang et al. |
| 5,942,517 | A | 8/1999 | Nagarathnam et al. |
| 5,977,139 | A | 11/1999 | Burkholder et al. |
| 6,020,347 | A | 2/2000 | DeLaszlo et al. |
| 6,074,661 | A | 6/2000 | Olejnik et al. |
| 6,121,283 | A | 9/2000 | Chang et al. |
| 6,133,291 | A | 10/2000 | Wolin et al. |
| 6,136,827 | A | 10/2000 | Caldwell et al. |
| 6,140,343 | A | 10/2000 | DeNinno et al. |
| 6,228,861 | B1 | 5/2001 | Nagarathnam et al. |
| 6,248,747 | B1 | 6/2001 | Nagarathnam et al. |
| 6,268,369 | B1 | 7/2001 | Nagarathnam et al. |
| 6,303,620 | B1 | 10/2001 | Hansen et al. |
| 6,316,445 | B1 | 11/2001 | Burkholder et al. |
| 6,331,313 | B1 | 12/2001 | Wong et al. |
| 6,369,116 | B1 | 4/2002 | Wong et al. |
| 6,423,710 | B1 | 7/2002 | Martins et al. |
| 6,458,787 | B1 | 10/2002 | Martins et al. |
| 6,573,279 | B1 | 6/2003 | Watanabe et al. |
| 6,608,054 | B2 | 8/2003 | Meade et al. |
| 6,620,438 | B2 | 9/2003 | Pairet et al. |
| 6,696,042 | B2 | 2/2004 | Pairet et al. |
| 6,699,493 | B2 | 3/2004 | Wong |
| 6,727,257 | B1 | 4/2004 | Nagarathnam et al. |
| 6,767,915 | B2 | 7/2004 | Bakshi et al. |
| 6,849,621 | B2 | 2/2005 | Rosenblum et al. |
| 6,890,517 | B2 | 5/2005 | Drechsel et al. |
| 7,105,505 | B2 | 9/2006 | Zeng et al. |
| 7,115,601 | B2 | 10/2006 | Naidu et al. |
| 7,220,735 | B2 | 5/2007 | Ting et al. |
| 7,230,008 | B2 | 6/2007 | Jiao et al. |
| 7,268,133 | B2 | 9/2007 | Griffith et al. |
| 7,276,520 | B2 | 10/2007 | Nargund et al. |
| 7,414,057 | B2 | 8/2008 | Bakshi et al. |
| 7,511,062 | B2 | 3/2009 | Kuang et al. |
| 7,776,315 | B2 | 8/2010 | Pairet et al. |
| 2002/0010186 | A1 | 1/2002 | Wong et al. |
| 2003/0055244 | A1 | 3/2003 | Scarborough et al. |
| 2004/0043983 | A1 | 3/2004 | Li |
| 2004/0198756 | A1 | 10/2004 | Davies et al. |
| 2004/0259887 | A1 | 12/2004 | Dow |
| 2005/0239781 | A1 | 10/2005 | Hepperle et al. |
| 2005/0256159 | A1 | 11/2005 | Barton et al. |
| 2006/0110429 | A1 | 5/2006 | Reiff et al. |
| 2006/0182783 | A1 | 8/2006 | Hughes et al. |
| 2006/0205785 | A1 | 9/2006 | Kelly et al. |
| 2006/0258672 | A1 | 11/2006 | Barbosa et al. |
| 2007/0059336 | A1 | 3/2007 | Hughes et al. |
| 2007/0082932 | A1 | 4/2007 | Jiaang et al. |
| 2008/0070948 | A1 | 3/2008 | Kelly et al. |
| 2010/0184749 | A1 | 7/2010 | Fichman et al. |
| 2010/0210633 | A1 | 8/2010 | Lin et al. |
| 2010/0286136 | A1 | 11/2010 | Jones et al. |
| 2010/0324035 | A1 | 12/2010 | Ben-Zeev et al. |
| 2010/0331298 | A1 | 12/2010 | Ben-Zeev et al. |

FOREIGN PATENT DOCUMENTS

| | | |
|---|---|---|
| EP | 0 395 768 | 11/1990 |
| EP | 0 468 434 | 1/1992 |
| EP | 0 747 379 | 12/1996 |
| EP | 1 186 601 | 3/2002 |
| FR | 2 350 341 | 12/1977 |
| GB | 1123004 | 8/1968 |
| GB | 2021108 A | 11/1979 |
| WO | WO-93/12069 | 6/1993 |
| WO | WO-94/00480 | 1/1994 |
| WO | WO-94/01404 | 1/1994 |
| WO | WO-94/26735 | 11/1994 |
| WO | WO-96/10559 | 4/1996 |
| WO | WO-96/26948 | 9/1996 |
| WO | WO-98/02151 | 1/1998 |
| WO | WO-98/27086 | 6/1998 |
| WO | WO-00/05265 | 2/2000 |
| WO | WO-03/010138 | 2/2003 |
| WO | WO-03/088908 A2 | 10/2003 |
| WO | WO-03103669 A1 | 12/2003 |
| WO | WO-2004/050024 | 6/2004 |
| WO | WO-2004/080976 | 9/2004 |
| WO | WO-2004/082616 | 9/2004 |
| WO | WO-2004/083208 | 9/2004 |
| WO | WO-2004/110453 | 12/2004 |
| WO | WO-2005/030209 | 4/2005 |
| WO | WO-2005/047250 | 5/2005 |
| WO | WO-2005/060665 | 7/2005 |
| WO | WO-2005/105092 | 11/2005 |
| WO | WO-2005/107469 | 11/2005 |
| WO | WO-2005/121090 | 12/2005 |
| WO | WO-2006/015986 | 2/2006 |
| WO | WO-2006/036527 | 4/2006 |
| WO | WO-2006/040329 | 4/2006 |
| WO | WO-2006/042954 | 4/2006 |
| WO | WO-2008/045558 | 4/2008 |
| WO | WO-2008/045564 | 4/2008 |
| WO | WO-2808/145681 | 12/2008 |
| WO | WO-2009/076404 | 6/2009 |
| WO | WO-2009/076572 | 6/2009 |
| WO | WO-2010/129843 | 11/2010 |

OTHER PUBLICATIONS

Collins et al., "(1998) 3-(1-Piperazinyl)-4,5-dihydro-1H-benzo[g]indazoles: High Affinity Ligands for the Human Dopamine D4 Receptor with Improved Selectivity over Ion Channels," *Bioorg. Med. Chem.*, 6:743-753.

Feria, M. et al., (2006) "The CCR2 Receptor as a Therapeutic Target, Expert Opinion on Therapeutic Patents," 16:49-57.

Gueremy, (1980) "3-(4-Piperidinylalkyl)indoles, Selective Inhibitors of Neuronal 5-Hydroxytryptamine Uptake," *J. Med. Chem.*, 23:1306-1310.

Hibert, M. F. et al., (1990) "Conformation-Activity Relationship Study of 5-HT3 Receptor Antagonists and a Definition of a Model for This Receptor Site," *J. Med. Chem.*, 33:1594-1600.

Hirayama, F. et al., (2003) "Design, Synthesis and Biological Activity of YM-60828 Derivatives. Part 2: Potent and Orally-Bioavailable Factor Xa Inhibitors Based on Benzothiadiazine-4-one Template," *Bioorg. Med. Chem.*, 11:367-381.

Honkanen, E. et al., (1983) "Synthesis and Antihypertensive Activity of Some New Quinazoline Derivatives," *J. Med. Chem.*, 26:1433-1438.

Janssens et al., (2005) "Norpiperadine Imidazoazepines as a New Class of Potent, Selective, and Nonsedative H1 Antihistamines," *J. Med. Chem.*, 48:2154-2166.

Li, et al., (1991) "Development of an Enzyme-Linked Immunosorbent Assay for the Herbicide Bentazon," *J. Agric. Food Chem.*, 39:1537-1544.

Luo, Z. et al., (2001) "Fluorous Boc ($^F$Boc) Carbamates: New Amine Protecting Groups for Use in Fluorous Synthesis," *J. Org. Chem.*, 66:4261-4266.

Mabire et al., (2005) "Synthesis, Structure-Activity Relationship, and Receptor Pharmacology of a New Series of Quinoline Derivatives Acting as Selective, Noncompetitive mGlu1 Antagonists," *J. Med. Chem.*, 48:2134-2153.

(56) References Cited

OTHER PUBLICATIONS

Martinez et al., (2000) "Nonnucleoside Human Cytomegalovirus Inhibitors: Synthesis and Antiviral Evaluation of (Chlorophenylmethyl)benzothiadiazene Dioxide Derivatives," *J. Med. Chem.*, 43:3267-3273.

Maynard, G. D. et al., (1997) "Synthesis and SAR of 4-(1 H-Benzimidazole-2-carbonyl) piperidines with Dual Histamine H1 tachykinin NK1 Receptor Antagonist Activity," *Bioorg. Med. Chem. Lett.*, 7:2819-2824.

Nishi, T. et al., (1999) "Combined NK1 and NK2 Tachykinin Receptor Antagonists: Synthesis and Structure-Activity Relationships of Novel Oxazolidine Analogues," *Bioorg. Med. Chem. Lett.*, 9:875-880.

Orjales, A. et al., (2003) "Synthesis and Binding Studies of [(Aryl)(aryloxy)methyl]piperidine Derivatives and Related Compounds as Potential Antidepressant Drugs with High Affinity for Seratonin (5-HT) and Norepinephrine (NE) Transporters," *J. Med. Chem.*, 46:5512-5532.

Sundberg et al., (1972) "The o-Styrylnitrene Route to 2-Substituted Indoles. Pyrolysis of o-Azidostyrenes," *J. Org. Chem.*, 37:719-724.

Tabuchi, S. et al., (2002) "Novel Potent Antagonists of Human Neuropeptide Y Y5 Receptor. Part 1: 2-Oxobenzothiazolin-3-acetic Acid Derivatives," *Bioorg. Med. Chem. Lett.*, 12:1171-1175.

Tait et al., (2005) "2,1,3-Benzothiadiazine Derivatives: Synthesis and Screening Versus PDE4 Enzyme," *Il Farmaco*, 60:653-663.

Tait et al., (2005) "Synthesis, biological evaluation and molecular modelling studies on benzothiadiazine derivatives as PDE4 selective inhibitors," *Bioorg. Med. Chem.*, 13:1393-1402.

Ullrich, T. et al., (2000) "A Practical Synthesis of the Seratonin 5-HT2A Receptor Antagonist MDL 100907, Its Enantiomer and Their 3-Phenolic Derivatives as Precursors for [$^{11}$C]Labeled PET Ligands," *Bioorg. Med. Chem.*, 8:2427-2432.

Villani et al., (1966) "Derivatives of 2-Azabicyclo[2.2.2]octane," *J. Med. Chem.*, 9:264-265.

Watanabe, Y. et al., (1992) "Syntheses and 5-HT2 Antagonist Activity of Bicyclic 1,2,4-Triazol-3(2H)-one and 1,3,5-Triazine-2,4(3H)-Dione Derivatives," *J. Med. Chem.*, 35:189-194.

Wouters et al., (1986) "In Vitro Labeling of Serotonin-S2 Receptors: Synthesis and Binding Characteristics of [3H]-7-Aminoketanserin," *J. Med. Chem.*, 29:1663-1668.

International Search Report and Written Opinion, International Application No. PCT/US2008/086388, mailed on Mar. 4, 2009 (18 pages).

International Search Report and Written Opinion, International Application No. PCT/US2007/021917, mailed on Apr. 17, 2008 (24 pages).

International Preliminary Report on Patentability and Written Opinion mailed on Apr. 23, 2009 for PCT/US2007/021895 (8 pages).

International Search Report and Written Opinion, International Application No. PCT/US2007/021895, mailed on Mar. 20, 2008 (15 pages).

International Preliminary Report on Patentability and Written Opinion mailed on Jun. 24, 2010 for PCT/US2008/086165 (10 pages).

International Search Report and Written Opinion, International Application No. PCT/US2008/086165, mailed on Mar. 2, 2009 (18 pages).

International Preliminary Report on Patentability and Written Opinion mailed on Apr. 23, 2009 for PCT/US2007/021917 (12 pages).

International Preliminary Report on Patentability and Written Opinion mailed on Jun. 15, 2010 for PCT/US2008/086388 (10 pages).

European Search Report for European Application No. EP08858495.8, dated Feb. 18, 2011 (5 pages).

International Search Report and Written Opinion, International Application No. PCT/US2010/33990, mailed on Aug. 6, 2010 (9 pages).

Xia et al. (2008) Synthesis and structure-activity relationship of 7-azaindole piperidine derivatives as CCR2 antagonists, *Bioorg. Med. Chem. Lett.* 18:6468-6470.

CARBOXAMIDE COMPOUNDS AND THEIR USE

RELATED APPLICATIONS

This application is a national stage of International (PCT) Patent Application Serial No. PCT/US2008/086388, filed Dec. 11, 2008, and published under PCT Article 21(2) in English, which claims the benefit of priority to U.S. Provisional Patent Application Ser. No. 61/012,819, filed Dec. 11, 2007, and to U.S. Provisional Patent Application Ser. No. 61/036,675, filed Mar. 14, 2008, the contents of each of which are hereby incorporated by reference in their entirety for all purposes.

FIELD

The invention generally relates to the field of chemokine receptor antagonists, in particular, compounds that act as antagonists of the chemokine CCR2 receptor, including pharmaceutical compositions; and uses thereof to treat or prevent diseases associated with, e.g., monocyte accumulation, lymphocyte accumulation or leukocyte accumulation.

BACKGROUND

Leukocyte migration and transport from blood vessels into diseased tissues appears to be a critical component to the initiation of normal disease-fighting inflammatory responses. This process—leukocyte recruitment—is also related to the onset and progression of life-threatening inflammatory and debilitating autoimmune diseases.

The resulting pathology of these diseases derives from the attack of the body's immune system defenses on normal tissues. Accordingly, preventing and blocking leukocytes recruitment to target tissues in inflammatory and autoimmune disease would be a highly effective approach to therapeutic intervention.

The different classes of leukocyte cells involved in cellular immune responses include monocytes, lymphocytes, neutrophils, eosinophils and basophils. In most cases, lymphocytes are the leukocyte class that initiates, coordinates, and maintains chronic inflammatory responses, and thus are generally the most important class of cells to block from entering inflammatory sites. Lymphocytes attract monocytes to the tissue sites, which, with lymphocytes, are responsible for most of the actual tissue damage that occurs in inflammatory disease. Lymphocyte and/or monocyte infiltration is known to lead to a wide range of chronic, autoimmune diseases, and also organ transplant rejection. These diseases include rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, (e.g., *pemphigus vulgaris, p. foliacious, p. erythematosis*), glomerulonephritides, vasculitides, hepatitis, diabetes, allograft rejection, and graft-versus-host disease.

The process, by which leukocytes leave the bloodstream and accumulate at inflammatory sites and start a disease, has at least three steps which have been described as (1) rolling, (2) activation/firm adhesion and (3) transendothelial migration. The second step is mediated at the molecular level by chemoattractant receptors. Chemoattractant receptors on the surface of leukocytes then bind chemoattractant cytokines which are secreted by cells at the site of damage or infection. Receptor binding activates leukocytes, increases the adhesiveness of the adhesion molecules that mediate transendothelial migration, and promotes directed migration of the cells toward the source of the chemoattractant cytokine.

Chemotactic cytokines (leukocyte chemoattractant/activating factors, also known as chemokines, intercrines and SIS cytokines), are a group of 6-15 kDa inflammatory/immunomodulatory polypeptide factors that are released by a wide variety of cells such as macrophages, monocytes, eosinophils, neutrophiles, fibroblasts, vascular endothelial cells, smooth muscle cells, and mast cells, at inflammatory sites. Chemokines have the ability to stimulate directed cell migration, a process known as chemotaxis. Each chemokine contains four cysteine residues (C) and two internal disulfide bonds. Chemokines can be grouped into two subfamilies, based on whether the two amino terminal cysteine residues are immediately adjacent ("CC") or separated by one amino acid ("CXC"). These differences correlate with the organization of the two subfamilies into separate gene clusters. Within each gene cluster, the chemokines typically show sequence similarities between 25 to 60%. The CXC chemokines such as interleukin-8 (IL-8), neutrophil-activating protein-2 (NAP-2) and melanoma growth stimulatory activity protein (MGSA) are chemotactic primarily for neutrophils and T lymphocytes. The CC chemokines, such as RANTES, MIP-1a, MIP-1p, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. Chemokines that do not fall into either of the major chemokine subfamilies include lymphotactin-1, lymphotactin-2 (both C chemokines), and fractalkine (a CXXXC chemokine).

MCP-1 (also known as MCAF (Macrophage Chemotactic and Activating Factor), or JE) is a CC chemokine produced by monocytes/macrophages, smooth muscle cells, fibroblasts, and vascular endothelial cells. It causes cell migration and cell adhesion of monocytes, memory T lymphocytes, T lymphocytes and natural killer cells, as well as mediating histamine release by basophils. High expression of MCP-1 has been reported in diseases where accumulation of monocyte/macrophage and/or T cells is thought to be important in the initiation or progression of diseases, such as atherosclerosis, rheumatoid arthritis, nephritis, nephropathy, pulmonary fibrosis, pulmonary sarcoidosis, asthma, multiple sclerosis, psoriasis, inflammatory bowel disease, myocarditis, endometriosis, intraperitoneal adhesion, congestive heart failure, chronic liver disease, viral meningitis, Kawasaki disease and sepsis.

Furthermore, anti-MCP-1 antibody has been reported to show an inhibitory effect or a therapeutic effect in animal models of rheumatoid arthritis, multiple sclerosis, nephritis, asthma, atherosclerosis, delayed type hypersensitivity, pulmonary hypertension, and intraperitoneal adhesion. A peptide antagonist of MCP-1, MCP-1 (9-76), has been also reported to inhibit arthritis in the mouse model, as well as studies in MCP-1-deficient mice have shown that MCP-1 is essential for monocyte recruitment in vivo.

The published literature indicates that chemokines such as MCP-1 and MIP-1a attract monocytes and lymphocytes to disease sites and mediate their activation and thus are thought to be intimately involved in the initiation, progression and maintenance of diseases deeply involving monocytes and lymphocytes, such as atherosclerosis, restenosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis. The chemokines bind to specific cell-surface receptors belonging to the family of G protein-coupled seven-transmembrane-domain proteins which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration.

Genes encoding receptors of specific chemokines have been cloned, and it is now known that these receptors are G protein-coupled seven-transmembrane receptors present on various leukocyte populations. So far, at least five CXC chemokine receptors (CXCR1 CXCR5) and eight CC chemokine receptors (CCR1-CCR8) have been identified. For example, IL-8 is a ligand for CXCR1 and CXCR2; MIP-1a is a ligand for CCR1 and CCR5, and MCP-I is a ligand for CCR2A and CCR2B. It has been reported that lung inflammation and granuroma formation are suppressed in CCR1-deficient mice, and that recruitment of macrophages and formation of atherosclerotic lesion decreased in CCR2-deficient mice. See, e.g., Murdoch et al., "Chemokine receptors and their role in inflammation and infectious diseases", *Blood* 95(10):3032-3043 (2000), which is incorporated by reference herein.

CCR2 (also termed CKR-2, MCP-1RA or MC1RB) is predominantly expressed on monocytes and macrophages, and is necessary for macrophage-dependent inflammation (Bruhl et al. 1970). CCR2 is a G protein-coupled receptor (GPCR) which binds with high affinity (Kd of 1 nM) to several members of the MCP family of chemokines (CCL2, CCL7, CCL8, etc.), eliciting a chemotactic signal that results in directed migration of the receptor-bearing cells (Dunzendorfer et al. 2001).

CCR2 is implicated in the pathogenesis of several inflammatory diseases such as rheumatoid arthritis, multiple sclerosis and atherosclerosis (Rodriguez-Frade et al. 2005). The critical role of the CCL2-CCR2 pathway as a modulator of the tissue influx of monocytes was demonstrated in mice deficient in the receptor, CCR2, or the ligand, CCL2, which are phenotypically normal, but show a selective defect in the migration of macrophages to sites of inflammation (Boring et al. 1997; Lu et al. 1998).

It was also recently shown that mRNA levels of CCR2 increase with peak inflammation in rat adjuvant-induced arthritis (AIA), a model for rheumatoid arthritis (Shahrara et al. 2003). Moreover, a small molecule CCR2 antagonist with high affinity for the mouse CCR2 receptor was shown to reduce disease in mice subjected to experimental autoimmune encephalomyelitis, a model of multiple sclerosis, as well as a rat model of inflammatory arthritis (Brodmerkel et al. 2005). See also deBoer, "Perspectives for Cytokine Antagonist therapy in COPD", *Drug Discov. Today*, 10(2): 93-106 (2005), which is incorporated by reference herein. Taken together, these results support the ability to treat chronic inflammatory diseases with chemical antagonists of CCR2.

SUMMARY OF THE INVENTION

Compounds that inhibit the binding of chemokines to their receptors, e.g., chemokine receptor antagonists, are believed to be useful as pharmaceutical agents which inhibit the action of chemokines on their target cells. The identification of compounds that modulate the function of CCR2 represents an excellent drug design approach to the development of pharmacological agents for the treatment of inflammatory conditions and diseases associated with CCR2 activation, such as rheumatoid arthritis, lupus and other inflammatory diseases.

The invention provides chemokine receptor modulators, e.g., antagonists, and their use as medicinal agents. The invention further provides novel compounds and medical methods of treatment of inflammation, and other disorders especially those associated with lymphocyte or monocyte accumulation such as atherosclerosis, rheumatoid arthritis, lupus, graft-versus-host diseases and/or transplant rejection. The invention also provides novel compounds and medical methods of treatment of metabolic syndrome, pain, such as that associated with osteoarthritis or rheumatoid arthritis, Non-Insulin Dependant Type II Diabetes (NIDDM), and obesity, as well as other diseases or conditions disclosed herein.

More particularly, the invention provides compounds of formula I-A:

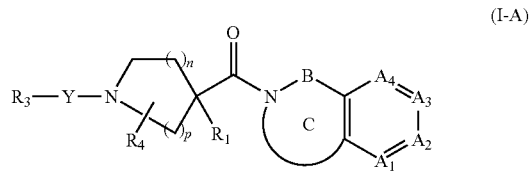

(I-A)

or a pharmaceutically acceptable salt thereof, wherein:

$R_1$ is hydrogen; alkyl, alkoxyalkyl, alkoxyphenyl, alkylthioalkyl, alkylamino, —$SO_2$(alkyl), $C_{3-6}$ cycloalkyl, $C_{3-6}$heterocycloalkyl, aryl, heteroaryl, aralkyl, or heteroaralkyl, each of which is optionally substituted with 1, 2, or 3 $R_5$ substituents; or $R_1$ is optionally substituted ($C_1$-$C_6$alkylene)-$R_{1a}$, wherein $R_{1a}$ is $C_{3-6}$ cycloalkyl, $C_{3-6}$heterocycloalkyl, aryl, or heteroaryl, each of which is optionally substituted with 1, 2, or 3 $R_5$ substituents;

Y is a direct bond or is CO, $SO_2$, —N(H)CO, —N(H)$SO_2$, C(=NH), $C_{1-4}$ alkylene, $C_{2-4}$ alkenylene, $C_{2-4}$ alkynylene, $C_{3-6}$ cycloalkylene, arylene, heterocycloalkylene, heteroarylene, —C(O)alkylene, —N(H)C(O)alkylene, or —O-alkylene; each of which may be optionally substituted with 1, 2, or 3 $R_5$ substituents;

$R_3$ is hydrogen; alkyl, alkenyl, alkynyl, cycloalkyl, aryl, heterocycloalkyl, heteroaryl, or —N($R_6$)($R_7$); each of which may be optionally substituted with 1, 2, or 3 $R_5$ substituents; or $R_3$ is

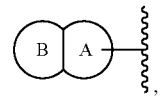

which is an optionally substituted fused aromatic or partially aromatic bicyclic or tricyclic ring containing at least one nitrogen atom;

$R_4$ is hydrogen; halo; $C_{1-8}$ alkyl, alkenyl, or alkynyl optionally interrupted by oxygen or sulfur; cycloalkyl; alkoxy; aralkoxy; or heteroarylalkoxy;

$R_5$, when present, represents independently for each occurrence hydrogen, halo, hydroxy, alkyl, alkenyl, cycloalkyl, alkoxy, —$CO_2$H, —$CO_2C_{1-3}$alkyl, cyano, aryl, heteroaryl, aralkyl, heteroaralkyl, oxo, —$CF_3$, —O—$CF_3$, —O—$CH_2$F, —O—$CHF_2$, —O-aryl, —N(H)alkyl, —N(H)$SO_2$-alkyl, —N(H)C(O)alkyl, —$SO_2$N(H)alkyl, —$SO_2$N(alkyl)C(O)alkyl, or —C(O)N(H)$SO_2$alkyl;

$R_6$ is hydrogen, alkyl, cycloalkyl, heterocycloalkyl, aryl, or heteroaryl;

$R_7$ is hydrogen or $C_{1-3}$ alkyl;

n is 0, 1, 2, or 3;

p is 1 or 2;

$A_1, A_2, A_3$, and $A_4$ are independently N or C—$R_5$, provided that at least two of $A_1$, $A_2$, $A_3$, or $A_4$ are C—$R_5$; and

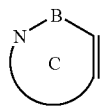

is an optionally substituted 5, 6, or 7-membered mono or bicyclic ring optionally containing a heteroatom selected from O, S, SO, $SO_2$, N—H, N-alkyl, and N—CO-alkyl, in which B is $C_1$-$C_2$alkylene or $C_2$-$C_4$alkenylene, and in which the ring is optionally substituted with 1 or 2 halo, methyl, or ethyl groups, or is geminally substituted to form a cyclopropyl ring.

The invention also provides pharmaceutical compositions comprising a compound of formula I, e.g., formulae I-A, I-A1, I-A2, I-A3, I-A4, I-A5, I-A6, I-A7, I-A8, I-B1, and I-B2, and the use of these compounds and compositions in the prevention or treatment of diseases in which CCR2 chemokine receptors are involved.

The invention additionally provides a method for the treatment of inflammation, pain, rheumatoid arthritis, lupus, systemic lupus erythematosus, atherosclerosis, restenosis, immune disorders, and transplant rejection in a mammal in need thereof, comprising administering to such mammal a therapeutically effective amount of a pharmaceutical composition containing a compound according to formula I in admixture with a pharmaceutically acceptable excipient, diluent, or carrier.

The invention further provides compositions comprising a compound of the invention and a pharmaceutically acceptable carrier.

The invention further provides methods of modulating activity of a chemokine receptor comprising exposing said chemokine receptor to a compound of the invention.

The invention further provides methods of treating a disease associated with expression or activity of a chemokine receptor in a patient comprising administering to the patient a therapeutically effective amount of a compound of the invention.

The invention further provides a compound of Formula I for use in therapy.

The invention further provides use of a compound of Formula I for the manufacture of a medicament for the treatment of disease associated with expression or activity of a chemokine receptor.

The invention further provides use of a compound of the invention for preparing a medicament for treating or preventing inflammation related disorders, including organ transplant rejection, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, glomerulonephritides, vasculitides, hepatitis, allograft rejection, graft-versus-host disease, athersclerosis, metabolic syndrome, diabetes, pain, or obesity.

Also contemplated herein is the use of the disclosed compounds for pain, either pain associated with inflammation, e.g. associated with one of the disorders above, or for any visceral, somatic or neuropathic pain, including chronic pain.

More specifically, the invention provides new anti-inflammatory and immunomodulatory compounds and pharmaceutical compositions thereof that act via antagonism of the CCR2 receptor, therefore leading to MCP-I inhibition. The invention further provides novel compounds for use in the compositions, processes for their preparation, intermediates useful in their preparation, and methods of using the compounds as therapeutic agents.

The chemokine receptor modulators/antagonists of the invention may be effective as therapeutic agents and/or preventive agents for diseases such as atherosclerosis, asthma, pulmonary fibrosis, myocarditis, ulcerative colitis, psoriasis, asthma, ulcerative colitis, nephritis (nephropathy), multiple sclerosis, lupus, systemic lupus erythematosus, hepatitis, pancreatitis, sarcoidosis, organ transplantation, Crohn's disease, endometriosis, congestive heart failure, viral meningitis, cerebral infarction, neuropathy, Kawasaki disease, and sepsis in which tissue infiltration of blood leukocytes, such as monocytes and lymphocytes, play a major role in the initiation, progression or maintenance of the disease.

DETAILED DESCRIPTION

The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified. If a variable is not accompanied by a definition, the previous definition of the variable controls.

DEFINITIONS

For convenience, certain terms used in the specification, examples, and appended claims are collected here.

"CCR2 receptor modulator" or "CCR2 modulator" includes compounds having effect at the CCR2 receptors, including those compounds having a modulating effect primarily at CCR2.

"Treating", includes any effect, e.g., lessening, reducing, modulating, or eliminating, that results in the improvement of the condition, disease, disorder and the like.

The symbol "⌇⌇⌇" indicates a point of attachment.

"Alkyl" includes saturated aliphatic groups, e.g., straight-chain alkyl groups such as methyl, ethyl, propyl, butyl, pentyl, hexyl, heptyl, octyl, nonyl, and decyl; branched-chain alkyl groups (e.g., isopropyl, tert-butyl, and isobutyl); cycloalkyl (alicyclic) groups like cyclopropyl, cyclopentyl, cyclohexyl, cycloheptyl, and cyclooctyl); lower alkyl-substituted cycloalkyl groups; and cycloalkyl-substituted alkyl groups. In an embodiment, alicyclic rings do not include bridged rings. In an embodiment, the alkyl group is substituted.

"Alkyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkyl groups may have six or fewer carbon atoms in their backbone (e.g., $C_1$-$C_6$ for straight chain, $C_3$-$C_6$ for branched chain), and more preferably four or fewer. Preferred cycloalkyl groups have from three to eight carbon atoms in their ring structure, and more preferably five or six carbons in the ring structure. "$C_1$-$C_6$" includes alkyl groups containing one to six carbon atoms.

"Substituted alkyls" refers to alkyl moieties having substituents replacing a hydrogen on one or more carbons of the hydrocarbon backbone. Such substituents can include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, thiocarboxylate, sulfates, alkylsulfinyl, sulfonato, sulfamoyl, sulfonamido, nitro, trifluoromethyl, cyano, azido, or heterocyclyl.

"Alkylene", unless indicated otherwise, means a straight or branched, saturated aliphatic, divalent radical having the number of carbon atoms indicated (e.g., ($C_{1-6}$)alkylene includes methylene (—$CH_2$—), ethylene (—$CH_2CH_2$—), trimethylene (—$CH_2CH_2CH_2$—), and the like. Alkylene may be optionally substituted as provided for alkyl, or as otherwise indicated.

"Alkenylene", unless indicated otherwise, means a straight or branched divalent radical containing a double bond and having the number of carbon atoms indicated; for example, ethylene and propylene. Alkylene may be optionally substituted as provided for alkyl, or as otherwise indicated.

"Alkynylene", unless indicated otherwise, means a straight or branched, unsaturated divalent radical containing a triple bond and having the number of carbon atoms indicated; for example, ethynylene and propynylene. Alkynylene may be optionally substituted as provided for alkyl, or as otherwise indicated.

"Aryl" includes groups with aromaticity, including 5- and 6-membered unconjugated (i.e., single-ring) aromatic groups that may include from zero to four heteroatoms, as well as conjugated (i.e., multicyclic) systems having at least one ring that is aromatic. Examples of aryl groups include benzene, phenyl, tolyl and the like. Multicyclic aryl groups include tricyclic and bicyclic systems, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indolizine, tetralin, and methylenedioxyphenyl.

Aryl groups having heteroatoms in the ring structure may also be referred to as "aryl heterocycles", "heterocycles," "heteroaryls" or "heteroaromatics"; e.g., pyrrole, furan, thiophene, thiazole, isothiazole, imidazole, triazole, tetrazole, pyrazole, oxazole, isooxazole, pyridine, pyrazine, pyridazine, and pyrimidine. The aromatic ring can be substituted at one or more ring positions with, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Arylene", unless indicated otherwise, means an aromatic, divalent radical. The aromatic group includes 5- and 6-membered unconjugated (i.e., single-ring) aromatic moieties that may include from zero to four heteroatoms, as well as conjugated (i.e., multicyclic) systems having at least one ring that is aromatic. Arylene may be optionally substituted as described for aryl, or as otherwise indicated.

"Heteroarylene", unless indicated otherwise, means an heteroaromatic, divalent radical. Heteroarylene may be optionally substituted as described for aryl, or as otherwise indicated.

An "alkylaryl" or an "aralkyl" moiety is an alkyl substituted with an aryl group (e.g., phenylmethyl (benzyl)).

An "alkenylaryl" or an "aralkenyl" moiety is an alkenyl group substituted with an aryl group.

An "alkylheteroaryl" or an "heteroaralkyl" moiety is an alkyl substituted with a heteroaryl group (e.g., phenylmethyl (benzyl)).

An "alkenylheteroaryl" or an "heteroaralkenyl" moiety is an alkenyl group substituted with a heteroaryl group.

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, and decenyl), branched-chain alkenyl groups, cycloalkenyl groups such as cyclopropenyl, cyclopentenyl, cyclohexenyl, cycloheptenyl, and cyclooctenyl; alkyl or alkenyl-substituted cycloalkenyl groups, and cycloalkyl or cycloalkenyl-substituted alkenyl groups.

"Alkenyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkenyl groups may have six or fewer carbon atoms in their backbone (e.g., $C_2$-$C_6$ for straight chain, $C_3$-$C_6$ for branched chain.) Preferred cycloalkenyl groups have from three to eight carbon atoms in their ring structure, and more preferably have five or six carbons in the ring structure. The term "$C_2$-$C_6$" includes alkenyl groups containing two to six carbon atoms.

"Substituted alkenyls" refers to alkenyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups.

"Alkynyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound Straight or branched chain alkynyls group may have six or fewer carbon atoms in their backbone (e.g., $C_2$-$C_6$ for straight chain, $C_3$-$C_6$ for branched chain). The term "$C_2$-$C_6$" includes alkynyl groups containing two to six carbon atoms.

"Substituted alkynyls" refers to alkynyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have corresponding chain lengths, e.g., 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups. "Alkylamino" includes moieties wherein an alkyl moiety is bonded to an amino group; "dialkylamino", "arylamino", "diarylamino", and "alkylarylamino" are analogously named. In some embodiments, "amino" may include acylamino and/or alkylamino groups.

"Alkoxyalkyl" includes moieties where an alkoxy group is bonded to an alkyl group; "alkoxyaryl", "thioalkoxyalkyl", "alkylaminoalkyl" and "alkylthioalkyl" are analogously named.

"Alkoxy" or "alkoxyl" includes alkyl, alkenyl, and alkynyl groups covalently linked to an oxygen atom. Examples of alkoxy or alkoxyl groups include methoxy, ethoxy, isopropyloxy, propoxy, butoxy, and pentoxy groups. In an embodiment, the alkoxy or alkoxyl group is substituted. Examples of substituted alkoxy or substituted alkoxyl groups include halogenated alkoxy groups. Substituted alkoxy groups can include alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl substituents. Examples of halogen-substituted alkoxy groups include fluoromethoxy, difluoromethoxy, trifluoromethoxy, chloromethoxy, dichloromethoxy, and trichloromethoxy.

The terms "heterocycloalkyl", "heterocyclyl" or "heterocyclic group" include closed ring structures, e.g., 3- to 10-, or 4- to 7-membered rings which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like. Heterocyclic groups can have aromatic character such as pyrrole and furan. Heterocyclic groups includes fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like. Heterocycloalkyl, heterocyclyl, or heterocyclic groups include spirocyclic groups.

Heterocyclic rings may be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In an embodiment, heterocyclic rings do not include bridged rings.

The term "heterocycloalkylene," unless indicated otherwise, means the divalent radical of a closed ring structure, e.g., 3- to 10-, or 4- to 7-membered rings which include one or more heteroatoms. Heterocycloalkylene may be optionally substituted as described for heterocyclyl.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —$O^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Contacting" refers to the bringing together of indicated moieties in an in vitro or in vivo system. For example, "contacting" a chemokine receptor with a compound of the invention includes the administration of a compound of the invention to an individual or patient, such as a human, having a chemokine receptor, as well as, for example, introducing a compound of the invention into a sample containing a cellular or purified preparation containing the chemokine receptor.

"Selective" means that a compound binds to or inhibits a chemokine receptor with greater affinity or potency, respectively, compared to at least one other chemokine receptor, or preferably compared to all other chemokine receptors of the same class (e.g., all the CC-type receptors). In some embodiments, the compounds of the invention have binding or inhibition selectivity for CCR2 over any other chemokine receptor. Selectivity can be at least about 10-fold, at least about 20-fold, at least about 50-fold, at least about 100-fold, at least about 200-fold, at least about 500-fold or at least about 1000-fold. Binding affinity and inhibitor potency can be measured according to routine methods in the art.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp. 19-23).

Compounds of the Invention

One aspect of the invention provides chemokine receptor modulators, e.g., antagonists, and their use as medicinal agents, as embodied by a compound of formula I-A.

(I-A)

A specific value for $R_1$ is hydrogen. Another specific value for $R_1$ is alkyl. Other specific values for $R_1$ include alkoxyalkyl, alkoxy-$CHF_2$, alkoxy-$CH_2F$, alkoxy-$CF_3$, $C_{3-6}$ cycloalkyl, $C_{3-6}$ heterocycloalkyl, aryl, heteroaryl, or ($C_1$-$C_6$alkylene)-$R_{1a}$, wherein $R_{1a}$ is $C_{3-6}$ cycloalkyl, $C_{3-6}$ heterocycloalkyl, aryl, or heteroaryl, each of which may be independently optionally substituted with 1, 2, or 3 $R_5$ substituents. Exemplary $R_1$ moieties —$CH_2$—O—$CH_3$, $CH_2$—O—$CF_3$, $CH_2$—O—$CHF_2$, $CH_2$—O—$CH_2F$, —$CH_2$—O—$CH_2$—$CH_3$, —$CH_2$—O—CH—$(CH_3)_2$, or —$CH_2$—CN.

Another specific value for $R_1$ is wherein z is 1, 2, or 3;

y is 1, 2, 3, or 4; and x is O, NH, $CH_2$, $CF_2$, or N($C_{1-8}$alkyl).

Another specific value for $R_1$ is methyl;

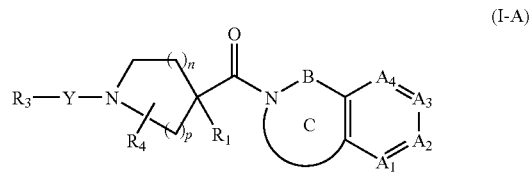

any of which may be optionally substituted on carbon with 1, 2, or 3 $R_5$, and wherein $R_6$ is hydrogen, alkyl, cycloalkyl, heterocycloalkyl, aryl, heteroaryl, or $SO_2R_8$; and $R_8$ is an alkyl, alicyclic, aryl, heterocyclic, or heteroaryl group.

Another specific value for $R_1$ is

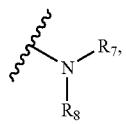

wherein $R_7$ and $R_8$ can be taken together with the nitrogen to which they are attached to form an 3, 4, 5, or 6-membered ring which itself may be optionally substituted with 1, 2, or 3, $R_5$; or $R_7$ is hydrogen, or $C_{1-3}$ alkyl; and $R_8$ is an alkyl, alicyclic, aryl, heterocyclic, or heteroaryl group.

A specific value for Y is $CH_2$. Another specific value for Y is

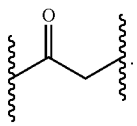 [SMILES: *CC(*)=O ; "."]

Another specific value for Y is

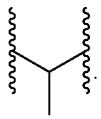 [SMILES: *C(*)C ; "."]

Other specific values for Y include,

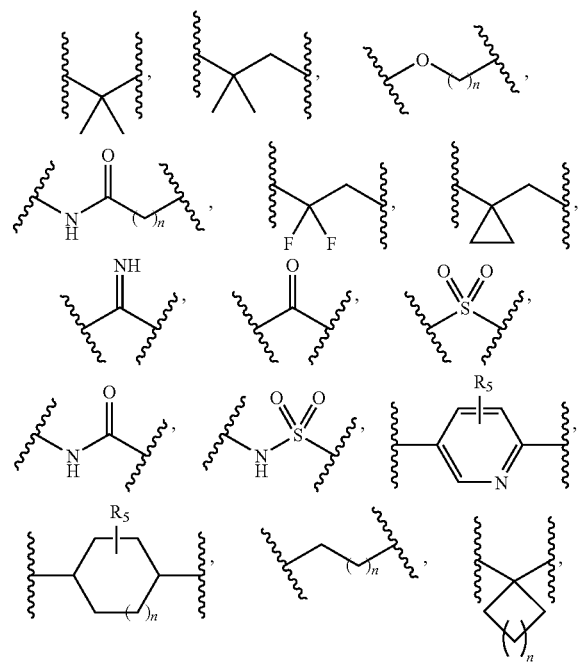

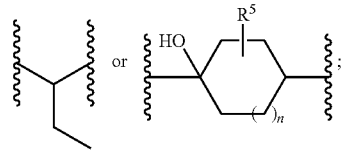

wherein n is 0, 1 or 2.

Specific values for $R_3$ include:

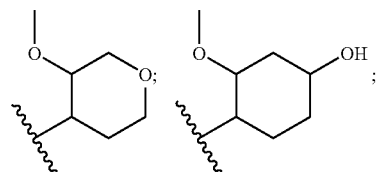

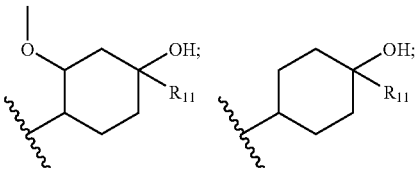

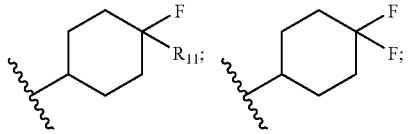

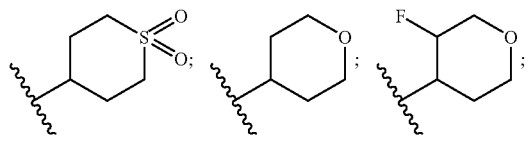

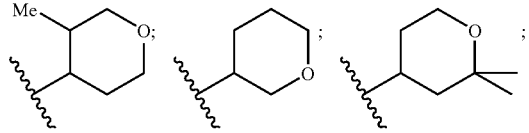

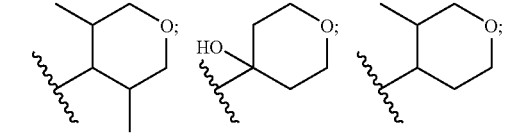

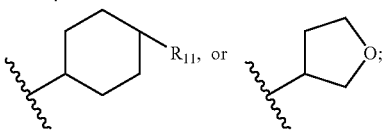

wherein $R_{11}$ is hydrogen or is $C_{1-6}$ alkyl, ($C_1$-$C_6$alkylene) cycloalkyl, aralkyl, or heteroaralkyl, any of which may be optionally substituted with halo, hydroxy, alkyl, alkenyl, cycloalkyl, $C_{1-3}$alkoxy, —$CO_2H$, —$CO_2C_{1-3}$alkyl, cyano, aryl, heteroaryl, —$CF_3$, —O—$CF_3$, —O—$CH_2F$, or —O—$CHF_2$;

Another specific value for $R_3$ is

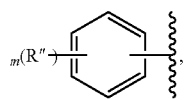

wherein m is 1, 2, or 3; and R" represents independently for each occurrence hydroxyl, halo, alkoxy, halo-alkoxy, $C_{1-3}$ alkyl-S(O)$_2$—NH—, —CO$_2$H, $C_{1-3}$ alkyl-C(O)—NH—, alkyl-SO$_2$NHCO—, aryl, halo-substituted aryl, or heteroaryl; or wherein two R" attached to adjacent carbon atoms are taken together to form
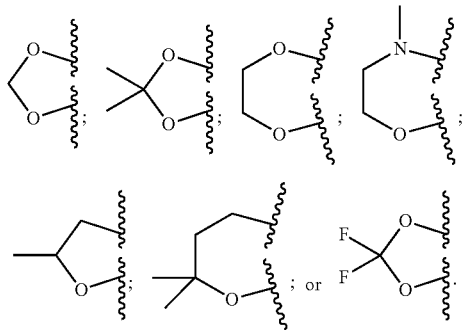
Other specific values for $R_3$ include
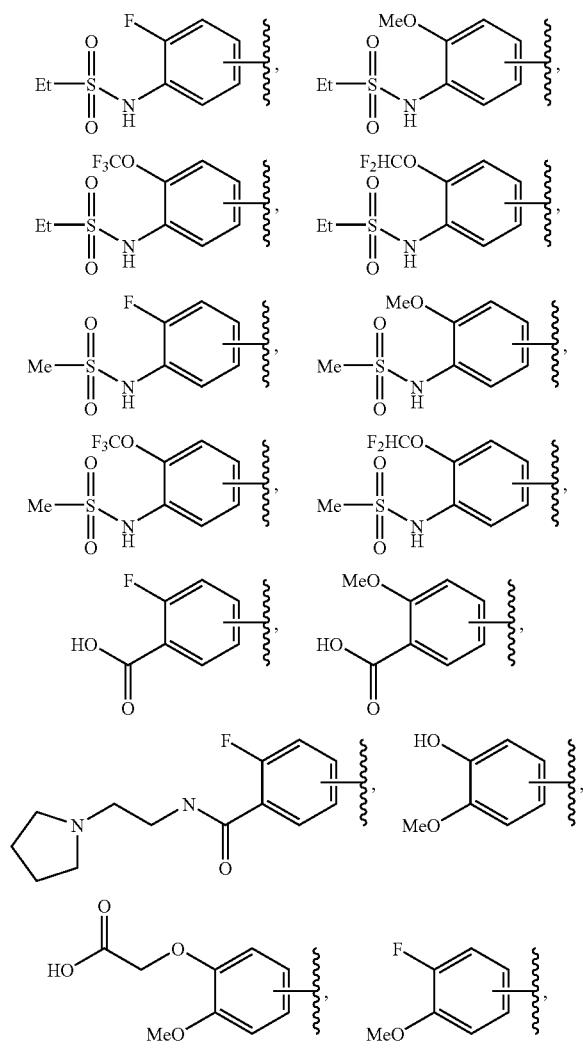
-continued
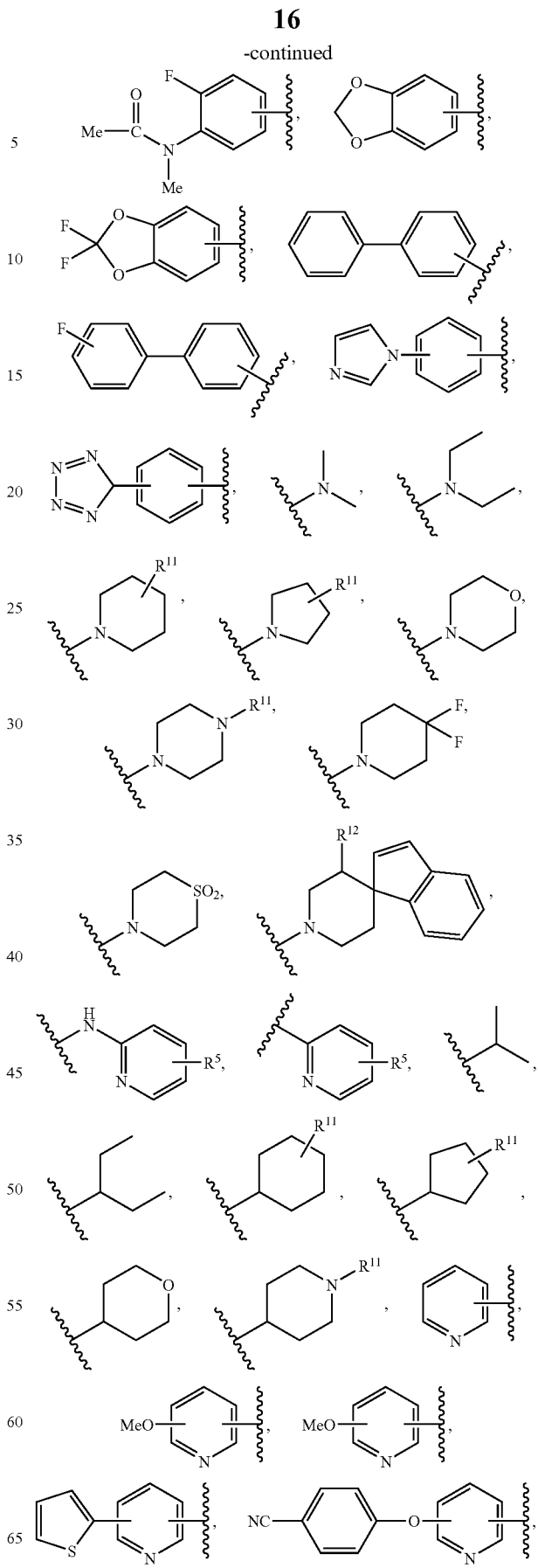

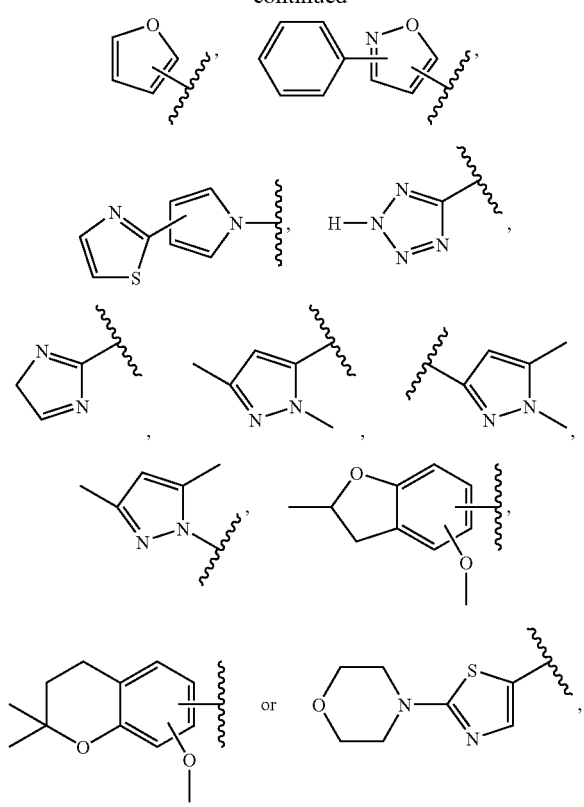
wherein $R^{11}$ is hydrogen; lower alkyl; hydroxy; amino; alkoxy; SO$_2$-lower alkyl; or an unsubstituted alicyclic, aromatic, heterocyclic or heteroaromatic ring; and $R^{12}$ is hydrogen or $C_{1-3}$ alkyl.
Specific values for
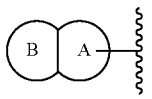
include
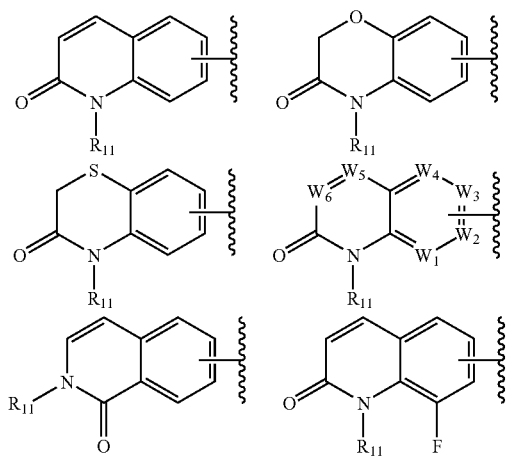
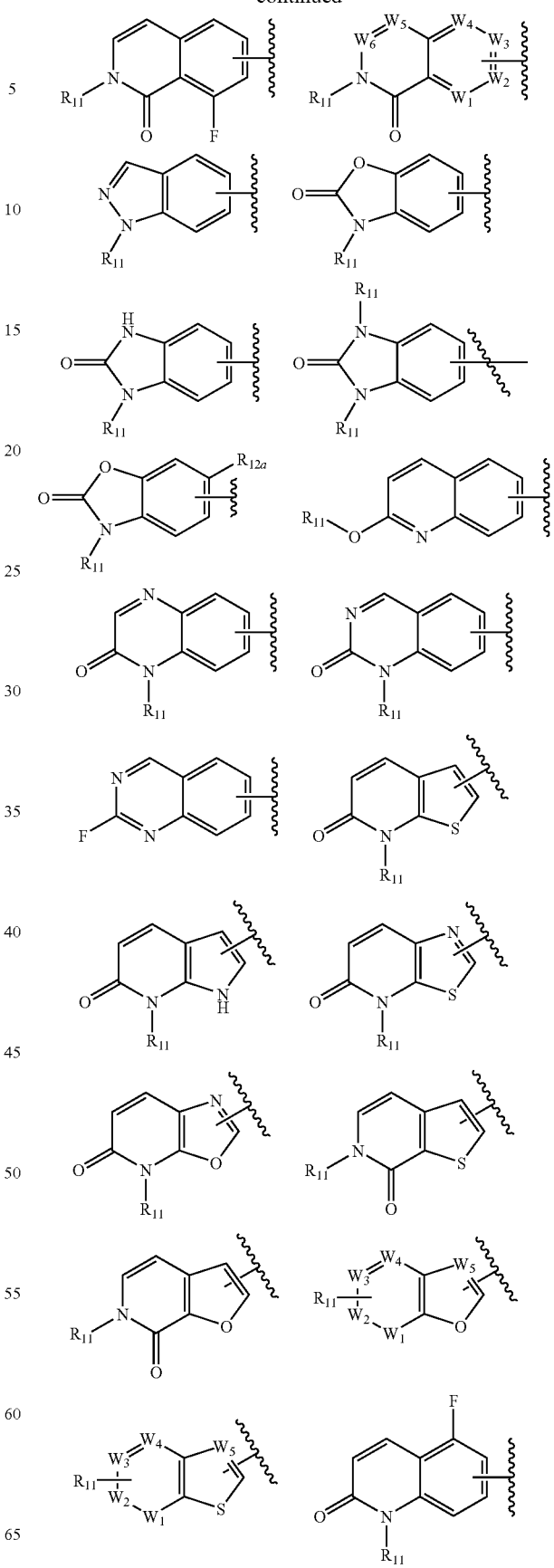

-continued

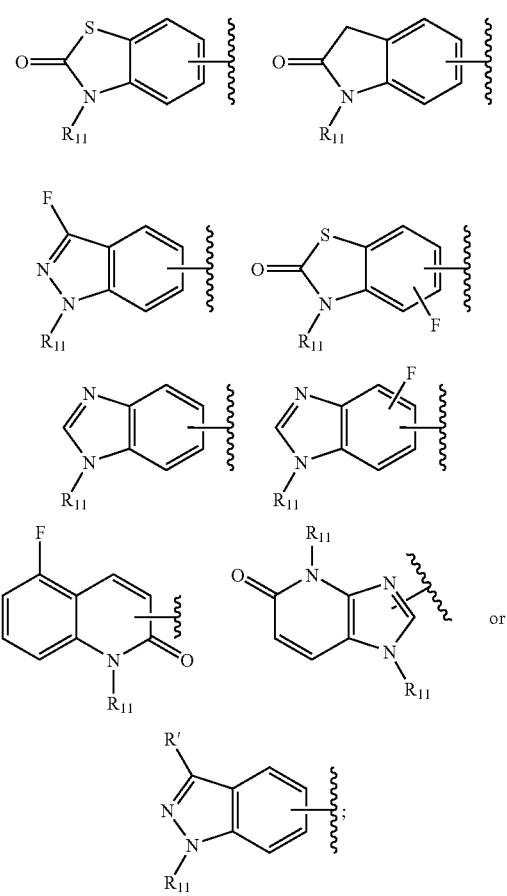

wherein $W_1$, $W_2$, $W_3$, $W_4$ or $W_5$ are independently C, N, C=O, C—OH, C—$OR_{10}$ or C—$R_{10}$;

$R_{10}$ is hydrogen, $C_{1-6}$ alkyl, $C_{1-5}$ alkylthio, $C_{1-5}$ alkoxy, halogen, hydroxyl, cyano, halogen-substituted $C_{1-6}$ alkyl, or halogen-substituted $C_{1-5}$ alkoxy;

$R_{11}$ is hydrogen or is $C_{1-6}$ alkyl, ($C_1$-$C_6$alkylene)cycloalkyl, aralkyl, heteroaralkyl, any of which may be optionally substituted with halo, hydroxy, alkyl, alkenyl, cycloalkyl, $C_{1-3}$alkoxy, —$CO_2H$, —$CO_2C_{1-3}$alkyl, cyano, aryl, heteroaryl, —$CF_3$, —O—$CF_3$, —O—$CH_2F$, or —O—$CHF_2$;

$R_{12a}$ is H, halo, alkoxy, or alkyl; and

R' is alkyl, haloalkyl, or cycloalkyl.

A specific value for $R_5$ is fluoro. Another specific value for $R_5$ is chloro. Other specific values for $R_5$ include methyl, ethyl, methoxy, ethoxy, trifluoromethyl, or trifluoromethoxy. When 2 $R_5$ groups are attached to the same carbon, they may be taken together to form a 3, 4, 5, or 6-membered ring or an oxo (i.e., C=O) group.

A specific value for

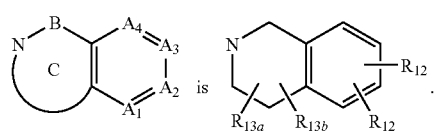

Other specific values for

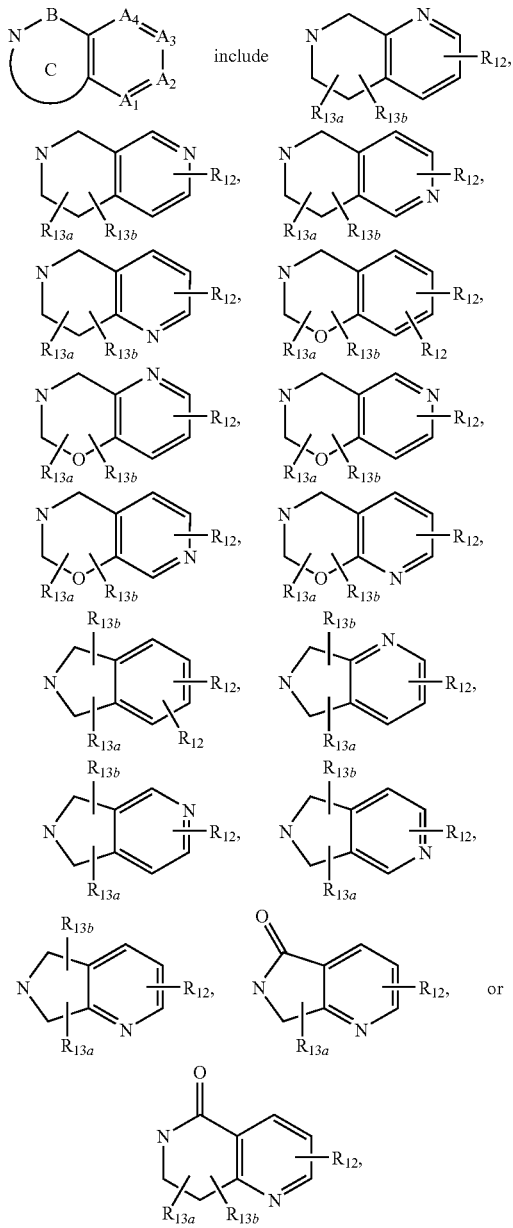

wherein $R_{12}$ independently for each occurrence is hydrogen, halo, alkyl, haloalkyl, haloalkoxy, alkoxy, or cyano; and $R_{13a}$ and $R_{13b}$ are each independently hydrogen, halo, alkyl, haloalkyl, alkoxy, haloalkoxy, or if $R_{13a}$ and $R_{13b}$ are attached to the same carbon, they can form C=O when taken together with the carbon to which they are attached.

A specific value for $R_{12}$ is hydrogen, halo, alkyl, or haloalkyl. More specifically, $R_{12}$ is fluoro, chloro, methyl, ethyl, or trifluoromethyl.

Specific values for $R_{13a}$ and $R_{13b}$ are each independently hydrogen, halo, alkyl, haloalkyl, alkoxy, or haloalkoxy. More specifically, $R_{13a}$ and $R_{13b}$ each independently are fluoro, chloro, methyl, ethyl, trifluoromethyl, methoxy, or trifluoromethoxy.

A specific value for n is 1. Another specific value for n is 2. A specific value for p is 1. Another specific value for p is 2. In certain embodiments, p is 1, and n is 1 or 2. In certain embodiments, p is 2 and n is 1.

A specific group of compounds of the invention are compounds of formula I-A1:

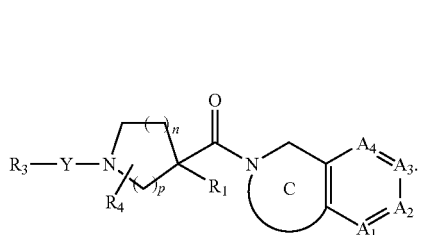
(I-A1)

Another specific group of compounds of the invention are compounds of formula I-A2:

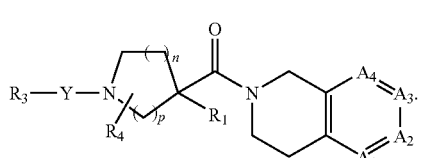
(I-A2)

Another specific group of compounds of the invention are compounds of formula I-A3:

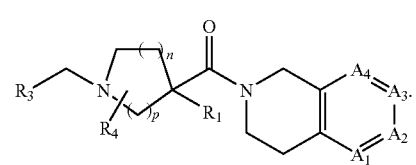
(I-A3)

Another specific group of compounds of the invention are compounds of formula I-A4:

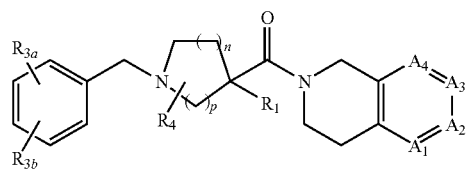
(I-A4)

wherein $R_{3a}$ and $R_{3b}$ are each independently hydrogen, halo, hydroxy, lower alkyl, lower alkenyl, cycloalkyl, $C_{1-3}$ alkoxy, cyano, or $CF_3$, or $R_{3a}$ and $R_{3b}$ taken together form

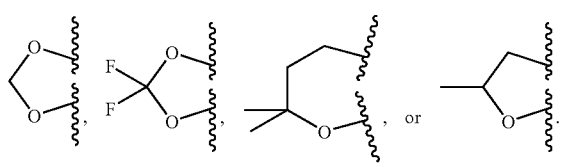

Another specific group of compounds of the invention are compounds of formula I-A5:

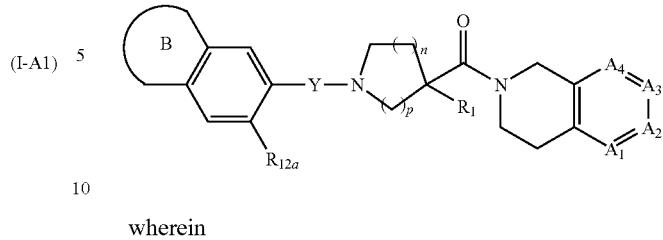
(I-A5)

wherein

is an aromatic or unsaturated ring which may be optionally substituted with 1 or 2 groups selected from halo, hydroxy, alkyl, alkenyl, cycloalkyl, $C_{1-3}$alkoxy, —$CO_2H$, —$CO_2C_{1-3}$ alkyl, cyano, aryl, heteroaryl, —$CF_3$, —O—$CF_3$, —O—$CH_2F$, —O—$CHF_2$, —N(H)alkyl, —N(H)$SO_2$-alkyl, —N(H)C(O)alkyl, or —$SO_2$N(H)alkyl; and $R_{12a}$ is selected from the group consisting of H, halo, alkyl, or alkoxy.

Another specific group of compounds of the invention are compounds of formula I-A6:

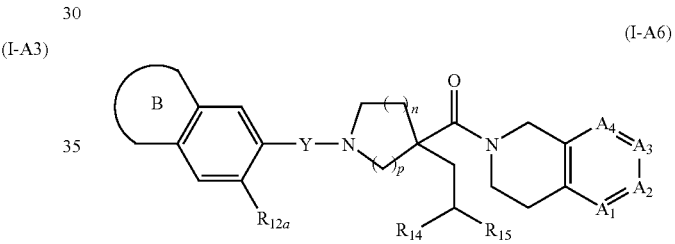
(I-A6)

wherein $R_{14}$ and $R_{15}$ are each independently optionally substituted alkyl or taken together with the carbons to which they are attached form a 3, 4, 5, or 6-membered ring optionally containing one heteroatom selected from the group consisting of O, S, NH, and N-alkyl, which ring is optionally substituted with 1, 2, or 3 groups selected from the group consisting of halo, alkyl, alkoxy, and haloalkoxy; and $R_{12a}$ is selected from the group consisting of H, halo, alkyl, or alkoxy.

Another specific group of compounds of the invention are compounds of formula I-A7:

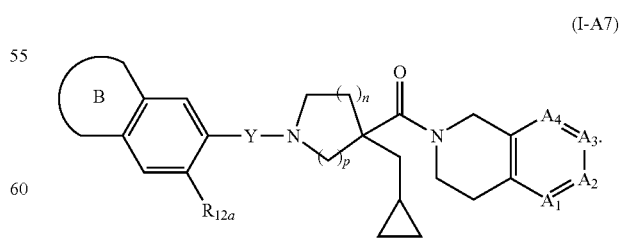
(I-A7)

where $R_{12a}$ is selected from the group consisting of H, halo, alkyl, or alkoxy.

Another specific group of compounds of the invention are compounds of formula I-A8:

(I-A8)

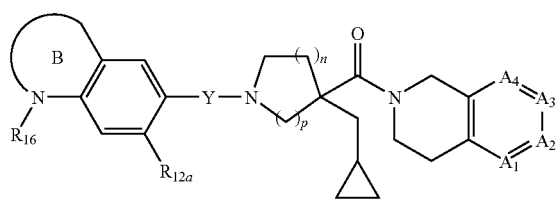

wherein $R_{16}$ is H, or is alkyl, cycloalkyl, ($C_1$-$C_6$alkylene) cycloalkyl, aralkyl, heteroaralkyl, any of which may be optionally substituted with halo, hydroxy, alkyl, alkenyl, cycloalkyl, $C_{1-3}$alkoxy, —$CO_2H$, —$CO_2C_{1-3}$alkyl, cyano, aryl, heteroaryl, —$CF_3$, —O—$CF_3$, —O—$CH_2F$, or —O—$CHF_2$; and $R_{12a}$ is selected from the group consisting of H, halo, alkyl, or alkoxy.

In certain embodiments, the invention provides one of the aforementioned compounds, wherein p is 1. In certain other embodiments, p is 2. In certain other embodiments, p is 2 and n is 1.

Another specific group of compounds of the invention are compounds of formula I-B1:

(I-B1)

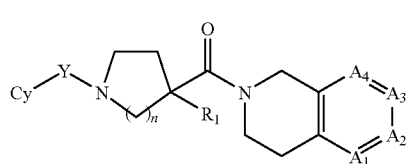

wherein Cy is an unsubstituted cyclic or bicyclic ring optionally having partial aromaticity and optionally having one or more heteroatoms; or pharmaceutically acceptable salts thereof; and Y may be a direct bond or alkyl. Specific values for Cy include

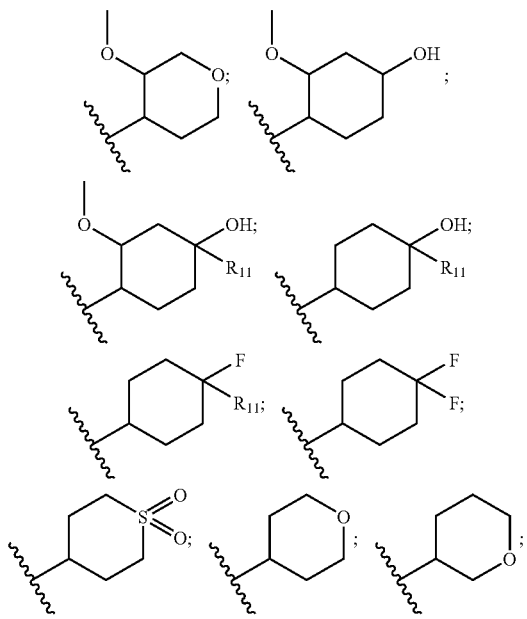

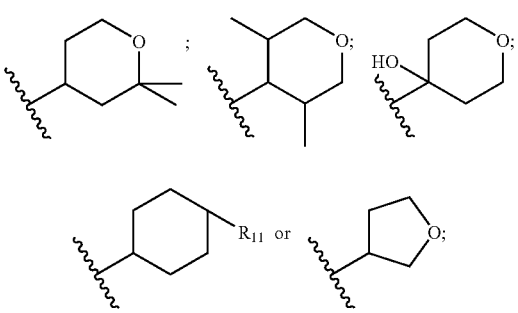

wherein $R_{11}$ is hydrogen or is $C_{1-6}$ alkyl, ($C_1$-$C_6$alkylene) cycloalkyl, aralkyl, or heteroaralkyl, any of which may be optionally substituted with halo, hydroxy, alkyl, alkenyl, cycloalkyl, $C_{1-3}$alkoxy, —$CO_2H$, —$CO_2C_{1-3}$alkyl, cyano, aryl, heteroaryl, —$CF_3$, —O—$CF_3$, —O—$CH_2F$, or —O—$CHF_2$.

Another specific group of compounds of the invention are compounds of formula I-B2:

(I-B2)

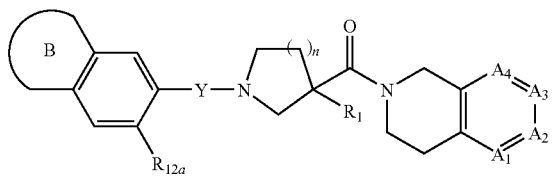

wherein

is an unsaturated heterocyclic ring optionally substituted with 1 or 2 groups selected from the group consisting of halo, alkyl, and oxo; Y is $C_1$-$C_3$ alkylene; and $R_1$ is alkoxyalkyl or alkyl; and $R_{12a}$ is selected from the group consisting of H, halo, alkyl, or alkoxy.

Another specific group of compounds of the invention are compounds of formula I-B3:

(I-B3)

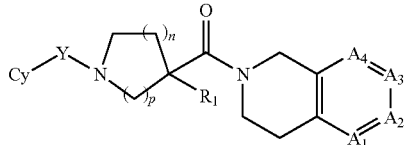

wherein Cy is an unsubstituted cyclic or bicyclic ring optionally having partial aromaticity and optionally having one or more heteroatoms; or pharmaceutically acceptable salts thereof; and Y may be a direct bond or alkyl. Specific values for Cy include

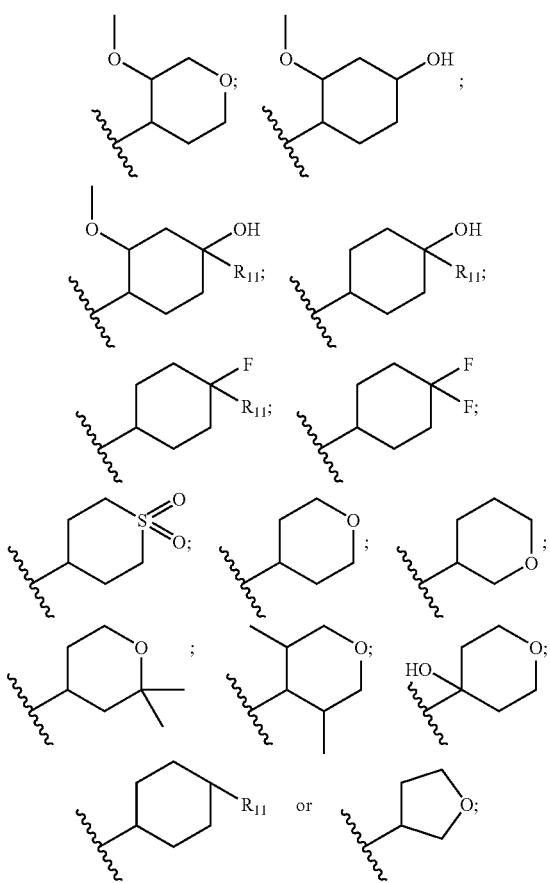

wherein $R_{11}$ is hydrogen or is $C_{1-6}$ alkyl, ($C_1$-$C_6$alkylene) cycloalkyl, aralkyl, or heteroaralkyl, any of which may be optionally substituted with halo, hydroxy, alkyl, alkenyl, cycloalkyl, $C_{1-3}$alkoxy, —$CO_2H$, —$CO_2C_{1-3}$alkyl, cyano, aryl, heteroaryl, —$CF_3$, —O—$CF_3$, —O—$CH_2F$, or —O—$CHF_2$.

Another specific group of compounds of the invention are compounds of formula I-B4:

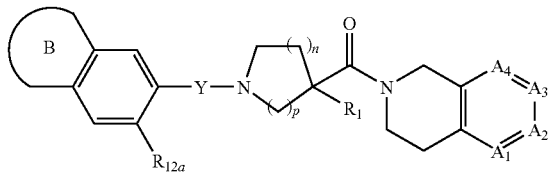

(I-B4)

wherein

is an unsaturated heterocyclic ring optionally substituted with 1 or 2 groups selected from the group consisting of halo, alkyl, and oxo; Y is $C_1$-$C_3$ alkylene; and $R_1$ is alkoxyalkyl or alkyl; and $R_{12a}$ is selected from the group consisting of H, halo, alkyl, or alkoxy.

In certain embodiments, the invention provides one of the aforementioned compounds, wherein p is 1. In certain other embodiments, p is 2. In certain other embodiments, n is 1 or 2. In certain other embodiments, p is 2 and n is 1.

In certain embodiments, the compound is (1-(4-hydroxy-3-methoxybenzyl)-4-isobutylpiperidin-4-yl)(3-(trifluoromethyl)-7,8-dihydro-1,6-naphthyridin-6(5H)-yl)methanone; 7-((4-isobutyl-4-(3-(trifluoromethyl)-5,6,7,8-tetrahydro-1,6-naphthyridine-6-carbonyl)piperidin-1-yl)methyl)-1-methylquinolin-2(1H)-one; (3-(cyclopropylmethyl)-1-(4-hydroxy-3-methoxybenzyl)pyrrolidin-3-yl)(3-(trifluoromethyl)-7,8-dihydro-1,6-naphthyridin-6(5H)-yl)methanone; 7-(3-(cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; (S)-7-((3-(cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; (R)-7-(3-(cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; 3-(cyclopropylmethyl)-1-(3-fluoro-4-hydroxybenzyl)pyrrolidin-3-yl)(3-(trifluoromethyl)-7,8-dihydro-1,6-naphthyridin-6(5H)-yl)methanone; (3-(cyclopropylmethyl)-1-((tetrahydro-2H-pyran-4-yl)methyl)pyrrolidin-3-yl)(3-(trifluoromethyl)-7,8-dihydro-1,6-naphthyridin-6(5H)-yl)methanone; or a pharmaceutically acceptable salt thereof.

In certain other embodiments, the compound is (3-(cyclopropylmethyl)-1-(2,2-dimethyltetrahydro-2H-pyran-4-yl)methyl)pyrrolidin-3-yl)(3-(trifluoromethyl)-7,8-dihydro-1,6-naphthyridin-6(5H)-yl)methanone; (3-(cyclopropylmethyl)-1-(5-methoxy-2-methyl-2,3-dihydrobenzofuran-6-yl)methyl)pyrrolidin-3-yl)(3-(trifluoromethyl)-7,8-dihydro-1,6-naphthyridin-6(5H)-yl)methanone; 5-(3-(cyclopropylmethyl)-3-(3-(trifluoromethyl)-5,6,7,8-tetrahydro-1,6-naphthyridine-6-carbonyl)pyrrolidin-1-yl)methyl)-3-methylbenzo[d]thiazol-2(3H)-one; 5-((3-(cyclopropylmethyl)-3-(3-(trifluoromethyl)-5,6,7,8-tetrahydro-1,6-naphthyridine-6-carbonyl)pyrrolidin-1-yl)methyl)benzo[d]thiazol-2(3H)-one; 3-(cyclopropylmethyl)-1-(4-hydroxy-4-(6-methoxypyridin-3-yl)cyclohexyl)pyrrolidin-3-yl)(3-(trifluoromethyl)-7,8-dihydro-1,6-naphthyridin-6(5H)-yl)methanone; (3-(cyclopropylmethyl)-1-(2,2-dimethylchromoa-6-yl)methyl)pyrrolidin-3-yl)(3-(trifluoromethyl)-7,8-dihydro-1,6-naphthyridin-6(5H)-yl)methanone; 7-(3-(cyclopropylmethyl)-3-(3-(trifluoromethyl)-5,6,7,8-tetrahydro-1,6-naphthyridin-6-carbonyl)pyrrolidin-1-yl)methyl)quinolin-2(1H)-one; 5-(1-(3-(cyclopropylmethyl)-3-(3-(trifluoromethyl)-5,6,7,8-tetrahydro-1,6-naphthyridine-6-carbonyl)pyrrolidin-1-yl)ethyl)-1,3-dimethyl-1H-benzo[d]imidazol-2(3H)-one; (1-((1H-indazol-5-yl)methyl)-3-(cyclopropylmethyl)pyrrolidin-3-yl)(3-(trifluoromethyl)-7,8-dihydro-1,6-naphthyridin-6(5H)-yl)methanone; (3-(cyclopropylmethyl)-1-(4-hydroxy-4-(6-methoxypyridin-3-yl)cyclohexyl)pyrrolidin-3-yl)(3-(trifluoromethyl)-7,8-dihydro-1,6-naphthyridin-6(5H)-yl)methanone; 6-((3-(cyclobutylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; 6-((3-isopentyl-3-(3-(trifluoromethyl)-5,6,7,8-tetrahydro-1,6-naphthyridine-6-carbonyl)pyrrolidin-1-yl)methyl)-1-methylquinolin-2(1H)-one; 6-((3-benzyl-3-(3-(trifluoromethyl)-5,6,7,8-tetrahydro-1,6-naphthyridine-6-carbonyl)pyrrolidin-1-yl)methyl)-1-methylquinolin-2(1H)-one; 6-((3-(cyclopropylmethyl)-3-(3-(trifluoromethyl)-5,6,7,8-tetrahydro-1,6-naphthyridine-6- carbonyl)pyrrolidin-1-yl)methyl)-1-methylquinolin-2(1H)-one; 5-((3-(cyclopropylmethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 5-((3-isobutyl-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 7-((3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; (S)-7-((3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; (R)-7-(3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; 5-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]thiazol-2(3H)-one; 5-(1-(3-(methoxymethyl)-3-(3-(trifluoromethyl)-5,6,7,8-tetrahydro-1,6-naphthyridine-6-carbonyl)pyrrolidin-1-yl)ethyl)-1,3-dimethyl-1H-benzo[d]imidazol-2(3H)-one; (1-(4-hydroxy-4-(6-methoxypyridin-3-yl)cyclohexyl)-3-(methoxymethyl)pyrrolidin-3-yl)(3-(trifluoromethyl)-7,8-dihydro-1,6-naphthyridin-6(5H)-yl)methanone; 6-((3-(methoxymethyl)-3-(3-(trifluoromethyl)-5,6,7,8-tetrahydro-1,6-naphthyridine-6-carbonyl)pyrrolidin-1-yl)methyl)-4-methyl-2H-benzo[b][1,4]oxazin-3(4H)-one; 6-(1-(3-(methoxymethyl)-3-(3-(trifluoromethyl)-5,6,7,8-tetrahydro-1,6-naphthyridine-6-carbonyl)pyrrolidin-1-yl)ethyl)-4-methyl-2H-benzo[b][1,4]oxazin-3(4H)-one; 5-(1-(3-(methoxymethyl)-3-(3-(trifluoromethyl)-5,6,7,8-tetrahydro-1,6-naphthyridine-6-carbonyl)pyrrolidin-1-yl)ethyl)-3-methylbenzo[d]oxazol-2(3H)-one; (1-(4-cyclopropyl-4-hydroxycyclohexyl)-3-(methoxymethyl)pyrrolidin-3-yl)(3-(trifluoromethyl)-7,8-dihydro-1,6-naphthyridin-6(5H)-yl)methanone; 6-chloro-7-((3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one; 6-chloro-5-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 5-((3-(methoxymethyl)-3-(3-(trifluoromethyl)-5,6,7,8-tetrahydro-1,6-naphthyridine-6-carbonyl)pyrrolidin-1-yl)methyl)-1,3-dimethyl-1H-benzo[d]imidazol-2(3H)-one; 5-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; (R)-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one and (S)-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 3-ethyl-6-((3-(methoxymethyl)-3-(3-(trifluoromethyl)-5,6,7,8-tetrahydro-1,6-naphthyridine-6-carbonyl)pyrrolidin-1-yl)methyl)benzo[d]oxazol-2(3H)-one; 5-bromo-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 6-((3-(methoxymethyl)-3-(3-(trifluoromethyl)-5,6,7,8-tetrahydro-1,6-naphthyridine-6-carbonyl)pyrrolidin-1-yl)methyl)-3,5-dimethylbenzo[d]oxazol-2(3H)-one; 5-((3-(ethoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 5-((3-(methoxymethyl)-3-(7-(trifluoromethyl)-1,2,3,4-tetrahydroisoquinoline-2-carbonyl)pyrrolidin-1-yl)methyl)-3-methylbenzo[d]oxazol-2(3H)-one; 5-((3-isopropyl-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 2-(1-((3-methyl-2-oxo-2,3-dihydrobenzo[d]oxazol-5-yl)methyl)-3-(3-(trifluoromethyl)-5,6,7,8-tetrahydro-1,6-naphthyridine-6-carbonyl)pyrrolidin-3-yl)acetonitrile; 5-((3-(hydroxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; (3-(methoxymethyl)-1-(4-(6-methoxypyridin-3-yl)cyclohexyl)pyrrolidin-3-yl)(3-(trifluoromethyl)-7,8-dihydro-1,6-naphthyridin-6(5H)-yl)methanone; (1-(4-hydroxy-4-(pyrimidin-5-yl)cyclohexyl)-3-(methoxymethyl)pyrrolidin-3-yl)(3-(trifluoromethyl)-7,8-dihydro-1,6-naphthyridin-6(5H)-yl)methanone; (3-(methoxymethyl)-1-(4-(pyrimidin-5-yl)cyclohexyl)pyrrolidin-3-yl)(3-(trifluoromethyl)-7,8-dihydro-1,6-naphthyridin-6(5H)-yl)methanone; (1-(4-(4-fluorophenyl)cyclohexyl)-3-(methoxymethyl)pyrrolidin-3-yl)(3-(trifluoromethyl)-7,8-dihydro-1,6-naphthyridin-6(5H)-yl)methanone; 6-((4-isobutyl-4-(3-(trifluoromethyl)-5,6,7,8-tetrahydro-1,6-naphthyridine-6-carbonyl)piperidin-1-yl)methyl)-3-methylbenzo[d]thiazol-2(3H)-one; 6-((4-isobutyl-4-(3-(trifluoromethyl)-5,6,7,8-tetrahydro-1,6-naphthyridine-6-carbonyl)piperidin-1-yl)methyl)-3-methylbenzo[d]oxazol-2(3H)-one; 2-(3-(methoxymethyl)-1-((3-methyl-2-oxo-2,3-dihydrobenzo[d]oxazol-5-yl)methyl)pyrrolidine-3-carbonyl)-7-(trifluoromethyl)-1,2,3,4-tetrahydroisoquinoline-5-carbonitrile; 5-((3-(methoxymethyl)-3-(7-(trifluoromethyl)-1,2,3,4-tetrahydroisoquinoline-2-carbonyl)pyrrolidin-1-yl)methyl)-3-methylbenzo[d]oxazol-2(3H)-one; 6-(3-(methoxymethyl)-1-((3-methyl-2-oxo-2,3-dihydrobenzo[d]oxazol-5-yl)methyl)pyrrolidine-3-carbonyl)-5,6,7,8-tetrahydro-1,6-naphthyridine-3-carbonitrile; 5-((3-(methoxymethyl)-3-(1,2,3,4-tetrahydroisoquinoline-2-carbonyl)pyrrolidin-1-yl)methyl)-3-methylbenzo[d]oxazol-2(3H)-one; 5-((3-(methoxymethyl)-3-(3-(trifluoromethyl)-6,7-dihydro-5H-pyrrolo[3,4-b]pyridine-6-carbonyl)pyrrolidin-1-yl)methyl)-3-methylbenzo[d]oxazol-2(3H)-one; 5-(2-(3-(methoxymethyl)-3-(3-(trifluoromethyl)-5,6,7,8-tetrahydro-1,6-naphthyridine-6-carbonyl)pyrrolidin-1-yl)propan-2-yl)-3-methylbenzo[d]oxazol-2(3H)-one; 5-(1-(3-(methoxymethyl)-3-(3-(trifluoromethyl)-5,6,7,8-tetrahydro-1,6-naphthyridine-6-carbonyl)pyrrolidin-1-yl)cyclopropyl)-3-methylbenzo[d]oxazol-2(3H)-one; 6-(1-(3-(ethoxymethyl)-3-(3-(trifluoromethyl)-5,6,7,8-tetrahydro-1,6-naphthyridine-6-carbonyl)pyrrolidin-1-yl)ethyl)-4-methyl-2H-benzo[b][1,4]oxazin-3(4H)-one; 7-((3-(methoxymethyl)-3-(3-(trifluoromethyl)-5,6,7,8-tetrahydro-1,6-naphthyridine-6-carbonyl)pyrrolidin-1-yl)methyl)-1-methylquinoxalin-2(1H)-one; 7-(1-(3-(methoxymethyl)-3-(3-(trifluoromethyl)-5,6,7,8-tetrahydro-1,6-naphthyridine-6-carbonyl)pyrrolidin-1-yl)ethyl)-1-methylquinoxalin-2(1H)-one; 5-(3-(methoxymethyl)-3-(3-(trifluoromethyl)-5,6,7,8-tetrahydro-1,6-naphthyridine-6-carbonyl)pyrrolidin-1-yl)-3-methyl-3,5,6,7-tetrahydro-2H-indeno[5,6-d]oxazol-2-one; 6-(3-(methoxymethyl)-3-(3-(trifluoromethyl)-5,6,7,8-tetrahydro-1,6-naphthyridine-6-carbonyl)pyrrolidin-1-yl)-1-methyl-7,8-dihydro-1H-indeno[4,5-d]oxazol-2(6H)-one; 6-((3-(methoxymethyl)-3-(3-(trifluoromethyl)-5,6,7,8-tetrahydro-1,6-naphthyridine-6-carbonyl)pyrrolidin-1-yl)methyl)-1-methylindolin-2-one; 6-(1-(3-(methoxymethyl)-3-(3-(trifluoromethyl)-5,6,7,8-tetrahydro-1,6-naphthyridine-6-carbonyl)pyrrolidin-1-yl)ethyl)-1-methylindolin-2-one; (1-(4-(5-fluoropyridin-2-yl)cyclohexyl)-3-(methoxymethyl)pyrrolidin-3-yl)(3-(trifluoromethyl)-7,8-dihydro-1,6-naphthyridin-6(5H)-yl)methanone; (1-(4-fluoro-4-(6-methoxypyridin-3-yl)cyclohexyl)-3-(methoxymethyl)pyrrolidin-3-yl)(3-(trifluoromethyl)-7,8-dihydro-1,6-naphthyridin-6(5H)-yl)methanone; (3-(methoxymethyl)-1-(4-(pyrimidin-2-yl)cyclohexyl)pyrrolidin-3-yl)(3-(trifluoromethyl)-7,8-dihydro-1,6-naphthyridin-6(5H)-yl)methanone; or a pharmaceutically acceptable salt thereof.

The invention also provides pharmaceutical compositions comprising compounds selected from the group of formula I, and the use of these compounds and compositions in the prevention or treatment of diseases in which CCR2 chemokine receptors are involved.

The invention additionally provides a method for the treatment of inflammation, rheumatoid arthritis, lupus, systemic lupus erythematosus, atherosclerosis, restenosis, immune disorders, or transplant rejection in a mammal in need thereof, comprising administering to such mammal a therapeutically effective amount of a pharmaceutical composition containing a compound according to formula I in admixture with a pharmaceutically acceptable excipient, diluent, or carrier.

The invention further provides compositions comprising a compound of the invention and a pharmaceutically acceptable carrier.

The invention further provides methods of modulating activity of a chemokine receptor, comprising exposing said chemokine receptor to a compound of the invention.

The invention further provides methods of treating a disease associated with expression or activity of a chemokine receptor in a patient, comprising administering to the patient a therapeutically effective amount of a compound of the invention.

The invention further provides a compound of Formula I for use in therapy.

The invention further provides use of a compound of Formula I for the manufacture of a medicament for the treatment of disease associated with expression or activity of a chemokine receptor.

The capacity of the compounds of the invention to antagonize CCR2 function can be determined using a suitable screen (e.g., high throughput assay). For example, an agent can be tested in an extracellular acidification assay, calcium flux assay, ligand binding assay or chemotaxis assay (see, for example, Hesselgesser et al., *J Biol. Chem.* 273(25):15687-15692 (1998), WO 00/05265 and WO 98/02151).

The compounds of formula I of the invention, and compositions thereof are useful in the modulation of chemokine receptor activity, particularly CCR2. Accordingly, the compounds of the invention inhibit at least one function or characteristic of a mammalian CCR2 protein, for example, a human CCR2 protein. The ability of a compound to inhibit such a function can be demonstrated in a binding assay (e.g., ligand binding or promoter binding), a signaling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes).

"Prodrug" includes compounds that are transformed in vivo to yield a compound of Formula (I) or a pharmaceutically acceptable salt, hydrate or solvate of the compound. The transformation may occur by various mechanisms, such as through hydrolysis in blood. For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of Formula (I) contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl$(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound of Formula (I) incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$alkyl and $Y^3$ is $(C_1-C_6)$alkyl, carboxy$(C_1-C_6)$alkyl, amino$(C_1-C_4)$alkyl or mono-N- or di-N,N—$(C_1-C_6)$alkylaminoalkyl, —$C(Y^4)Y^5$ wherein $Y^4$ is H or methyl and $Y^5$ is mono-N- or di-N,N—$(C_1-C_6)$alkylamino, morpholino, piperidin-1-yl or pyrrolidin-1-yl.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the invention. In addition, the invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

The compounds of Formula (I) may exist in unsolvated as well as solvated forms with pharmaceutically acceptable solvents such as water, ethanol, and the like, and it is intended that the invention embrace both solvated and unsolvated forms.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of Formula (I) can generally be prepared by following procedures analogous to those disclosed in the Schemes and/or in the Examples hereinbelow, by substituting an isotopically labeled reagent for a non-isotopically labeled reagent.

Compounds of the invention are useful MCP-1 antagonists; therefore, another embodiment of the invention is pharmaceutical compositions comprising a compound of the invention and a pharmaceutically acceptable excipient, diluent or carrier.

Another aspect of the invention is methods for treating or preventing diseases associated with monocyte and/or lymphocyte accumulation which comprises administering a therapeutically effective amount of a compound of the invention to an animal in need thereof. CCR2 receptor antagonists have been shown to inhibit the binding of MCP-1 to its receptor. The compounds of the invention are therefore useful as agents for the treatment of inflammatory diseases, especially those associated with monocyte accumulation, including but not limited to, atherosclerosis, restenosis, gingivitis, glomerulonephritis, psoriasis, colitis, multiple sclerosis, pulmonary fibrosis, Crohn's disease, encephalomyelitis, sepsis, nephritis, asthma, rheumatoid arthritis, wound healing and tissue transplant rejection in animals (preferably humans). Accordingly, the compounds of the invention (including the pharmaceutical compositions and processes used therein) may be used in the manufacture of a medicament for the therapeutic applications described herein (e.g., treatment or prevention of diseases/conditions associated with monocyte and/or lymphocyte accumulation).

One or more additional pharmaceutical agents such as, for example, anti-viral agents, antibodies, anti-inflammatory agents, immunosuppressants, chemotherapeutics can be used in combination with the compounds of the invention for treatment of chemokine receptor-associated diseases, disorders or conditions. These agents can be combined with the compounds of the invention in a single dosage form, or the agents can be administered simultaneously or sequentially as separate dosage forms.

Suitable antiviral agents contemplated for use in combination with the compounds of the invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine; zalcitabine; stavudine; lamivudine; abacavir; adefovir and lodenosine. Typical suitable NNRTIs include nevirapine; delaviradine; efavirenz; and (+)-calanolide A and B. Suitable protease inhibitors include; ritonavir; indinavir; nelfnavir; amprenavir; and lasinavir. Other antiviral agents include hydroxyurea, ribavirin, IL-2, IL-12, and pentafuside.

In some embodiments, anti-inflammatory or analgesic agents contemplated for use in combination with the compounds of the invention can comprise, for example, an opiate agonist, a lipoxygenase inhibitor such as an inhibitor of 5-lipoxygenase, a cyclooxygenase inhibitor such as a cyclooxygenase-2 inhibitor, an interleukin inhibitor such as an interleukin-1 inhibitor, an NNMA antagonist, an inhibitor of nitric oxide or an inhibitor of the synthesis of nitric oxide, a non-steroidal antiinflammatory agent, or a cytokine suppressing antiinflammatory agent, for example, such as acetaminophen, asprin, codiene, ibuprofen, indomethacin, morphine, naproxen, and the like. Similarly, the compounds of the invention may be administered with a pain reliever; a potentiator such as caffeine, an H2 antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedfine, or levo-desoxyephedrine; an antiitussive such as codeine, hydrocodone, caramiphen, carbetapentane, or dextramethorphan; a diuretic; and a sedating or non-sedating antihistamine.

"Individual," "patient," or "subject" are used interchangeably and include to any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of chemokine receptor activity is desired. "Modulation" includes antagonism (e.g., inhibition), agonism, partial antagonism and/or partial agonism. In some embodiments, compounds of the invention are antagonists (e.g., inhibitors) of chemokine receptors.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease, e.g., as rheumatoid arthritis. A therapeutically effective amount of a compound is that amount which results in the inhibition of one or more of the processes mediated by the binding of a chemokine to a receptor such as CCR2 in a subject with a disease associated with aberrant leukocyte recruitment and/or activation. Typical examples of such processes include leukocyte migration, integrin activation, transient increases in the concentration of intracellular free calcium and granule release of proinflammatory mediators. Alternatively, a therapeutically effective amount of a compound is the quantity required to achieve a desired therapeutic and/or prophylactic effect, such as an amount which results in the prevention of or a decrease in the symptoms associated with a disease associated with aberrant leukocyte recruitment and/or activation.

Additional diseases or conditions of human or other species which can be treated with the inhibitors or modulators of chemokine receptor function of the invention, include, but are not limited to: inflammatory or allergic diseases and conditions, including respiratory allergic or diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, restenosis, certain hematologic malignancies, cytokine-induced toxicity (e.g., septic shock, endotoxic shock), polymyositis, and dermatomyositis. Example viral infections include HIV infection.

Suitable pharmaceutical agents that may be used in combination with the compounds of the invention include nutraceuticals, cholesterol absorption inhibitors, HMG-CoA reductase inhibitors, MTP/Apo B secretion inhibitors, HMG-CoA synthase inhibitors, HMG-CoA reductase transcription inhibitors, HMG-CoA reductase translation inhibitors, CETP inhibitors, squalene synthetase inhibitors, squalene epoxidase inhibitors, squalene cyclase inhibitors, combined squalene epoxidase/squalene cyclase inhibitors, ACAT inhibitors, lipase inhibitors (including pancreatic lipase inhibitors and gastric lipase inhibitors) and peroxisome proliferator-activated receptor (PPAR) agonists (preferably PPARα agonists).

Any naturally occurring compound that acts to lower plasma cholesterol levels may be administered in combination with the compounds of the invention. These naturally occurring compounds are referred to herein as "nutraceuticals" and include, for example, garlic extract and niacin.

Any cholesterol absorption inhibitor may be used as the second compound in the combination aspect of this invention. The term "cholesterol absorption inhibition" refers to the ability of a compound to prevent cholesterol contained within the lumen of the intestine from entering into the intestinal cells and/or passing from within the intestinal cells into the blood stream. Such cholesterol absorption inhibition activity is readily determined by those skilled in the art according to standard assays (see, e.g., *J. Lipid Res.* 34, 377-395 (1993)). Suitable cholesterol absorption inhibitors are well known to those skilled in the art and include compounds such as steroidal glycosides which are described in WO 94/00480.

Any HMG-CoA reductase inhibitor may be used as the second compound in the combination aspect of this invention. The term "HMG-CoA reductase inhibitor" refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (see, e.g., *Meth. Enzymol.,* 71, 455-509 (1981) and references cited therein). Suitable HMG-CoA reductase inhibitors include statins, e.g., lovastatin; simvastatin; fluvastatin; pravastatin; rivastatin; atorvastatin and hemicalcium salts thereof; itavostatin (aka nisvastatin, pitavastatin, NK-104) and rosuvastatin.

Any MTP/Apo B secretion (microsomal triglyceride transfer protein and/or apolipoprotein B secretion) inhibitor may be used as the second compound in the combination aspect of this invention. The term "MTP/Apo B secretion inhibitor" refers to compounds which inhibit the secretion of triglycerides, cholesteryl ester, and phospholipids. Such inhibition is readily determined by those skilled in the art according to standard assays (e.g., Wetterau, J. R., *Science,* 258, 999 (1992)). A variety of these compounds are known to those skilled in the art. Suitable MTP/Apo B secretion inhibitors include biphenyl-2-carboxylic acid-tetrahydro-isoquinolin-6-yl amide derivatives, e.g., as described in U.S. Pat. Nos. 5,919,795 and 6,121,283.

Any HMG-CoA synthase inhibitor may be used as the second compound in the combination aspect of this invention. The term "HMG-CoA synthase inhibitor" refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (e.g., *Meth Enzymol.,* 35, 155-160 (1975): *Meth. Enzymol.* 110, 19-26 (1985) and references cited therein). HMG-CoA synthase inhibitors known to those skilled in the art, e.g., as described in U.S. Pat. Nos. 5,120,729 (beta-lactam derivatives); 5,064,856 (spiro-lactone derivatives); and 4,847,271 (oxetane compounds such as 11-(3-hydroxymethyl-4-oxo-2-oxetayl)-3,5,7-trimethyl-2,4-undeca-dienoic acid derivatives).

Any compound that decreases HMG-CoA reductase gene expression may be used as the second compound in the combination aspect of this invention. These agents may be HMG-CoA reductase transcription inhibitors that block or decrease the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (see, e.g., *Meth. Enzymol.,* 110, 9-19 (1985)). Inhibitors of HMG-CoA reductase gene expression are well known to those skilled in the art, e.g., U.S. Pat. No. 5,041,432 (15-substituted lanosterol derivatives); and oxygenated sterols that suppress synthesis of HMG-CoA reductase (*Prog. Lip. Res.,* 32, 357-416 (1993)).

Any compound having activity as a CETP inhibitor can serve as the second compound in the combination therapy aspect of the invention. The term "CETP inhibitor" refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140, 343). A variety of CETP inhibitors will be known to those skilled in the art; e.g., U.S. Pat. Nos. 6,140,343 (4-amino substituted-2-substituted-1,2,3,4-tetrahydroquinolines); 5,512,548 (polypeptide derivatives) and CETP-inhibitory rosenonolactone derivatives and phosphate-containing analogs of cholesteryl ester (*J. Antibiot.*, 49(8), 815-816 (1996), and *Bioorg. Med. Chem. Lett.*, 6, 1951-1954 (1996), respectively).

Any squalene synthetase inhibitor may be used as the second compound of this invention. The term "squalene synthetase inhibitor" refers to compounds which inhibit the condensation of 2 molecules of farnesylpyrophosphate to form squalene, catalyzed by the enzyme squalene synthetase. Inhibition is readily determined by those skilled in the art according to standard assays (e.g., *Meth. Enzymol*, 15, 393-454 (1969) and *Meth. Enzymol*, 110, 359-373 (1985)). A variety of these compounds are known to those skilled in the art, e.g., in U.S. Pat. No. 5,026,554, disclosing fermentation products of the microorganism MF5465 (ATCC 74011) including zaragozic acid. A summary of other squalene synthetase inhibitors has been compiled (*Curr. Op. Ther. Patents*, 3, 861-4 (1993)).

Any squalene epoxidase inhibitor may be used as the second compound in the combination aspect of this invention. "Squalene epoxidase inhibitor" refers to compounds which inhibit the bioconversion of squalene and molecular oxygen into squalene-2,3-epoxide, catalyzed by the enzyme squalene epoxidase. Such inhibition is readily determined by those skilled in the art according to standard assays (e.g., *Biochim Biophys Acta*, 794, 466-471 (1984)). A variety of these compounds are well known to those skilled in the art, e.g., U.S. Pat. Nos. 5,011,859 and 5,064,864 (fluoro analogs of squalene); EP publication 395,768 A (substituted allylamine derivatives); PCT publication WO 9312069 (amino alcohol derivatives); and U.S. Pat. No. 5,051,534 (cyclopropyloxysqualene derivatives).

Any squalene cyclase inhibitor may be used as the second component in the combination aspect of this invention. The term "squalene cyclase inhibitor" refers to compounds which inhibit the bioconversion of squalene-2,3-epoxide to lanosterol, catalyzed by the enzyme squalene cyclase. Inhibition is readily determined by those skilled in the art according to standard assays (e.g., *FEBS Lett.*, 244, 347-350 (1989)). Squalene cyclase inhibitors are well known to those skilled in the art, e.g., U.S. Pat. No. 5,580,881 (1,2,3,5,6,7,8,8a-octahydro-5,5,8a-trimethyl-(8aβ)-6-isoquinolineamine derivatives).

Any combined squalene epoxidase/squalene cyclase inhibitor may be used as the second component in the combination aspect of this invention. The term "combined squalene epoxidase/squalene cyclase inhibitor" refers to compounds that inhibit the bioconversion of squalene to lanosterol via a squalene-2,3-epoxide intermediate. In some assays it is not possible to distinguish between squalene epoxidase inhibitors and squalene cyclase inhibitors. However, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of squalene epoxidase/squalene cyclase inhibitors are well known to those skilled in the art, e.g., U.S. Pat. Nos. 5,084,461 and 5,278,171 (azadecalin derivatives); EP publication 468,434 (piperidyl ether and thio-ether derivatives such as 2-(1-piperidyl)pentyl isopentyl sulfoxide and 2-(1-piperidyl) ethyl ethyl sulfide); PCT publication WO 94/01404 (acylpiperidines such as 1-(1-oxopentyl-5-phenylthio)-4-(2-hydroxy-1-methyl)-ethyl)piperidine; and U.S. Pat. No. 5,102,915 (cyclopropyloxy-squalene derivatives).

Any ACAT inhibitor can serve as the second compound in the combination therapy aspect of this invention. The term "ACAT inhibitor" refers to compounds that inhibit the intracellular esterification of dietary cholesterol by the enzyme acyl CoA: cholesterol acyltransferase. Such inhibition may be determined readily by one of skill in the art according to standard assays, such as the method described in Heider et al., *Journal of Lipid Research.*, 24, 1127 (1983). A variety of these compounds are well known to those skilled in the art, e.g., U.S. Pat. No. 5,510,379 (carboxysulfonates), WO 96/26948 and WO 96/10559 (urea derivatives having ACAT inhibitory activity); DL-melinamide (GB Pat. No. 1,123,004 and *Japan. J. Pharmacol.*, 42, 517-523 (1986); 2,2-dimethyl-N-(2,4,6-trimethoxyphenyl)dodecanamide (U.S. Pat. No. 4,716,175); and N-[2,6-bis(1-methylethyl)phenyl]-N'-[[1-(4-dimethylaminophenyl)cyclopentyl]-methyl]urea (U.S. Pat. No. 5,015,644).

Any lipase inhibitor may be used in combination with the compounds of the invention. The term "lipase inhibitor" refers to a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., *Methods Enzymol*, 286, 190-231 (1997)).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. Gastric lipase inhibition activity is readily determined by those skilled in the art according to standard assays (e.g., *Methods Enzymol*, 286, 190-231 (1997)).

A variety of gastric and/or pancreatic lipase inhibitors are well known to one of ordinary skill in the art, e.g., lipstatin, tetrahydrolipstatin (orlistat), valilactone, esterastin, ebelactone A and ebelactone B; N-3-trifluoromethylphenyl-N'-3-chloro-4'-trifluoromethylphenylurea and derivatives thereof (U.S. Pat. No. 4,405,644); esteracin; cyclo-O,O'-[(1,6-hexanediyl)-bis-(iminocarbonyl)]dioxime; and bis(iminocarbonyl)dioximes.

(2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof (U.S. Pat. No. 4,598,089) tetrahydrolipstatin (U.S. Pat. Nos. 5,274,143; 5,420,305; 5,540,917; and 5,643,874); FL-386, 1-[4-(2-methylpropyl)cyclohexyl]-2-[(phenylsulfonyl)oxy]-ethanone and substituted sulfonate derivatives related thereto (U.S. Pat. No. 4,452,813); and WAY-121898, 4-phenoxyphenyl-4-methylpiperidin-1-ylcarboxylate, and carbamate esters and pharmaceutically acceptable salts thereof (U.S. Pat. Nos. 5,512,565; 5,391,571 and 5,602,151); valilactone (Kitahara, et al.).

Other compounds that are marketed for hyperlipidemia may also be used in combination with compounds of the invention, including those compounds marketed for hypercholesterolemia which are intended to help prevent or treat atherosclerosis, for example, bile acid sequestrants, such as Welchol®, Colestid®, LoCholest® and Questran®; and fibric acid derivatives, such as Atromid®, Lopid® and Tricor®. Examples of bile acid sequestrants are also discussed in U.S. Pat. Nos. 3,692,895 and 3,803,237 (colestipol); U.S. Pat. No. 3,383,281 (cholestyramine) and Casdorph R. in *Lipid Pharmacology*, 1976; 2:222-256, Paoletti C., Glueck J., eds. Academic Press, N.Y.

Any peroxisome proliferator-activated receptor (PPAR) agonists (preferably PPARα agonists) can be used in combination with compounds of the invention. Suitable PPAR agonists include fibrates (e.g., bezafibrate, ciprofibrate, clofibrate, fenofibrate, and gemfibrozil, which are all commercially available) and glitazones (e.g., pioglitazone, and rosiglitazone, which are both commercially available). Gemfibrozil is described in U.S. Pat. No. 3,674,836; bezafibrate is described in U.S. Pat. No. 3,781,328; clofibrate is described in U.S. Pat. No. 3,262,850; and fenofibrate is described in U.S. Pat. No. 4,058,552.

Other compounds that may be used in combination with the compounds of the invention include NSAIDs, COX-2 inhibitors, and antiallergics. Suitable nonsteroidal anti-inflammatory drugs (NSAIDS) include compounds such as ibuprofen (Motrin™, Advil™) naproxen (Naprosyn™), sulindac (Clinori™), diclofenac (Voltare™), piroxicam (Feldene™) ketoprofen (Orudis™), diflunisal (Dolobid™), nabumetone (Relafen™), etodolac (Lodine™) oxaprozin (Daypr™), and indomethacin (Indocin™). Suitable COX-2 inhibitors (cyclooxygenase enzyme inhibitors) include compounds such as celecoxib (Celebrex™) and rofecoxib (Vioxx™).

"Combination therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

The compounds of the invention can be administered to a patient at dosage levels in the range of from about 0.01 to about 100 mg per day. As used herein, the term "unit dose" or "unit dosage" refers to physically discrete units that contain a predetermined quantity of a compound of the invention calculated to produce a desired therapeutic effect. The dosage to be administered may vary depending upon the physical characteristics of the patient, the severity of the patient's symptoms, and the means used to administer the drug. The specific dose for a given patient is usually set by the judgment of the attending physician. It is also noted that the compounds of the invention can be used in sustained release, controlled release, and delayed release formulations, which forms are also well known to one of ordinary skill in the art.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, α-glutaric, α-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives of the compounds of Formula I, such as the compounds quaternized by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide, e.g., chloride, bromide or iodide. Yet other examples of pharmaceutically acceptable salts also include internal salts such as N-oxides. It is contemplated that the compounds described herein may exist in a salt form.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including creams.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Advantageously, the invention also provides kits for use by a consumer having, or at risk of having, a disease or condition associated with monocyte, lymphocyte or leukocyte accumulation, which can be ameliorated by a CCR2 antagonist. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units.

Since the invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of the invention and a second pharmaceutical agent as described above. The kit comprises a container (e.g., a divided bottle or a divided foil packet). Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Biological Activity of Compounds

The suitability of compounds described herein for the uses described herein may be determined by methods and assays known in the art. The following tests are found particularly advantageous.

For determining the ability of compounds to effect chemotaxis, assays in two formats may be used:

Methods Using Boyden Chambers:

Cells are washed twice in RPMI with 0.1% BSA and starved for 2 hours in RPMI 0.1% BSA at 37° C. in 5% $CO_2$. After starving, the cells are resuspended at $1\times10^6$ cell/mL (in some cases, the cell density may be varied in order to investigate the optimal cell numbers that can be used in the assay) in RPMI 0.1% BSA. About $1\times10^5/100$ μL cells are added into the upper wells of the Boyden chamber apparatus with 8 μm pore size filter. Chemotactic factors are diluted to the indicated concentrations in RPMI 0.1% BSA, and 200 μL of the mixture is added into the lower wells of the Boyden chambers. After 2 hours at 37° C. in 5% $CO_2$, the cells remaining in the upper chamber are removed. Migrated cells in the lower surface of the filters are fixed with Methanol and stained with 15% Giemsa. The cells are counted in 10 high power fields.

Methods Using Neuroprobes:

Cells are washed twice in RPMI with 0.1% BSA and starved for 2 hours in RPMI 0.1% BSA at 37° C. in 5% $CO_2$. After starving, the cells are resuspended at $1\times10^6$ cell/mL in RPMI 0.1% BSA and stained with 1 μg/mL Calcein AM for 30 min at 37° C. in 5% $CO_2$. Stained cells are washed twice with PBS and resuspended at $1\times10^6$ cell/mL in RPMI 0.1% BSA. About 25 μL of the cells are added into the upper chambers of the 96-well neuroprobe plates with an 8 μm pore size filter. Chemotactic factors are diluted to the indicated concentrations in RPMI 0.1% BSA, and 30 μL of the mixture is added into the lower chambers of the 96-well neuroprobe plate. After 2 hours at 37° C. in 5% $CO_2$, the cells remaining in the upper chambers are removed and rinsed with PBS once. Migrated cells in the lower surface of the filters and low chamber are determined as the fluorescent value measured at λ450-530 by Cytofluor.

For determining the ability of compounds to bind to CCR2 and to block MCP-1 binding, the following assay is useful. To maximize reliability and reproducibility Human recombinant CHO-K1 cells that overexpress CCR2 are used in this assay. Increasing concentrations of antagonist is incubated with cells in the presence of 1% DMSO, 25 mM HEPES pH: 7.4, 1 mM $CaCl_2$, 0.5% BSA, 5 mM $MgCl_2$, 0.1% sodium azide. The potency of the compounds is calculated as a function of decreasing quantity of $^{125}I$-labeled MCP-1 (1 nM) ability to bind to the receptor. Reference standards are run as an integral part of each assay to ensure the validity of the results obtained. Where presented, $IC_{50}$ values are determined by a non-linear, least squares regression analysis using Data Analysis Toolbox (MDL Information Systems, San Leandro, Calif., USA). Where inhibition constants $K_i$ are presented, the $K_i$ values are calculated using the equation of Cheng and Prusoff (Cheng, Y., Prusoff, W. H., *Biochem. Pharmacol.* 22:3099-3108, 1973) using the observed $IC_{50}$ of the tested compound, the concentration of radioligand employed in the assay, and the historical values for the $K_D$ of the ligand (obtained experimentally at MDS Pharma Services). Where presented, the Hill coefficient ($n_H$), defining the slope of the competitive binding curve, is calculated using Data Analysis Toolbox. Hill coefficients significantly different than 1.0 may suggest that the binding displacement does not follow the laws of mass action with a single binding site. Where $IC_{50}$, $K_i$, and/or $n_H$ data are presented without Standard Error of the Mean (SEM), data are insufficient to be quantitative, and the values presented ($K_i$, $IC_{50}$, $n_H$) should be interpreted accordingly.

The efficacy of compounds of the invention may further be determined using a (GTPγS) assay in which the potency of a given antagonist is assessed by the inhibition observed in the binding of radioactively labeled GTP to the cell membranes or whole cells. Compounds are tested at several concentrations in duplicate (n=2) to obtain a dose-response curve and estimated $IC_{50}$ values. The assay buffer is 20 mM HEPES pH 7.4; 100 mM NaCl, 10 μg/mL saponin, 1 mM $MgCl_2$. The assay is performed on membranes that are thawed on ice and diluted in assay buffer to give 250 μg/mL (5 μg/20 μL), keep on ice. 20 μL of 5 μM GDP (1 μM final). 10 μL of antagonist at increasing concentrations is added successively in the wells of an Optiplate (Perkin Elmer) together with 20 μL of membranes (5 μg) and preincubated for 15 min. at room temperature. To this, 10 μL of assay buffer or of reference agonist (MCP-1 R&D Systems, 279-MC) at $EC_{80}$ (10×), 20 μL of GTPg$^{35}$S (0.1 nM final), 20 μL of PVT-WGA beads (Amersham, RPNQ001). Control antagonist RS 102895 (Tocris, 2089) diluted in assay buffer is used in each assay as a reference. The plate is covered with a topseal, placed on an orbital shaker for 2 min., incubated for 30 min. at room temperature, centrifuged for 10 min. at 2000 rpm, incubated for 2 h at room temperature and counted in a TopCount (Packard) for 1 min.

The following schemes, examples and biological data are given for the purpose of illustrating the invention, and are not intended to limit the scope or spirit of the invention.

Preparation of Compounds

Compounds of the invention may be prepared as described in the following schemes. Starting materials are either commercially available or made by known procedures in the reported literature or as illustrated. This invention provides procedures for the preparation of compounds of formula I as defined above, which comprises different sequences of assembling intermediates of formula (II), formula (III), formula (IV), formula (VII) and formula (VIII).

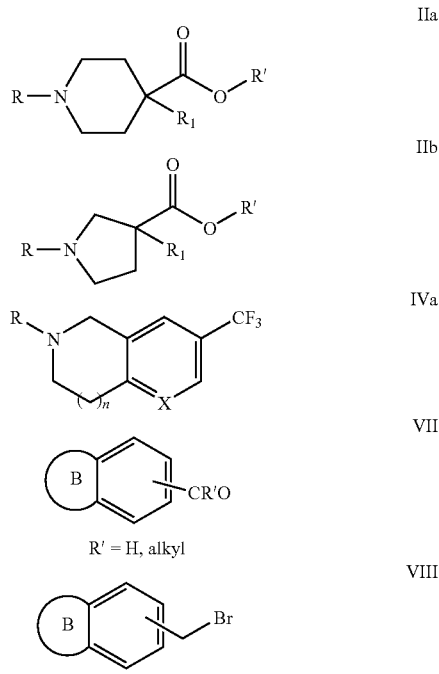

wherein B, and $R^1$ are defined as in formula I, X and Y can be C or NR', R' is H or alkyl, R represents either hydrogen or a protecting group.

General procedures for preparing target molecules Ia and Ib by using intermediates II, III, IV, V, VI, VII and VIII are outlined in Scheme 1 and Scheme 2. Coupling of acid (III) and amine (IV) under standard amide bond formation using activating reagent such as HOBt/EDCI, PyBrop/EDCI with or without catalyst DMAP gives the intermediates Va and Vb. Removal of the Boc protecting group yields the amines (VI). Reductive amination with aldehydes or ketones (VII) in the presence of a reducing reagent such as sodium triacetoxyborohydride and sodium cyanoborohydride finally provides compound I. Alkylation of amine (VI) with an alkyl halide or aryl halide (VIII) in the presence of base such as $K_2CO_3$, or $Cs_2CO_3$ combined with organic base such as DIEA or TEA under elevated temperature also yield the compound of formula I. A mixture of enantiomers, diastereomers, cis/trans isomers resulted from the process can be separated into their single components by chiral salt technique, chromatography using normal phase, reverse phase or chiral column, depending on the nature of the separation.

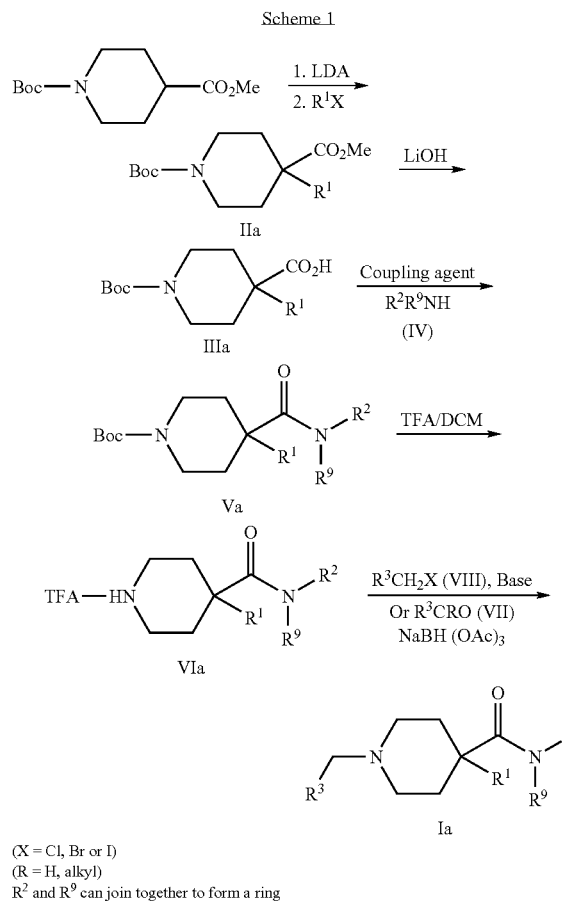

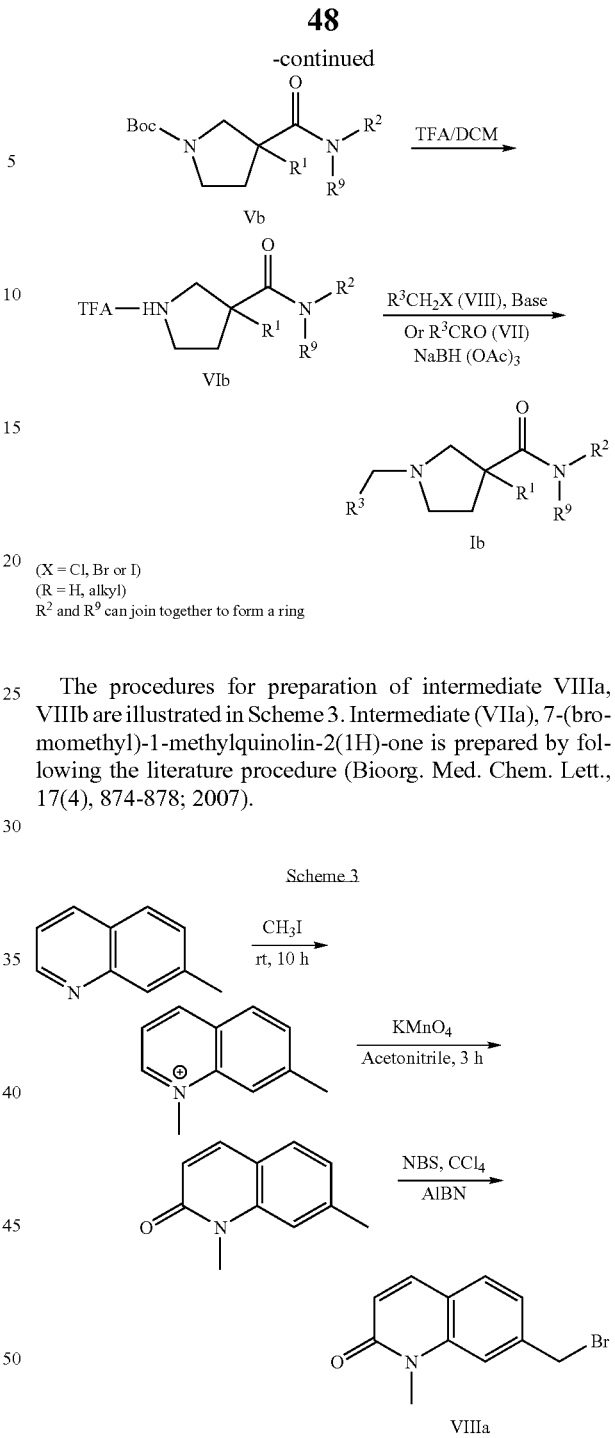

(X = Cl, Br or I)
(R = H, alkyl)
$R^2$ and $R^9$ can join together to form a ring The procedures for preparation of intermediate VIIIa, VIIIb are illustrated in Scheme 3. Intermediate (VIIa), 7-(bromomethyl)-1-methylquinolin-2(1H)-one is prepared by following the literature procedure (Bioorg. Med. Chem. Lett., 17(4), 874-878; 2007).

Synthesis of 3-(trifluoromethyl)-5,6,7,8-tetrahydro-1,6-naphthyridine (IVa) has been reported in literature (WO 2005/105092). The preparative procedures for target molecule Example 1 and 3 are illustrated in Scheme 4 and 5. The coupling of acid (III) and amine (IV) under standard amide bond formation using activating reagent such as HOBt/EDCI was unsuccessful to give desired intermediates Va and Vb. An alternative method is the conversion of acid (III) to acid chloride (IX) using thionyl chloride, followed by coupling reaction with amine (IV) in presence of triethylamine. Removal of the Boc protecting group with 20% TFA in DCM gave the amines (VI). Alkylation of amine (VI) with the intermediate (VIII) in the presence of K₂CO₃ and DIEA was carried out in a Microwave instrument at 110° C. to yield Example 1 and 3.
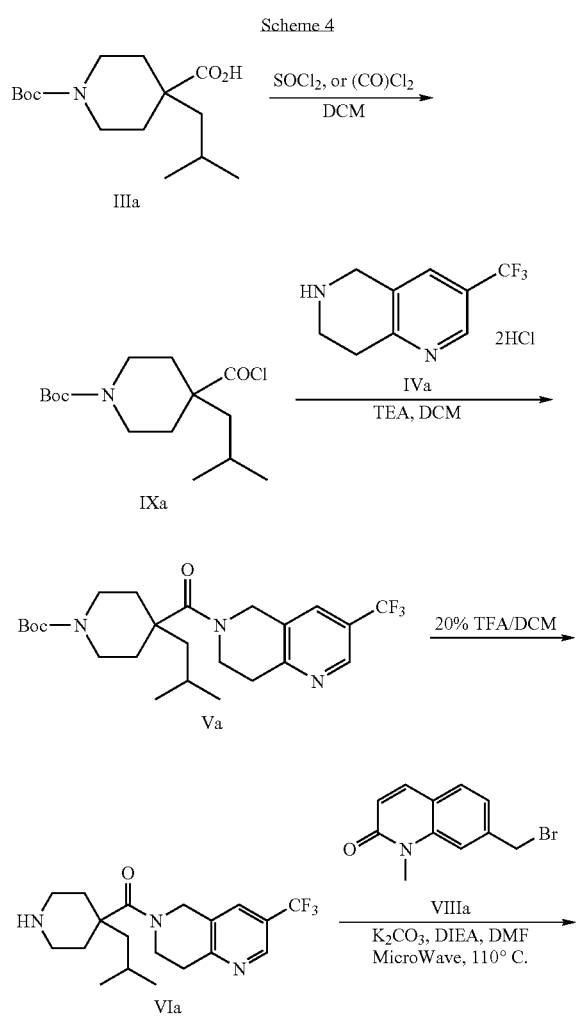
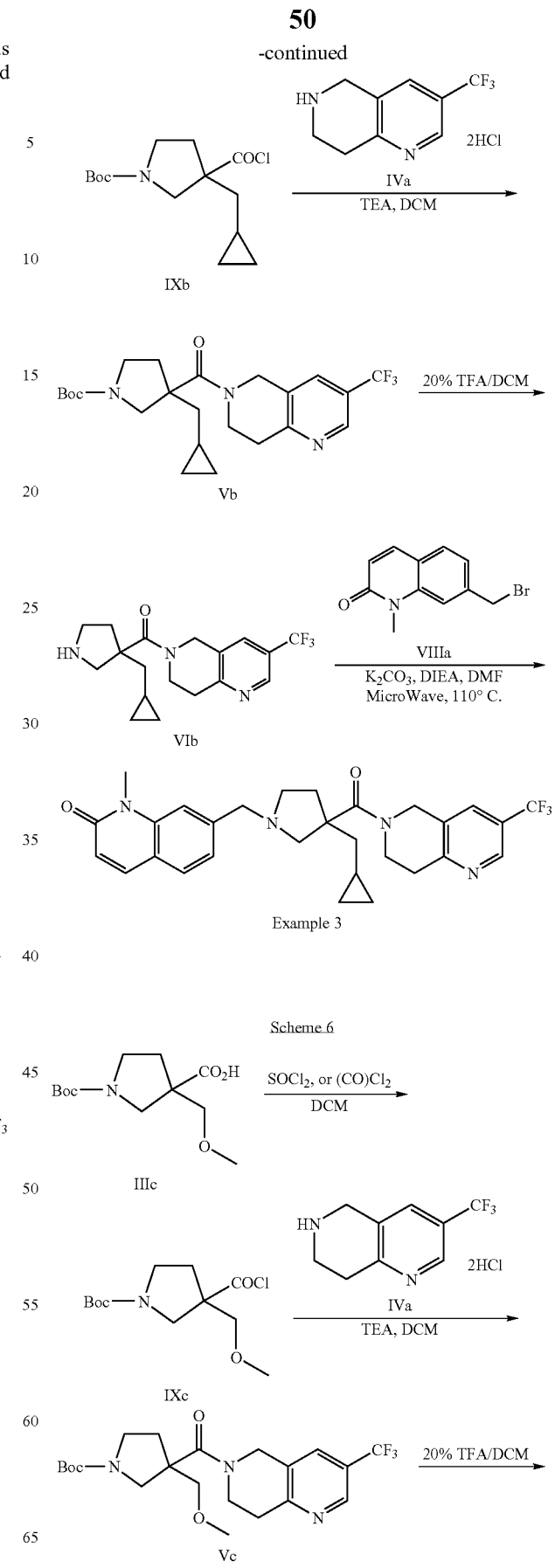

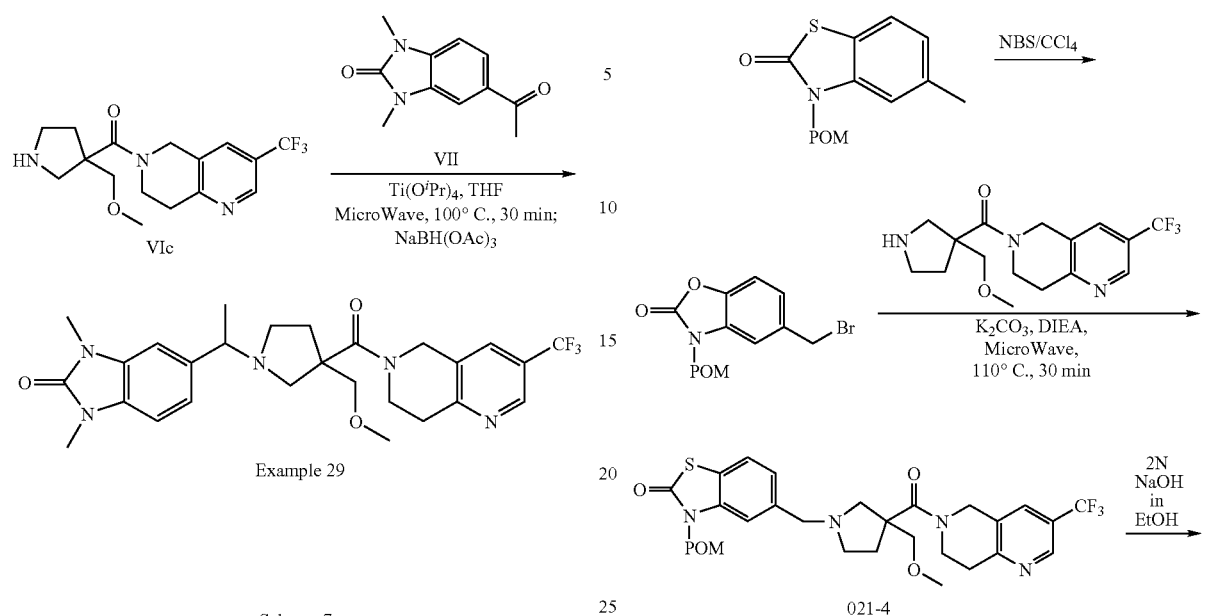
Example 29
Scheme 7
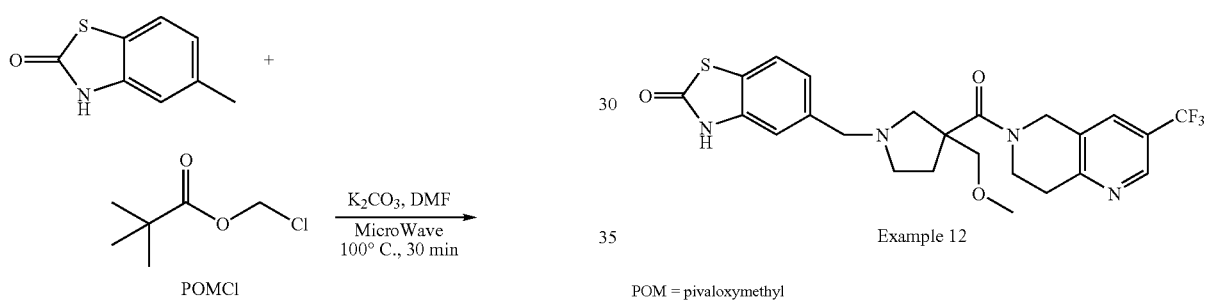
Example 12
POM = pivaloxymethyl
Scheme 8
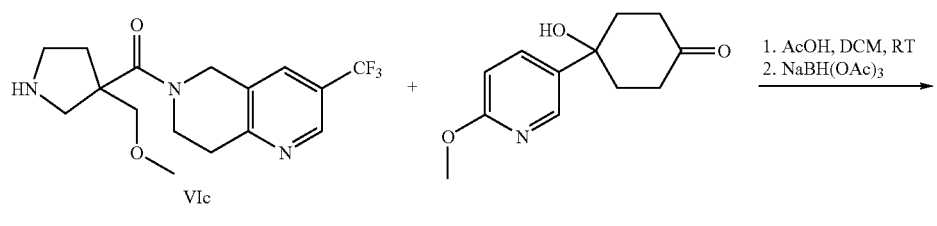
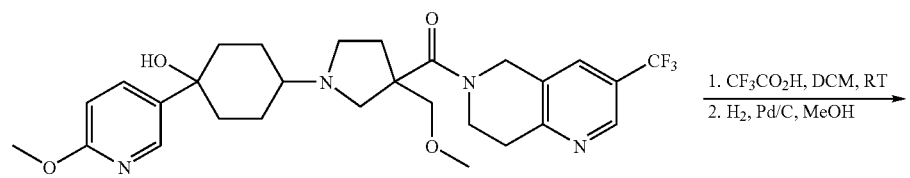
Examples 30 & 31
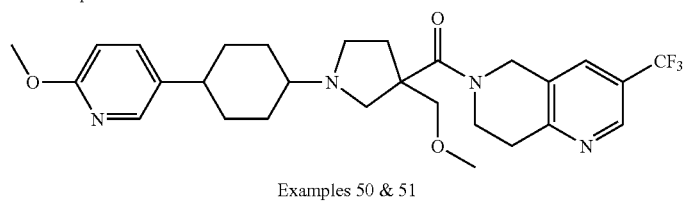
Examples 50 & 51

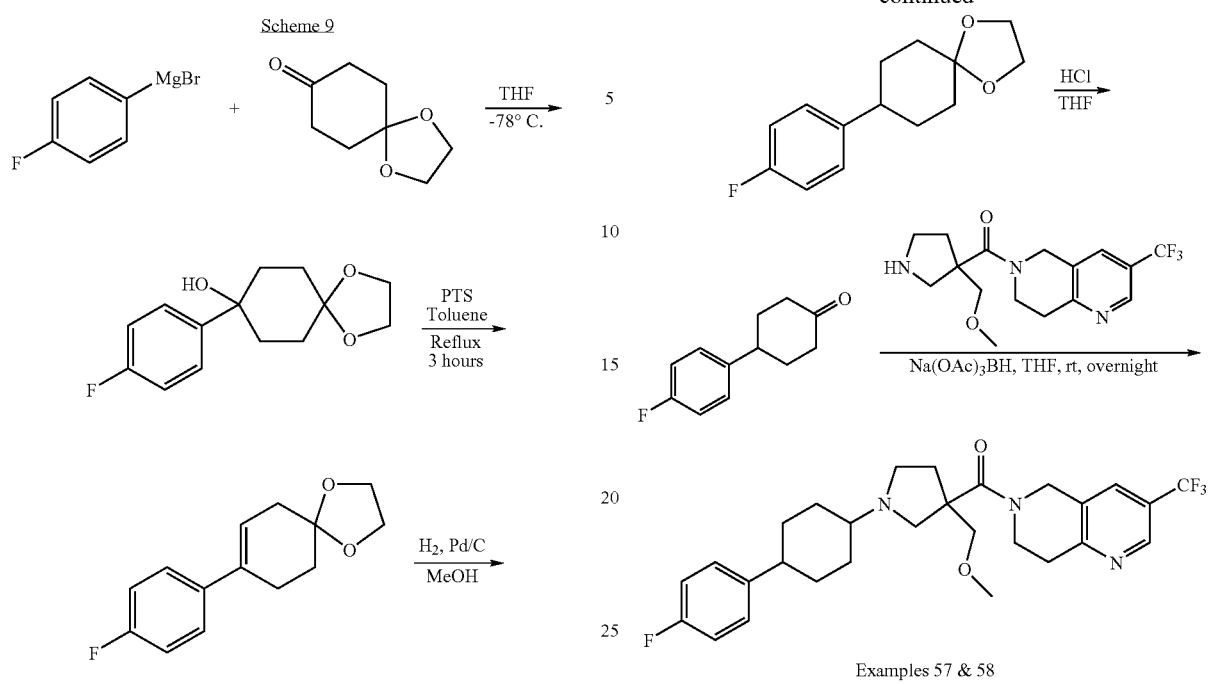
Examples 57 & 58
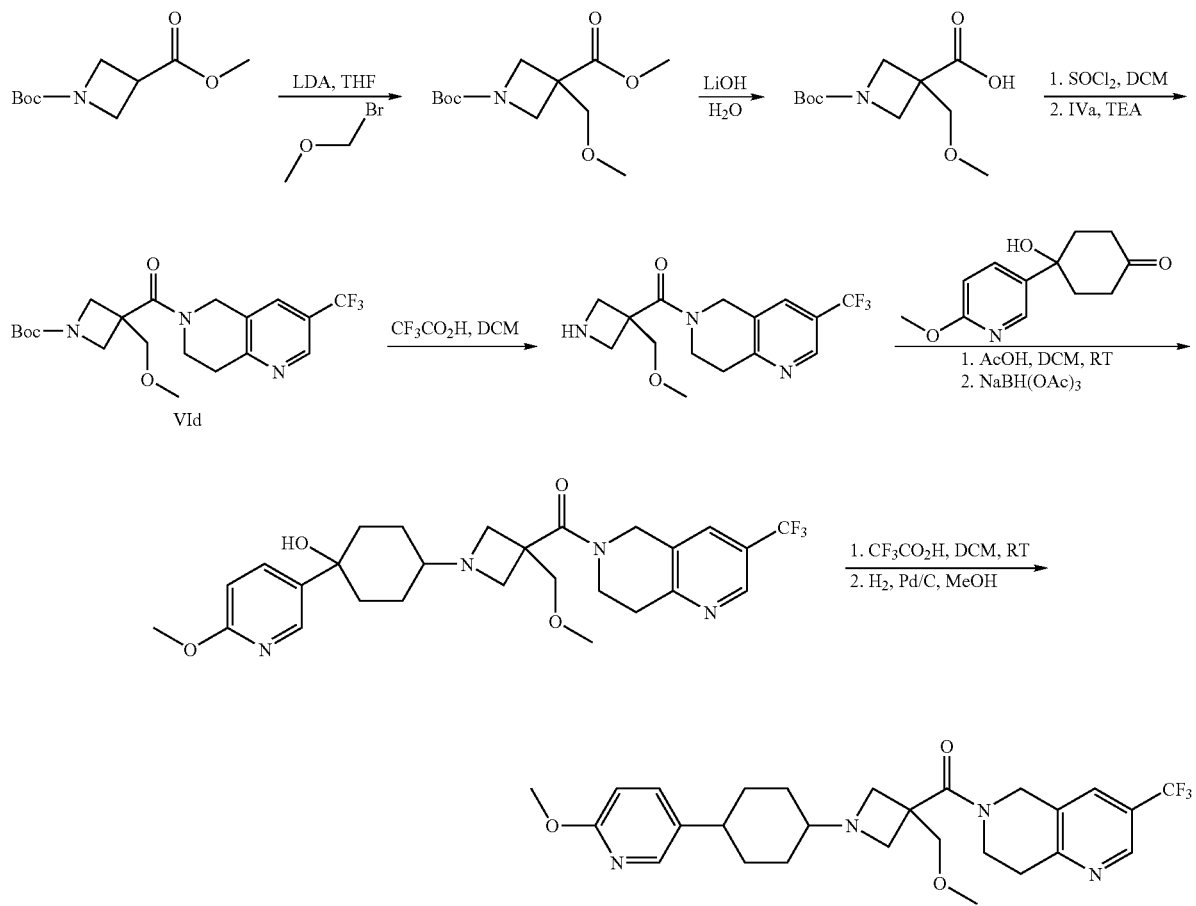

EXPERIMENTAL SECTION

Provided below are representative procedures for making compounds encompassed by formulae Ia and Ib:

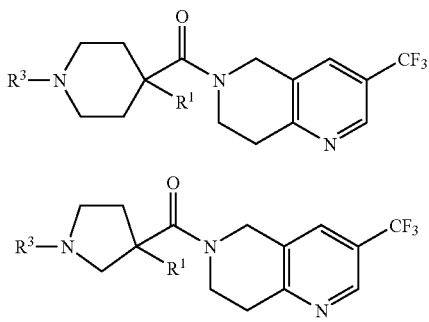

A: General Procedure of Alkylation of Ester (Step 1 of Scheme 1 or Scheme 2)

To a solution of Boc-protected piperidine-4-carboxylate or pyrrolidine-3-carboxylate (1 eq.) cooled at −78° C. in tetrahydrofuran (THF) was added a solution of freshly prepared lithium diisopropylamide (LDA) (1 eq.). The solution was allowed to stir at −78° C. for 15 min and at 0° C. for 45 min. The appropriate alkyl halide was added and stirring was continued overnight. The crude product was purified by silica chromatography on an ISCO system (5-10% EtOAc/hexanes) to collect compounds of formula IIa or IIb in 50-75% yield.

B: General Procedure of Saponification (Step 2 of Scheme 1 or Scheme 2)

Ester IIa or IIb (1 eq.) was heated with LiOH or KOH (10 eq.) in a mixture of MeOH/H$_2$O/THF (2.5/2.5/1.0) at 90° C. for 2-16 h. The solvent was removed under vacuum. The residue was washed with ethyl acetate to remove unreacted ester. The separated aqueous layer was acidified to pH 4 with 1M HCl, and then extracted with ethyl acetate (×3). The product of formula IIIa or IIIb was collected after solvent removal and/or purification by silica chromatography in 5% MeOH/DCM.

C: General Procedure for Amide Formation (Step 1 and 2 in Scheme 4 and 5)

To acid IIa or IIb (1 eq.) in dichloromethane (DCM) was added 2M oxalyl chloride or SOCl$_2$ in DCM solution (3 eq.) and a few drops of dimethylformamide (DMF). The mixture was stirred at RT for 2 h and concentrated to under reduced pressure. The product was added to a solution of IVa (1 eq.) in DCM and triethyl amine (2.6 eq.) at 0° C. The mixture was stirred at 0° C. for 1 h, diluted with DCM and washed with sodium bicarbonate solution and water. The solution was dried over sodium sulfate and purified by silica chromatography to collect the desired product.

D: General Procedure for Removal of Boc Group (Step 4 of Scheme 1 or Scheme 2)

Boc-protected amine Va or Vb (1 eq.) was stirred in DCM at 0° C. and trifluoroacetic acid (TFA) was added slowly. The ice bath was immediately removed after the addition of trifluoracetic acid (TFA). The resulting solution was stirred at room temperature for 1.5 h then a small amount of isopropyl alcohol was added. Concentration of the solution under reduced pressure gave the unprotected amine VIa or VIb as the trifluororacetic acid salt, which was used without further purification in the next step. Compound VIa or VIb can be converted to a free base through a standard basic work-up (sodium bicarbonate solution).

E: General Procedure for Reductive Amination (Step 5 of Scheme 1 or Scheme 2)

A mixture of aldehyde or ketone VII (1 eq.), acetic acid (1.5 eq.) and amine VI (1.2-1.5 eq.) in DCM/MeOH (1:2) was stirred at room temperature for 1 h. Sodium triacetoxyborohydride (2-3 eq.) was added and the reaction mixture was stirred for 16 h at room temperature. After concentration of solvent under reduced pressure, the resulting residue was dissolved in ethyl acetate, then washed with water and brine. The organic extract was dried, filtered and concentrated. The crude product was purified either by silica chromatography on an ISCO system or by reverse phase preparative HPLC to yield the desired final product I with purity greater than 95%.

F: General Procedure of Alkylation with Alkyl or Benzyl Halides (Step 5 of Scheme 1 or Scheme 2)

A mixture of piperidine or pyrrolidine intermediate VI (1 eq.), alkyl/benzyl halide VIII (1.2 eq.), diisopropylethylamine (1.5 eq.) and potassium carbonate (2.5 eq.) in DMF was irradiated in a microwave instrument at 110° C. for ~20-30 min (Personal Chemistry Emrys™ Optimizer microwave reactor). The reaction mixture was cooled and diluted with ethyl acetate. The combined organic layers were washed with brine (×3), then dried over sodium sulfate, filtered and concentrated under reduced pressure. The crude product was purified either by column chromatography on ISCO system (the final product as free base) or by reverse phase preparative HPLC to yield the desired final product I as trifluoroacetic salt with purity greater than 95%.

G: General Procedure of Benzylic Bromination (Scheme 3)

To a solution of 1,7-dimethylquinolin-2(1H)-one (5 eq.) in 20 mL of CCl$_4$ were added azobis(isobutyronitrile) (AIBN) (1 eq.) and N-bromosuccinamide (1 eq.). The solution was stirred at 80° C. for 6 h. The product was extracted with DCM, washed with water and dried over sodium sulfate. The product was evaporated to dryness and purified by silica chromatography to give the desired product.

H: General Procedure for Reductive Amination (Step 4 of Scheme 6)

To VIc (1 eq.), appropriate ketone (1 eq.) and Ti(OiPr)$_4$ (1.25 eq.) in THF were irradiated in a Microwave instrument at 100° C. for 30 min (Personal Chemistry Emrys™ Optimizer microwave reactor). The reaction mixture was cooled and NaBH(OAc)$_3$ (3 eq.) added. The mixture was stirred at room temperature overnight. The solvent was removed in vacuo. The residue was dissolved in ethyl acetate and washed with sat. sodium bicarbonate. The organic layer was washed with brine, then dried over sodium sulfate, filtered and concentrated under reduced pressure. The crude product was purified by reverse phase preparative HPLC to yield the desired final product as trifluoroacetic salt with purity greater than 95%

Intermediate IIb 1-t-Butyl 3-methyl 3-(cyclopropylmethyl)pyrrolidine-1,3-dicarboxylate

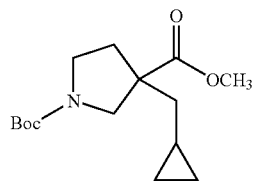 [SMILES: COC(=O)C1(CC2CC2)CCN(C(=O)OC(C)(C)C)C1]

The title compound was prepared according to general procedure A described in connection with Scheme 2. $^1$H NMR (400 MHz, CDCl$_3$): δ 3.93-3.77 (m, 1H), 3.72 (s, 3H), 3.45-3.22 (m, 3H), 2.45-2.32 (m, 1H), 1.89-1.79 (m, 1H), 1.65-1.59 (m, 2H), 1.48 (s, 9H), 0.67-0.57 (m, 1H), 0.48-0.42 (m, 2H), 0.06-0.01 (m, 2H); MS (ESI) m/z: Calculated for C$_{15}$H$_{25}$NO$_4$: 283.2. found: 306 (M+Na)$^+$.

Intermediate IIIb 1-(t-Butoxycarbonyl)-3-(cyclopropylmethyl)pyrrolidine-3-carboxylic acid

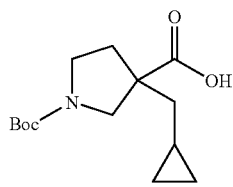

The title compound was prepared according to general procedure B described in connection with Scheme 2. 1-t-Butyl 3-methyl 3-(cyclopropylmethyl)pyrrolidine-1,3-dicarboxylate (1.00 g, 3.5 mmol.) was dissolved in 2 mL MeOH and a solution KOH (0.59 g, 10.6 mmol.) in 2 mL H$_2$O was added. The reaction mixture was microwaved at 130° C. for 30 min. The methanol was evaporated and 10 mL of 10% KHSO$_4$ solution was added to the residue. The acid was extracted with EtOAc (2×20 mL). The combined organic fractions were dried over Na$_2$SO$_4$; evaporation of solvent gave 0.98 g of the desired product as orange oil which crystallized on standing (quantitative yield). $^1$H NMR (400 MHz, CDCl$_3$): δ 3.81-3.93 (m, 1H), 3.36-3.44 (m, 2H), 2.28 (d, 1H), 2.33-2.46 (m, 1H), 1.83-1.91 (m, 1H), 1.60-1.70 (m, 2H), 1.45 (s, 9H), 0.62-0.75 (m, 1H), 0.42-0.50 (m, 2H), 0.05-0.12 (m, 2H); MS (ESI) m/z: Calculated for C$_{14}$H$_{23}$NO$_4$: 269.2. found: 292 (M+Na)$^+$.

Intermediate Vb tert-butyl 3-(cyclopropylmethyl)-3-(3-(trifluoromethyl)-5,6,7,8-tetrahydro-1,6-naphthyridine-6-carbonyl)pyrrolidine-1-carboxylate

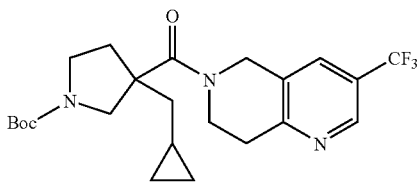 [SMILES: CC(C)(C)OC(=O)N1CCC(CC2CC2)(C(=O)N2CCc3ncc(C(F)(F)F)cc3C2)C1]

The title compound was prepared according to general procedure C described in connection with Scheme 5. To a solution of 1-(t-butoxycarbonyl)-3-(cyclopropylmethyl)pyrrolidine-3-carboxylic acid IIIb (300 mg, 1.11 mmol) in 16 mL of CH$_2$Cl$_2$ was added thionyl chloride (0.24 mL, 3.34 mmol) and two drops of DMF. The mixture was stirred for ~1-2 h at room temperature. After removal of solvent, the residue was redissolved in CH$_2$Cl$_2$ (13 mL), followed by the addition of 3-(trifluoromethyl)-5,6,7,8-tetrahydro-1,6-naphthyridine hydrochloride (IVa) (320 mg, 1.16 mmol) and triethyl amine (0.78 mL, 5.5 mmol). LC-MS analysis indicated the completion of the reaction after one hour stirring at RT. The mixture was washed with water (×2) and brine (×3). After concentration of solvent, the crude residue was purified by flash chromatography on silica gel to give 300 mg (60% yield) of the desired product. MS (ESI) m/z: Calculated for C$_{23}$H$_{30}$F$_3$N$_3$O$_3$: 453.2. found: 453.7 (M+Na)$^+$.

Intermediate VIb (3-(Cyclopropylmethyl)pyrrolidin-3-yl)(3-(trifluoromethyl)-7,8-dihydro-1,6-naphthyridin-6(5H)-yl)methanone

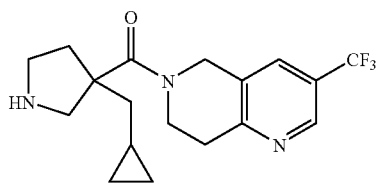 [SMILES: O=C(N1CCc2ncc(C(F)(F)F)cc2C1)C1(CC2CC2)CCNC1]

The title compound was prepared according to general procedure D described in connection with Scheme 5. tert-Butyl 3-(cyclopropylmethyl)-3-(3-(trifluoromethyl)-5,6,7,8-tetrahydro-1,6-naphthyridine-6-carbonyl)pyrrolidine-1-carboxylate was dissolved in 8 mL of CH$_2$Cl$_2$ and 2 mL of TFA was then added to the solution at RT. The reaction mixture was stirred for 4 h and the solvent was evaporated. The desired product was obtained as TFA salt without further application for next step. $^1$H NMR (400 MHz, CDCl$_3$): δ 8.78 (s, 1H), 7.82-7.78 (m, 1H), 6.86 (br s, 1H), 4.88 (dd, 2H), 3.98 (m, 3H), 3.42 (d, 1H), 3.33 (m, 1H), 3.22 (br s, 2H), 2.63 (m, 1H), 2.20 (m, 1H), 2.01-1.73 (m, 3H), 0.68 (s, 1H), 0.53 (br s, 2H), 0.066 (m, 2H); MS (ESI) m/z: Calculated for C$_{18}$H$_{22}$F$_3$N$_3$O: 353.2. found 354.1 (M+H)$^+$.

Intermediate VIIIa 7-(Bromomethyl)-1-methylquinolin-2(1H)-one

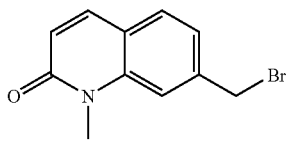

The title compound was prepared according to general procedure G described in connection with Scheme 3. 7-Methylquinoline (3 g, 20.95 mmol) was dissolved in 20 mL methyliodide and stirred for 3 h at RT. The reaction mixture was dissolved in 30 mL of acetonitrile and KMnO$_4$ (6.62 g, 41.90 mmol) was added portionwise. The reaction mixture was stirred for 1 h while violet changed to brown color. Saturated solution of sodium metabisulfite solution was carefully added. Then 10% HCl was added and extracted with dichloromethane. The solvent was dried over Na$_2$SO$_4$ and evaporated by rotary evaporator. The crude product was purified by ISCO flash chromatography (1-4% CH$_2$Cl$_2$/CH$_3$OH)) to yield 2.75 g (76%) of pure product. $^1$H NMR (400 MHz, CDCl$_3$): δ 7.63 (d, 1H), 7.43 (d, 1H), 7.20 (s, 1H), 7.12 (d, 1H), 6.61 (d, 1H), 3.75 (s, 3H), 2.57 (s, 3H); MS (ESI) m/z: Calculated for $C_{11}H_{11}NO$: 173.21. found: 173.2 (M)$^+$.

To a solution of 1,7-dimethylquinolin-2(1H)-one (1.2 g, 6.92 mmol) in 20 mL of $CCl_4$ were added AIBN (0.227 g, 1.38 mmol) and N-bromosuccinamide (1.23 g, 6.92 mmol). The solution was stirred at 80° C. for 6 h. The product was extracted with dichloromethane and washed with water and dried over $Na_2SO_4$. The product was evaporated to dryness and purified by ISCO system (1-4% $CH_2Cl_2/CH_3OH$) to give 1.25 g (72%). $^1$H NMR (400 MHz, $CDCl_3$): δ 7.64 (d, 1H), 7.53 (d, 1H), 7.38 (s, 1H), 7.27 (d, 1H), 6.73 (d, 1H), 4.60 (s, 2H), 3.73 (s, 3H); MS (ESI) m/z: Calculated for $C_{11}H_{10}BrNO$: 252.11. found: 252.1 (M)$^+$.

A series of compounds were synthesized based on the procedures described above. The structures and MS-characteristics, if available, of the compounds are summarized in Table 1:

TABLE 1

| Example No. | Structure | m/z | Calc MW | Synthetic Methods |
|---|---|---|---|---|
| 1 | 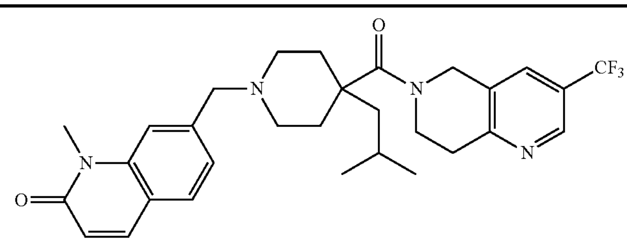 | 541.2 | 540.3 | Scheme 4 |
| 2 | 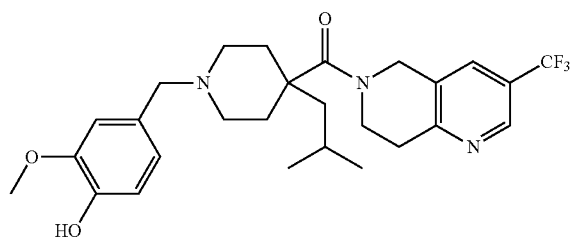 [SMILES: COc1cc(CN2CCC(CC(C)C)(C(=O)N3CCc4ncc(C(F)(F)F)cc4C3)CC2)ccc1O] | 506.1 | 505.3 | Scheme 4 |
| 3 | 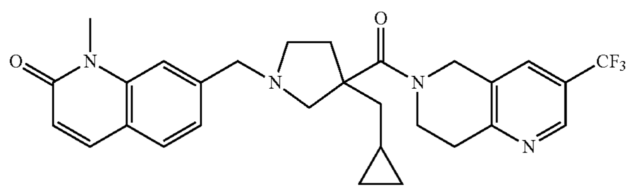 [SMILES: Cn1c(=O)ccc2ccc(CN3CCC(CC4CC4)(C(=O)N4CCc5ncc(C(F)(F)F)cc5C4)C3)cc21] | 525.2 | 524.2 | Scheme 5 |
| 4, 5 | (Enantiomer I) | 525.2 | 524.2 | Scheme 5 |
| 4, 5 | (Enantiomer II) | 525.2 | 524.2 | Scheme 5 |
| 6 | 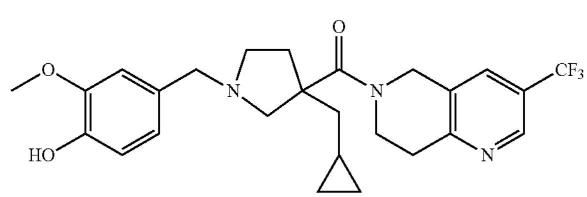 [SMILES: COc1cc(CN2CCC(CC3CC3)(C(=O)N3CCc4ncc(C(F)(F)F)cc4C3)C2)ccc1O] | 490.1 | 489.2 | Scheme 5 |

TABLE 1-continued
| Example No. | Structure | m/z | Calc MW | Synthetic Methods |
|---|---|---|---|---|
| 7 | 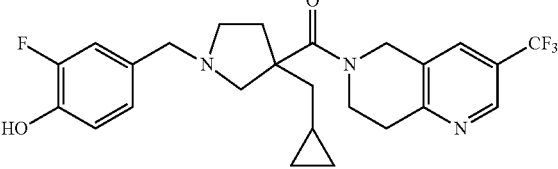 | 478.1 | 477.2 | Scheme 5 |
| 8 | 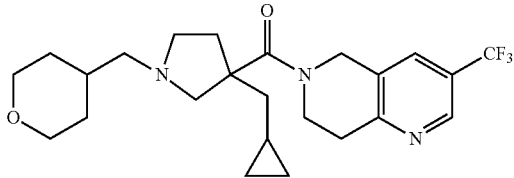 [SMILES: O=C(N1CCc2ncc(C(F)(F)F)cc2C1)C1(CC2CC2)CCN(CC2CCOCC2)C1] | 452.2 | 451.2 | Scheme 5 |
| 9 | 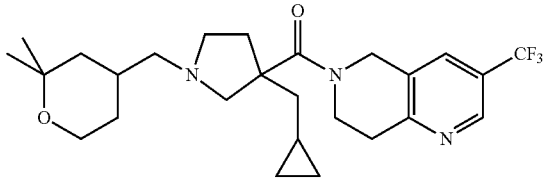 [SMILES: CC1(C)CC(CN2CCC(CC3CC3)(C(=O)N3CCc4ncc(C(F)(F)F)cc4C3)C2)CCO1] | 480.2 | 479.3 | Scheme 5 |
| 10 | 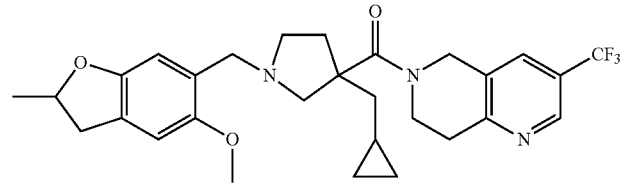 [SMILES: COc1cc2c(cc1CN1CCC(CC3CC3)(C(=O)N3CCc4ncc(C(F)(F)F)cc4C3)C1)OC(C)C2] | 530.2 | 529.3 | Scheme 5 |
| 11 | 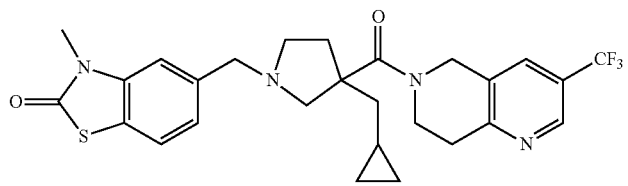 | 531.1 | 530.2 | Scheme 5 |
| 12 | 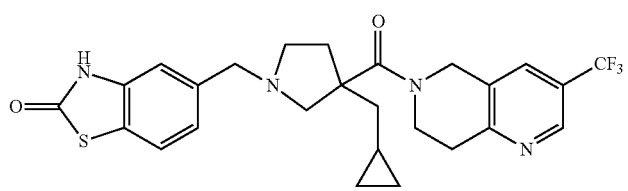 [SMILES: O=C(N1CCc2ncc(C(F)(F)F)cc2C1)C1(CC2CC2)CCN(Cc2ccc3sc(=O)[nH]c3c2)C1] | 517.1 | 516.2 | Scheme 7 |
| 13 | 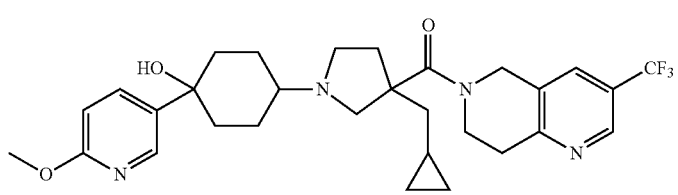 [SMILES: COc1ccc(C2(O)CCC(N3CCC(CC4CC4)(C(=O)N4CCc5ncc(C(F)(F)F)cc5C4)C3)CC2)cn1] | 559.2 | 558.3 | Scheme 5 |
| 14 | 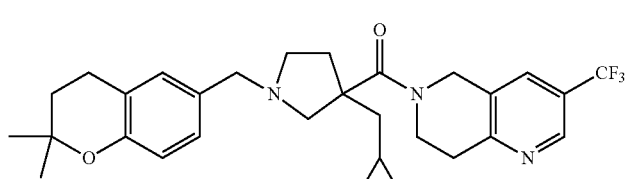 | 528.1 | 527.3 | Scheme 5 |

TABLE 1-continued
| Example No. | Structure | m/z | Calc MW | Synthetic Methods |
|---|---|---|---|---|
| 15 | 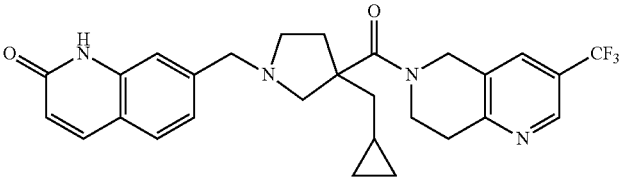 [SMILES: O=C(N1CCc2ncc(C(F)(F)F)cc2C1)C1(CC2CC2)CCN(Cc2ccc3ccc(=O)[nH]c3c2)C1] | 511.2 | 510.2 | Scheme 7 |
| 16 | 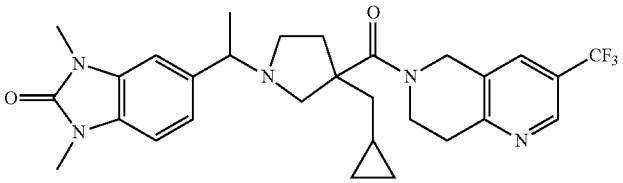 [SMILES: CC(c1ccc2c(c1)n(C)c(=O)n2C)N1CCC(CC2CC2)(C(=O)N2CCc3ncc(C(F)(F)F)cc3C2)C1] | 542.4 | 541.3 | Scheme 6 |
| 17 | 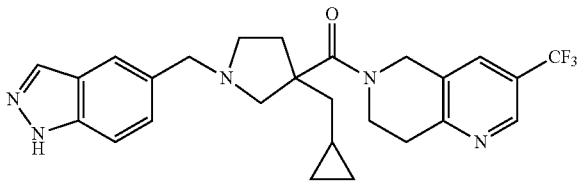 [SMILES: O=C(N1CCc2ncc(C(F)(F)F)cc2C1)C1(CC2CC2)CCN(Cc2ccc3[nH]ncc3c2)C1] | 484 | 483.2 | Scheme 5 |
| 18 | 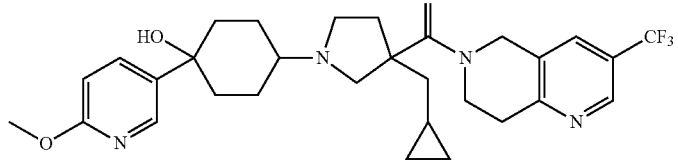 | 559 | 558.3 | Scheme 8 |
| 19 | 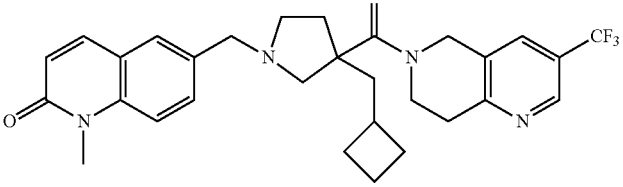 | 539.4 | 538.3 | Scheme 5 |
| 20 | 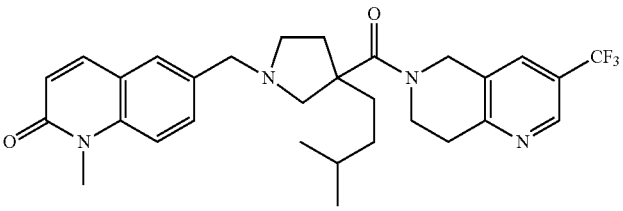 [SMILES: CC(C)CCC1(C(=O)N2CCc3ncc(C(F)(F)F)cc3C2)CCN(Cc2ccc3c(ccc(=O)n3C)c2)C1] | 541.4 | 540.3 | Scheme 5 |
| 21 | 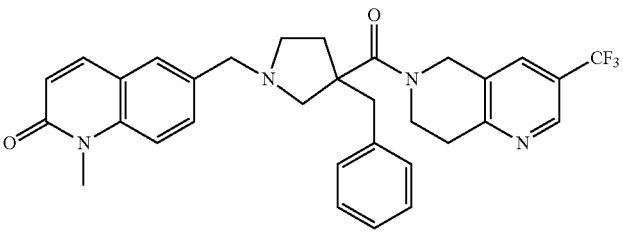 [SMILES: Cn1c(=O)ccc2cc(CN3CCC(Cc4ccccc4)(C(=O)N4CCc5ncc(C(F)(F)F)cc5C4)C3)ccc21] | 561.3 | 560.2 | Scheme 5 |

TABLE 1-continued

| Example No. | Structure | m/z | Calc MW | Synthetic Methods |
|---|---|---|---|---|
| 22 | 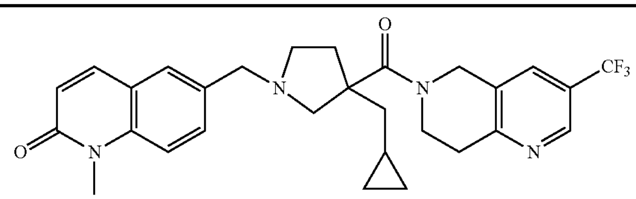 | 525.1 | 524.2 | Scheme 5 |
| 23 | 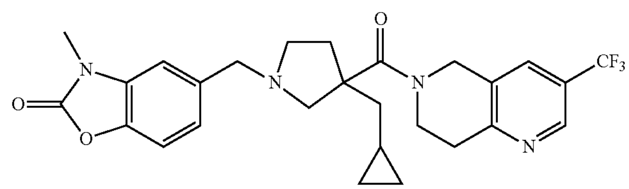 [SMILES: Cn1c(=O)oc2ccc(CN3CCC(CC4CC4)(C(=O)N4CCc5ncc(C(F)(F)F)cc5C4)C3)cc21] | 515.1 | 514.2 | Scheme 5 |
| 24 | 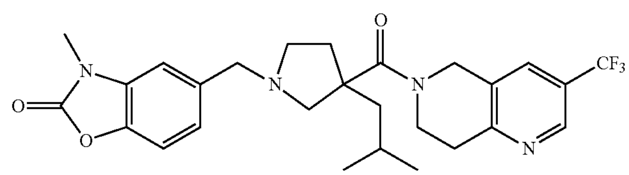 [SMILES: CC(C)CC1(C(=O)N2CCc3ncc(C(F)(F)F)cc3C2)CCN(Cc2ccc3oc(=O)n(C)c3c2)C1] | 517.2 | 516.2 | Scheme 5 |
| 25 | 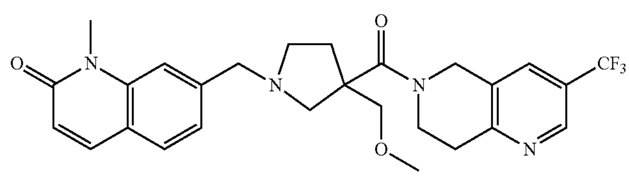 [SMILES: COCC1(C(=O)N2CCc3ncc(C(F)(F)F)cc3C2)CCN(Cc2ccc3ccc(=O)n(C)c3c2)C1] | 515 | 514.2 | Scheme 5 |
| 26, 27 (Enantiomer I) | | 515 | 514.2 | Scheme 5 |
| 26, 27 (Enantiomer II) | | 515 | 514.2 | Scheme 5 |
| 28 | 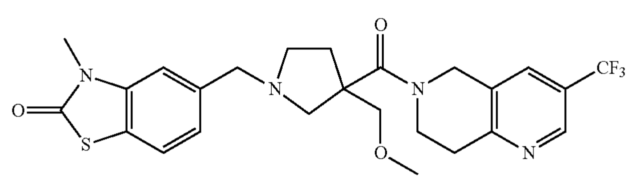 [SMILES: COCC1(C(=O)N2CCc3ncc(C(F)(F)F)cc3C2)CCN(Cc2ccc3sc(=O)n(C)c3c2)C1] | 521.1 | 520.2 | Scheme 5 |
| 29 | 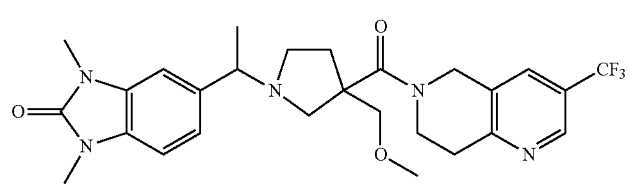 [SMILES: COCC1(C(=O)N2CCc3ncc(C(F)(F)F)cc3C2)CCN(C(C)c2ccc3c(c2)n(C)c(=O)n3C)C1] | 532.0 | 531.3 | Scheme 6 |

TABLE 1-continued

| Example No. | Structure | m/z | Calc MW | Synthetic Methods |
|---|---|---|---|---|
| 30, 31 | (Isomer A) | 549.2 | 548.3 | Scheme 8 |
| 30, 31 | (Isomer B) | 549.2 | 548.3 | Scheme 8 |
| 32 | 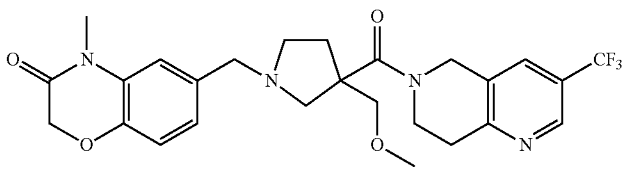 [SMILES: COCC1(C(=O)N2CCc3ncc(C(F)(F)F)cc3C2)CCN(Cc2ccc3c(c2)N(C)C(=O)CO3)C1] | 519.3 | 518.2 | Scheme 5 |
| 33 | 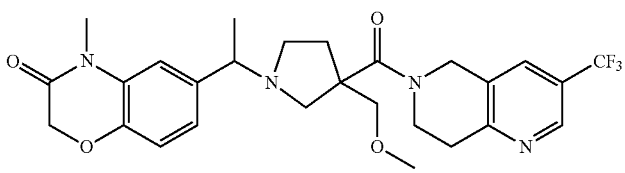 [SMILES: COCC1(C(=O)N2CCc3ncc(C(F)(F)F)cc3C2)CCN(C(C)c2ccc3c(c2)N(C)C(=O)CO3)C1] | 533.2 | 532.2 | Scheme 6 |
| 34 | 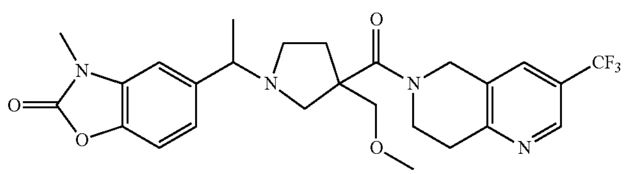 [SMILES: COCC1(C(=O)N2CCc3ncc(C(F)(F)F)cc3C2)CCN(C(C)c2ccc3oc(=O)n(C)c3c2)C1] | 519.2 | 518.2 | Scheme 6 |
| 35 | 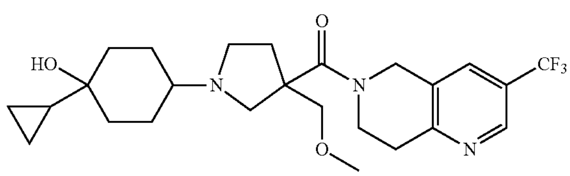 [SMILES: COCC1(C(=O)N2CCc3ncc(C(F)(F)F)cc3C2)CCN(C2CCC(O)(C3CC3)CC2)C1] | 482.2 | 481.3 | Scheme 8 |
| 36 | 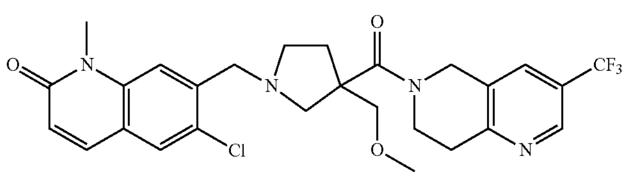 [SMILES: COCC1(C(=O)N2CCc3ncc(C(F)(F)F)cc3C2)CCN(Cc2cc3c(ccc(=O)n3C)cc2Cl)C1] | 549 | 548.2 | Scheme 5 |
| 37 | 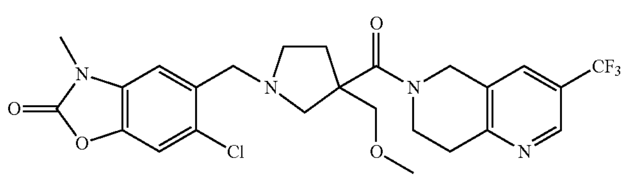 [SMILES: COCC1(C(=O)N2CCc3ncc(C(F)(F)F)cc3C2)CCN(Cc2cc3c(cc2Cl)oc(=O)n3C)C1] | 539 | 538.2 | Scheme 5 |

TABLE 1-continued

| Example No. | Structure | m/z | Calc MW | Synthetic Methods |
|---|---|---|---|---|
| 38 | 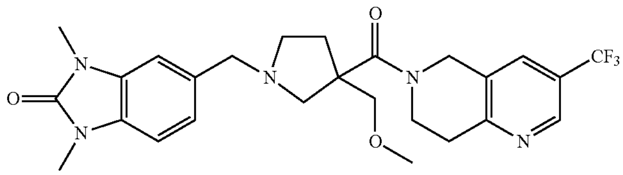 [SMILES: COCC1(C(=O)N2CCc3ncc(C(F)(F)F)cc3C2)CCN(Cc2ccc3c(c2)n(C)c(=O)n3C)C1] | 518 | 517.2 | Scheme 5 |
| 39 | 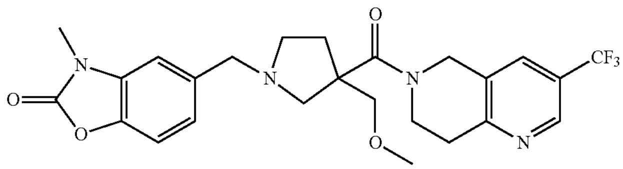 [SMILES: COCC1(C(=O)N2CCc3ncc(C(F)(F)F)cc3C2)CCN(Cc2ccc3oc(=O)n(C)c3c2)C1] | 505.1 | 504.2 | Scheme 5 |
| 40, 41 | (Enantiomer I) | 505.1 | 504.2 | Scheme 5 |
| 40, 41 | (Enantiomer II) | 505.1 | 504.2 | Scheme 5 |
| 42 | 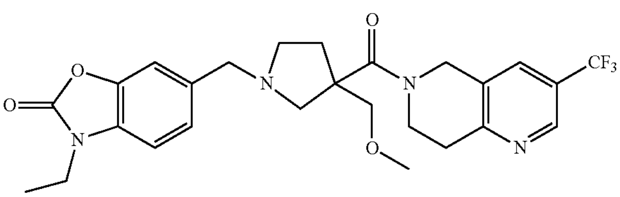 [SMILES: CCn1c(=O)oc2cc(CN3CCC(COC)(C(=O)N4CCc5ncc(C(F)(F)F)cc5C4)C3)ccc21] | 519.2 | 518.2 | Scheme 5 |
| 43 | 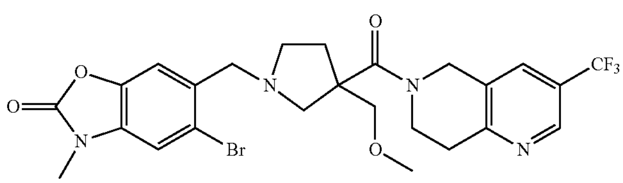 [SMILES: COCC1(C(=O)N2CCc3ncc(C(F)(F)F)cc3C2)CCN(Cc2cc3oc(=O)n(C)c3cc2Br)C1] | 583.2 | 582.11 | Scheme 5 |
| 44 | 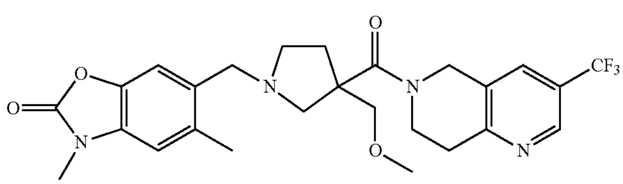 [SMILES: COCC1(C(=O)N2CCc3ncc(C(F)(F)F)cc3C2)CCN(Cc2cc3oc(=O)n(C)c3cc2C)C1] | 519.2 | 518.2 | Scheme 5 |
| 45 | 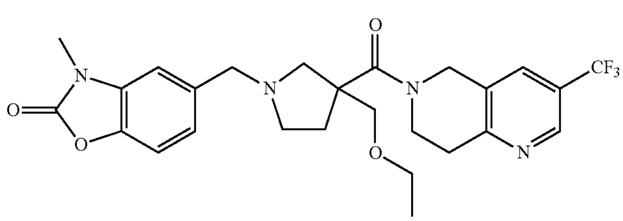 [SMILES: CCOCC1(C(=O)N2CCc3ncc(C(F)(F)F)cc3C2)CCN(Cc2ccc3oc(=O)n(C)c3c2)C1] | 519.2 | 518.53 | Scheme 5 |

TABLE 1-continued

| Example No. | Structure | m/z | Calc MW | Synthetic Methods |
|---|---|---|---|---|
| 46 | 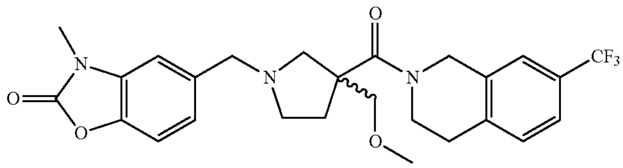 [SMILES: COCC1(C(=O)N2CCc3ccc(C(F)(F)F)cc3C2)CCN(Cc2ccc3oc(=O)n(C)c3c2)C1] | 504.2 | 503.51 | Scheme 5 |
| 47 | 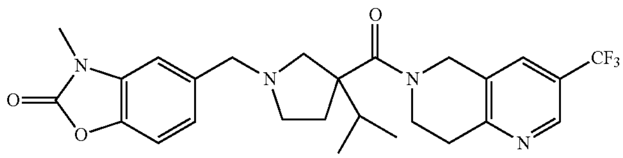 [SMILES: CC(C)C1(C(=O)N2CCc3ncc(C(F)(F)F)cc3C2)CCN(Cc2ccc3oc(=O)n(C)c3c2)C1] | 503.1 | 502.53 | Scheme 5 |
| 48 | 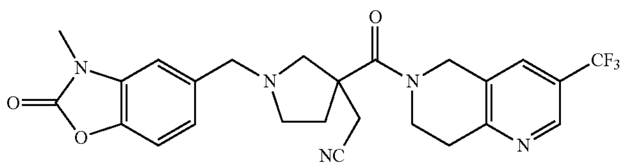 [SMILES: Cn1c(=O)oc2ccc(CN3CCC(CC#N)(C(=O)N4CCc5ncc(C(F)(F)F)cc5C4)C3)cc21] | 500.3 | 499.48 | Scheme 5 |
| 49 | 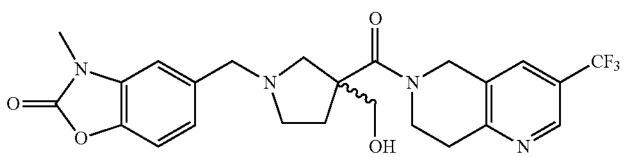 [SMILES: Cn1c(=O)oc2ccc(CN3CCC(CO)(C(=O)N4CCc5ncc(C(F)(F)F)cc5C4)C3)cc21] | 491.2 | 490.47 | Scheme 5 |
| 50, 51 (Isomer I) | 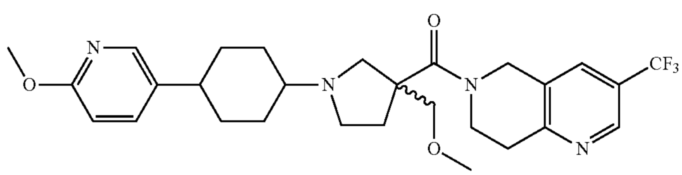 [SMILES: COCC1(C(=O)N2CCc3ncc(C(F)(F)F)cc3C2)CCN(C2CCC(c3ccc(OC)nc3)CC2)C1] | 533.2 | 532.60 | Scheme 8 |
| 50, 51 (Isomer II) | 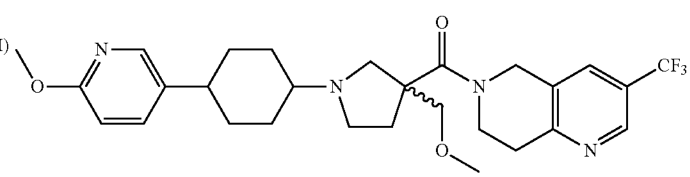 | 533.2 | 532.60 | Scheme 8 |
| 52, 53 (Isomer II) | | 520.2 | 519.26 | Scheme 8 |
| 52, 53 (Isomer II) | | 520.2 | 519.26 | Scheme 8 |
| 54, 55 (Isomer II) | 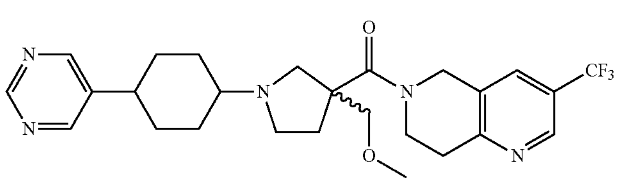 [SMILES: COCC1(C(=O)N2CCc3ncc(C(F)(F)F)cc3C2)CCN(C2CCC(c3cncnc3)CC2)C1] | 504.3 | 503.55 | Scheme 8 |

TABLE 1-continued

| Example No. | Structure | m/z | Calc MW | Synthetic Methods |
|---|---|---|---|---|
| 54, 55 (Isomer II) | 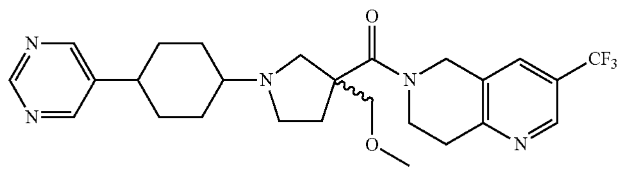 [SMILES: COCC1(C(=O)N2CCc3ncc(C(F)(F)F)cc3C2)CCN(C2CCC(c3cncnc3)CC2)C1] | 504.3 | 503.55 | Scheme 8 |
| 56, 57 (Isomer I) | 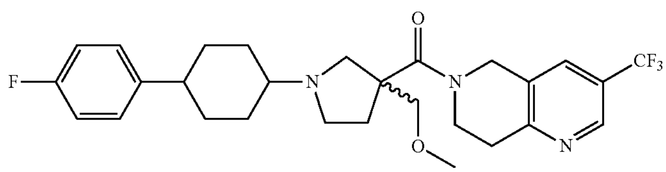 | 520.2 | 519.57 | Scheme 9 |
| 56, 57 (Isomer II) | 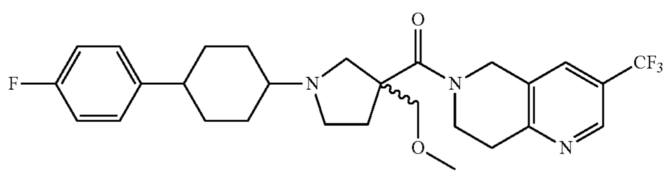 [SMILES: COCC1(C(=O)N2CCc3ncc(C(F)(F)F)cc3C2)CCN(C2CCC(c3ccc(F)cc3)CC2)C1] | 520.2 | 519.57 | Scheme 9 |
| 58 | 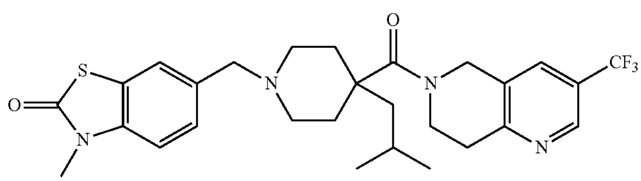 [SMILES: CC(C)CC1(C(=O)N2CCc3ncc(C(F)(F)F)cc3C2)CCN(Cc2ccc3c(c2)sc(=O)n3C)CC1] | 547.0 | 546.65 | Scheme 4 |
| 59 | 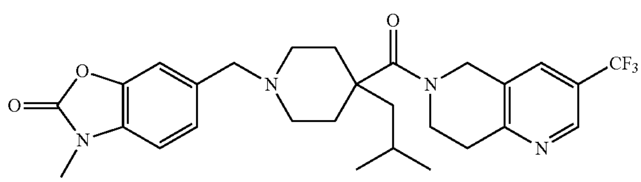 [SMILES: CC(C)CC1(C(=O)N2CCc3ncc(C(F)(F)F)cc3C2)CCN(Cc2ccc3c(c2)oc(=O)n3C)CC1] | 531.2 | 530.58 | Scheme 4 |
| — | | — | — | Scheme 5 |
| — | | — | — | Scheme 5 |
| — | | — | — | Scheme 5 |

TABLE 1-continued
| Example No. | Structure | m/z | Calc MW | Synthetic Methods |
|---|---|---|---|---|
| — | 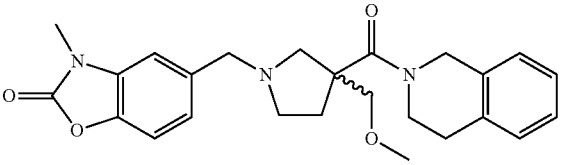 [SMILES: COCC1(C(=O)N2CCc3ccccc3C2)CCN(Cc2ccc3oc(=O)n(C)c3c2)C1] | — | — | Scheme 5 |
| — | 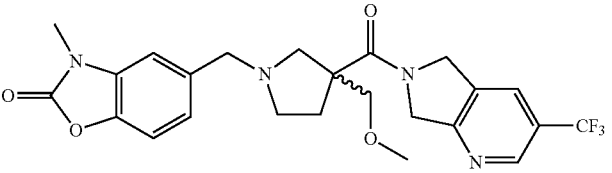 [SMILES: COCC1(C(=O)N2Cc3cc(C(F)(F)F)cnc3C2)CCN(Cc2ccc3oc(=O)n(C)c3c2)C1] | — | — | Scheme 5 |
| — | 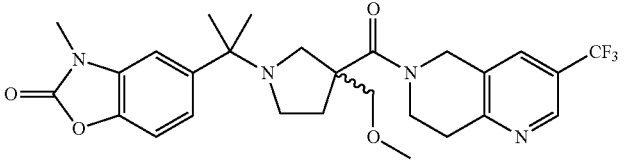 [SMILES: COCC1(C(=O)N2CCc3ncc(C(F)(F)F)cc3C2)CCN(C(C)(C)c2ccc3oc(=O)n(C)c3c2)C1] | — | — | Scheme 6 |
| — | 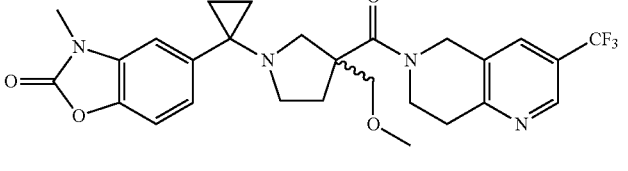 | — | — | Scheme 6 |
| — | 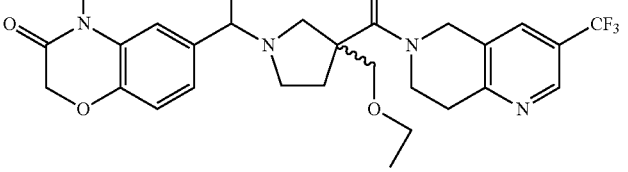 | — | — | Scheme 6 |
| — | 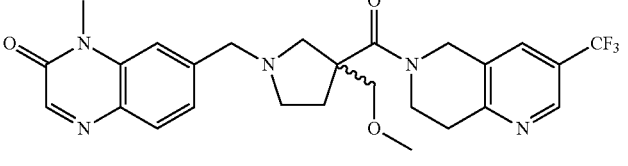 | — | — | Scheme 5 |
| — | 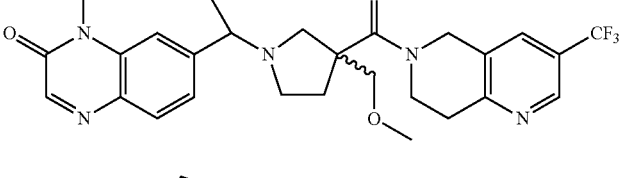 | — | — | Scheme 6 |
| — | 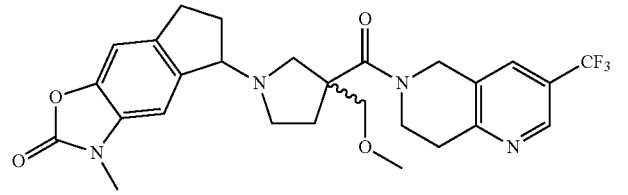 [SMILES: COCC1(C(=O)N2CCc3ncc(C(F)(F)F)cc3C2)CCN(C2CCc3cc4oc(=O)n(C)c4cc32)C1] | — | — | Scheme 5 |

TABLE 1-continued

| Example No. | Structure | m/z | Calc MW | Synthetic Methods |
|---|---|---|---|---|
| — | | — | — | Scheme 5 |
| — | | — | — | Scheme 5 |
| — | | — | — | Scheme 6 |
| — | | — | — | Scheme 8 |
| — | | — | — | Scheme 8 |
| — | | — | — | Scheme 8 |
| — | | — | — | Scheme 8 |
| — | | — | — | Scheme 10 |

TABLE 1-continued

| Example No. | Structure | m/z | Calc MW | Synthetic Methods |
|---|---|---|---|---|
| — | | — | — | Scheme 10 |
| — | | — | — | Scheme 10 |
| — | | — | — | Scheme 10 |

Example 1

7-((4-Isobutyl-4-(3-(trifluoromethyl)-5,6,7,8-tetrahydro-1,6-naphthyridine-6-carbonyl)piperidin-1-yl)methyl)-1-methylquinolin-2(1H)-one

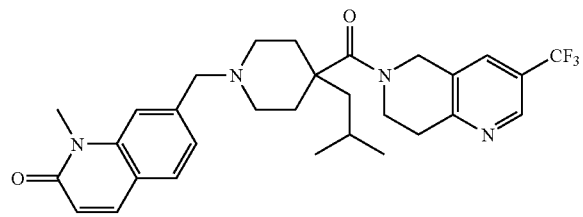 [SMILES: CC(C)CC1(C(=O)N2CCc3ncc(C(F)(F)F)cc3C2)CCN(Cc2ccc3ccc(=O)n(C)c3c2)CC1]

The title compound was prepared according to the general procedures described in Scheme 4: a mixture of (4-isobutylpiperidin-4-yl)(3-(trifluoromethyl)-7,8-dihydro-1,6-naphthyridin-6(5H)-yl)methanone VIa (56 mg, 0.094 mmol), intermediate VIIIa (25 mg, 0.098 mmol), diisopropylethylamine (70 μL, 0.39 mmol) and potassium carbonate (33 mg, 0.235 mmol) in DMF (2 mL) was irradiated in a Microwave instrument at 110° C. for 30 min (Personal Chemistry Emrys™ Optimizer microwave reactor). The reaction mixture was cooled and diluted with ethyl acetate. The organic layer was washed with brine (×3), then dried over $Na_2SO_4$, filtered and concentrated under reduced pressure. The crude product was purified by reverse phase preparative HPLC to yield the desired final product as trifluoroacetic salt with purity greater than 95% (36.2 mg, 71% yield): $^1$H NMR (400 MHz, $CD_3OD$): δ 8.72 (br s, 1H), 8.07 (s, 1H), 7.94 (d, 1H), 7.79 (d, 1H), 7.72 (s, 1H), 7.39 (d, 1H), 6.74 (d, 1H), 4.96 (m, 2H), 4.41 (s, 2H), 4.04 (s, 2H), 3.75 (s, 3H), 3.46 (d, 2H), 3.11 (m, 4H), 2.69-2.65 (m, 2H), 1.70 (m, 5H), 0.81 (m, 6H); MS (ESI) m/z: Calculated for $C_{30}H_{35}F_3N_4O_2$: 540.3. found: 541.2 (M+H)$^+$.

Example 2

(1-(4-Hydroxy-3-methoxybenzyl)-4-isobutylpiperidin-4-yl)(3-(trifluoromethyl)-7,8-dihydro-1,6-naphthyridin-6(5H)-yl)methanone

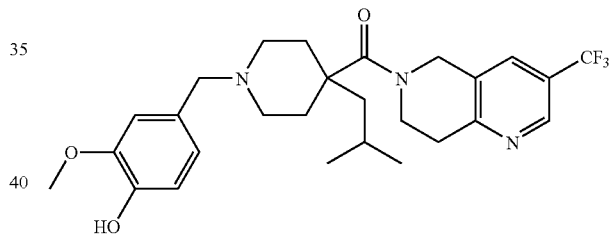

The title compound was prepared according to general procedures described in Scheme 4 (2.0 mg, 4% yield): $^1$H NMR (400 MHz, $CD_3OD$): δ 8.72 (s, 1H), 8.08 (s, 1H), 7.02 (s, 1H), 6.48 (d, 1H), 6.90-6.81 (m, 2H), 4.13 (s, 2H), 4.02 (d, 2H), 3.89 (d, 2H), 3.86 (s, 3H), 3.40 (d, 2H), 3.10 (m, 2H), 3.02 (m, 2H), 2.65 (d, 2H), 1.67 (m, 5H), 0.82 (m, 6H); MS (ESI) m/z: Calculated for $C_{27}H_{34}F_3N_3O_3$: 505.3. found: 506.1 (M+H)$^+$.

Example 3

7-((3-(Cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one

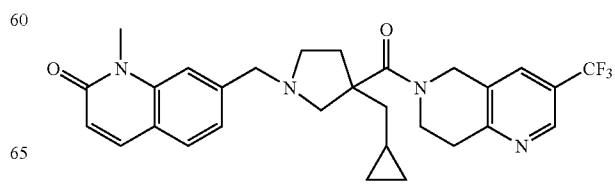

The title compound was prepared according to general procedures described in Scheme 5 (9.1 mg, 39% yield): $^1$H NMR (400 MHz, CD$_3$OD): δ 8.71 (s, 1H), 8.05 (s, 1H), 7.95 (d, 1H), 7.82 (d, 1H), 7.79 (s, 1H), 7.46 (d, 1H), 6.75 (d, 1H), 4.85 (m, 2H), 4.57 (q, 2H), 3.96 (br s, 2H), 3.78 (s, 3H), 3.60 (br s, 1H), 3.44 (br s, 1H), 3.12 (s, 2H), 2.55 (m, 2H), 2.00 (s, 2H), 1.84 (m, 2H), 0.54 (s, 1H), 0.42 (s, 2H), 0.05 (m, 2H); MS (ESI) m/z: Calculated for C$_{29}$H$_{31}$F$_3$N$_4$O$_2$: 524.2. found: 525.2 (M+H)$^+$.

Examples 4 and 5

(S)-7-((3-(Cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one and (R)-7-((3-(cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one

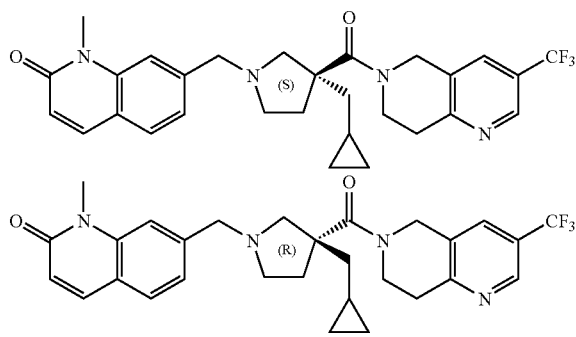

The racemic mixture (ca. 1:1 ratio) was separated into the two enantiomers by normal phase preparative HPLC using a chiral column, yielding enantiomer I (>95% ee; eluented at 4.79 min), and enantiomer II (>95% ee; eluented at 8.03 min).

Example 6

(1-(4-Hydroxy-3-methoxybenzyl)-3-(cyclopropylmethyl)pyrrolidin-3-yl)(3-(trifluoromethyl)-7,8-dihydro-1,6-naphthyridin-6(5H)-yl)methanone

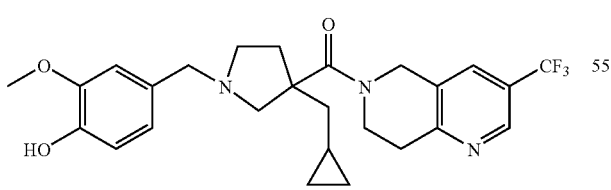

The title compound was prepared according to general procedures described in Scheme 5 (5.6 mg, 7% yield): $^1$H NMR (400 MHz, CD$_3$OD): δ 8.71 (s, 1H), 8.05 (s, 1H), 7.08 (s, 1H), 6.95 (d, 1H), 6.86 (d, 1H), 4.82 (m, 2H), 4.59 (d, 1H), 4.28 (q, 2H), 3.97-3.92 (m, 2H), 3.89 (s, 3H), 3.54 (m, 2H), 3.18-3.12 (m, 3H), 2.49 (m, 2H), 2.00 (m, 1H), 1.80 (dd, 2H), 0.53 (d, 1H), 0.433 (d, 2H), 0.02 (m, 2H); MS (ESI) m/z: Calculated for C$_{26}$H$_{30}$F$_3$N$_3$O$_3$: 489.2. found: 490.1 (M+H)$^+$.

Example 7

(3-(Cyclopropylmethyl)-1-(3-fluoro-4-hydroxybenzyl)pyrrolidin-3-yl)(3-(trifluoromethyl)-7,8-dihydro-1,6-naphthyridin-6(5H)-yl)methanone

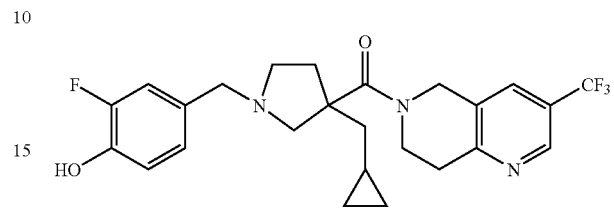

The title compound was prepared according to general procedures described in Scheme 5 (4.0 mg, 5% yield): $^1$H NMR (400 MHz, CD$_3$OD): δ 8.08 (s, 1H), 7.27 (d, 1H), 7.15 (d, 1H), 7.00 (t, 1H), 4.49 (d, 1H), 4.29 (q, 2H), 3.98 (s, 2H), 3.54 (m, 2H), 3.32 (s, 3H), 3.22-3.15 (m, 2H), 2.51 (s, 1H), 1.83 (m, 2H), 1.31 (m, 2H), 0.53-0.44 (m, 3H), 0.05 (m, 2H); MS (ESI) m/z: Calculated for C$_{25}$H$_{27}$F$_4$N$_3$O$_2$: 477.2. found: 478.1 (M+H)$^+$.

Example 8

(3-(Cyclopropylmethyl)-1-((tetrahydro-2H-pyran-4-yl)methyl)pyrrolidin-3-yl)(3-(trifluoromethyl)-7,8-dihydro-1,6-naphthyridin-6(5H)-yl)methanone

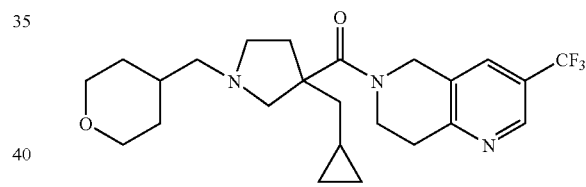

The title compound was prepared according to general procedures described in Scheme 5 (5.6 mg, 4% yield): $^1$H NMR (400 MHz, CD$_3$OD): δ 8.72 (s, 1H), 8.06 (m, 1H), 4.84 (s, 1H), 4.71 (d, 1H), 3.98-3.94 (m, 4H), 3.64 (m, 1H), 3.48 (m, 2H), 3.12 (m, 6H), 2.48 (s, 1H), 2.13 (s, 2H), 1.86-1.80 (dd, 2H), 1.68 (d, 2H), 1.49-1.29 (m, 3H), 0.58-0.47 (m, 3H), 0.05 (m, 2H); MS (ESI) m/z: Calculated for C$_{24}$H$_{32}$F$_3$N$_3$O$_2$: 451.2. found: 452.2 (M+H)$^+$.

Example 9

(3-(Cyclopropylmethyl)-1-((2,2-dimethyltetrahydro-2H-pyran-4-yl)methyl)pyrrolidin-3-yl)(3-(trifluoromethyl)-7,8-dihydro-1,6-naphthyridin-6(5H)-yl)methanone

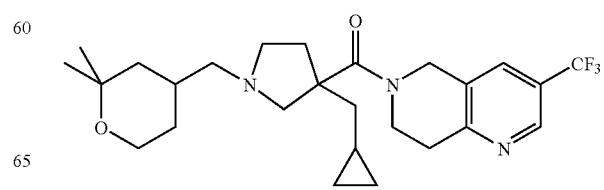

The title compound was prepared according to general procedures described in Scheme 5 (36.5 mg, 29.6% yield). $^1$H NMR (400 MHz, MeOH-d$_4$): δ 9.04 (s, 1H), 8.55 (s, 1H), 4.66 (d, 1H), 3.99 (m, 2H), 3.75 (m, 3H), 3.12 (m, 4H), 2.80 (m, 1H), 2.48 (m, 1H), 2.32 (m, 2H), 2.04 (d, 1H), 1.75 (m, 4H), 1.24 (m, 10H), 0.55 (m, 3H), 0.10 (d, 2H); MS (ESI) m/z: Calculated for C$_{26}$H$_{36}$F$_3$N$_3$O$_2$: 479.3. found: 480.2 (M+H)$^+$.

Example 10

(3-(Cyclopropylmethyl)-1-((5-methoxy-2-methyl-2, 3-dihydrobenzofuran-6-yl)methyl)pyrrolidin-3-yl)(3-(trifluoromethyl)-7,8-dihydro-1,6-naphthyridin-6 (5H)-yl)methanone

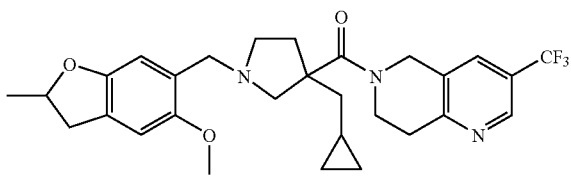 [SMILES: COc1cc2c(cc1CN1CCC(CC3CC3)(C(=O)N3CCc4ncc(C(F)(F)F)cc4C3)C1)OC(C)C2]

The title compound was prepared according to general procedures described in Scheme 5 (30.5 mg, 22.5% yield). $^1$H NMR (400 MHz, MeOH-d$_4$): δ 8.71 (s, 1H), 8.06 (s, 1H), 7.02 (s, 1H), 6.76 (s, 1H), 4.47 (d, 1H), 4.32 (bs, 2H), 3.87 (m, 4H), 3.55 (m, 2H), 3.34 (m, 2H), 3.19 (d, 1H), 3.11 (m, 2H), 2.85 (m, 2H), 2.46 (m, 2H), 2.15 (m, 2H), 1.78 (m, 2H), 1.40 (d, 3H), 0.44 (m, 3H), 0.10 (m, 2H); MS (ESI) m/z: Calculated for C$_{29}$H$_{34}$F$_3$N$_3$O$_3$: 529.3. found: 530.2 (M+H)$^+$.

Example 11

5-((3-(Cyclopropylmethyl)-3-(3-(trifluoromethyl)-5, 6,7,8-tetrahydro-1,6-naphthyridine-6-carbonyl)pyrrolidin-1-yl)methyl)-3-methylbenzo[d]thiazol-2(3H)-one

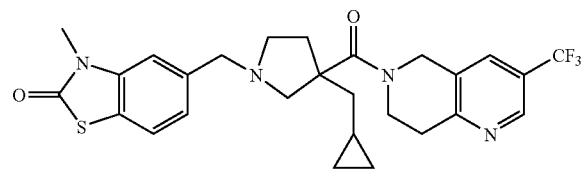

The title compound was prepared according to general procedures described in Scheme 5 (42.0 mg, 35.5% yield). $^1$H NMR (400 MHz, CDCl$_3$): δ 8.71 (s, 1H), 7.69 (s, 1H), 7.35 (d, 1H), 7.12 (m, 2H), 4.79 (m, 1H), 3.83 (d, 2H), 3.66 (q, 2H), 3.47 (m, 3H), 3.27 (d, 1H), 3.13 (q, 2H), 2.97 (s, 1H), 2.69 (m, 2H), 2.59 (m, 1H), 2.42 (m, 1H), 1.96 (m, 1H), 1.82 (m, 1H), 1.68 (m, 2H), 0.59 (m, 2H), 0.41 (m, 2H); MS (ESI) m/z: Calculated for C$_{27}$H$_{29}$F$_3$N$_4$O$_2$S: 530.2. found: 531.1 (M+H)$^+$.

Example 12

5-((3-(Cyclopropylmethyl)-3-(3-(trifluoromethyl)-5, 6,7,8-tetrahydro-1,6-naphthyridine-6-carbonyl)pyrrolidin-1-yl)methyl)benzo[d]thiazol-2(3H)-one

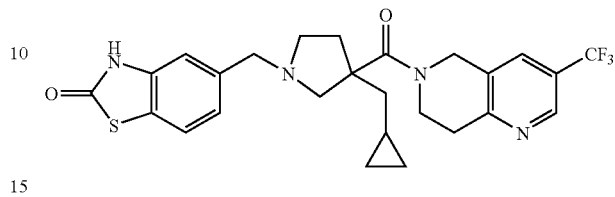

The title compound was prepared according to general procedures described in Scheme 5 (73.9 mg, 56.4% yield). $^1$H NMR (400 MHz, CDCl$_3$): δ 8.71 (s, 1H), 7.69 (s, 1H), 7.30 (d, 1H), 7.17 (s, 1H), 7.09 (d, 1H), 4.79 (m, 2H), 3.92 (m, 1H), 3.80 (m, 1H), 3.62 (q, 2H), 3.26 (d, 1H), 3.11 (q, 2H), 2.71 (m, 2H), 2.59 (m, 1H), 2.42 (m, 1H), 2.08 (s, 1H), 1.95 (m, 1H), 1.81 (m, 1H), 1.67 (m, 1H), 0.59 (m, 1H), 0.40 (m, 2H), −0.07 (m, 2H); MS (ESI) m/z: Calculated for C$_{26}$H$_{27}$F$_3$N$_4$O$_2$S: 516.2. found: 517.1 (M+H)$^+$.

Example 13

3-(Cyclopropylmethyl)-1-(4-hydroxy-4-(6-methoxypyridin-3-yl)cyclohexyl)pyrrolidin-3-yl)(3-(trifluoromethyl)-7,8-dihydro-1,6-naphthyridin-6(5H)-yl) methanone

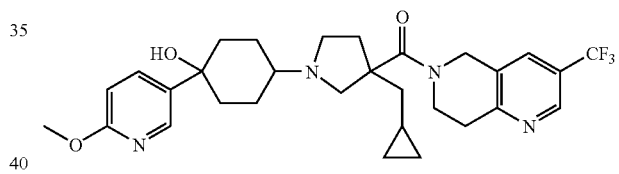

The title compound was prepared according to the same procedures as described for Example 30 (70.0 mg, 73.7% yield). $^1$H NMR (300 MHz, CD$_3$Cl$_3$): δ 8.72 (s, 1H), 8.29 (d, 1H), 8.06 (s, 1H), 7.97 (dd, 1H), 6.93 (d, 1H), 4.60 (m, 2H), 3.96 (m, 7H), 3.72 (m, 1H) 3.38 (m, 1H), 3.13 (m, 4H), 2.50 (m, 4H), 2.20 (m, 1H), 2.0.7 (bs, 1H), 1.95-1.82 (m, 5H), 1.69 (m, 1H), 0.60 (bs, 1H), 0.46 (bs, 2H), 0.02 (bs, 2H); MS (ESI) m/z: Calculated for C$_{30}$H$_{37}$F$_3$N$_4$O$_3$: 558.3. found: 559.2 (M+H)$^+$.

Example 14

(3-(Cyclopropylmethyl)-1-(2,2-dimethylchromoa-6-yl)methyl)pyrrolidin-3-yl)(3-(trifluoromethyl)-7,8-dihydro-1,6-naphthyridin-6(5H)-yl)methanone

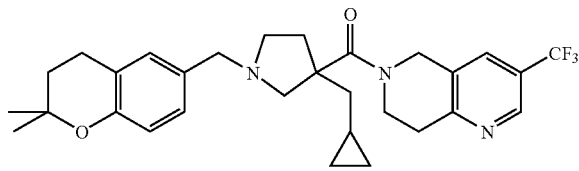 [SMILES: CC1(C)CCc2cc(CN3CCC(CC4CC4)(C(=O)N4CCc5ncc(C(F)(F)F)cc5C4)C3)ccc2O1]

The title compound was prepared according to general procedures described in Scheme 5 (35 mg, 16% yield). $^1$H NMR (400 MHz, CD$_3$OD): δ 8.73 (s, 1H), 8.08 (s, 1H), 7.08 (s, 1H), 7.25-7.19 (m, 1H), 6.80 (d, 1H), 4.60-3.90 (m, 6H), 3.62-3.01 (m, 4H), 2.90-2.20 (m, 8H), 1.80 (d, 2H), 1.36 (s, 6H), 0.61-0.02 (m, 5H); MS (ESI) m/z: Calculated for C$_{30}$H$_{36}$F$_3$N$_3$O$_2$: 527.3. found: 528.1 (M+H)$^+$.

Example 15

7-((3-(Cyclopropylmethyl)-3-(3-(trifluoromethyl)-5,6,7,8-tetrahydro-1,6-naphthyridin-6-carbonyl)pyrrolidin-1-yl)methyl)quinolin-2(1H)-one The title compound was prepared via the following intermediates using the procedures described below.

N-m-Tolylcinnamamide

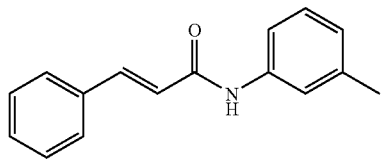 [SMILES: Cc1cccc(NC(=O)/C=C/c2ccccc2)c1]

m-Toluidine (5 g, 46.64 mmol) and pyridine (3.77 mL, 46.64 mmol) were dissolved in dry dichloromethane (25 mL). To the reaction mixture, cinnamoyl chloride (7.72 g, 46.64 mmol) was added and stirred for 3 h at 0° C. The reaction mixture was extracted with dichloromethane washing with water and 2N HCl. The solvent was removed and the crude product was used in the next step without further purification.

7-Methylquinolin-2(1H)-one

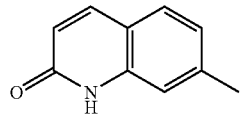

N-m-tolylcinnamamide (2 g, 0.834 mmol) and AlCl$_3$ (1.12 g, 0.834 mmol) were heated for 1 h at 100° C. Water was added and the solid was filtered to provide 1.2 g of crude product.

7-(Bromomethyl)quinolin-2(1H)-one

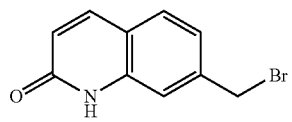 [SMILES: O=c1ccc2ccc(CBr)cc2[nH]1]

The title compound was prepared according to general procedures described in Scheme 3 (90 mg, 24% yield). $^1$H NMR (400 MHz, CDCl$_3$): δ 7.64 (d, 1H), 7.55 (d, 1H), 7.38 (s, 1H), 7.28 (d, 1H), 6.73 (d, 1H), 4.60 (s, 2H); MS (ESI) m/z: Calculated for C$_{10}$H$_8$BrNO: 236.9. found: 238.1 (M+H)$^+$.

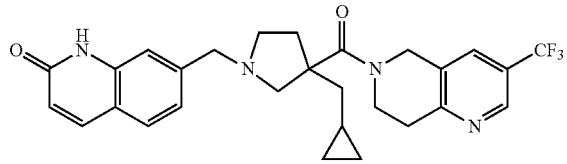 [SMILES: O=C(N1CCc2ncc(C(F)(F)F)cc2C1)C1(CC2CC2)CCN(Cc2ccc3ccc(=O)[nH]c3c2)C1]

The title compound was prepared according to general procedures described in Scheme 5 (20 mg, 27% yield). $^1$H NMR (400 MHz, CD$_3$OD): δ 8.76 (s, 1H), 8.07 (s, 1H), 8.01 (d, 1H), 7.80 (s, 1H), 7.51 (s, 1H), 7.40 (d, 1H), 6.78 (d, 1H), 4.70-4.40 (m, 6H), 4.00-3.01 (m, 4H), 2.60-2.55 (m, 2H), 1.96-1.91 (m, 2H), 1.80 (d, 2H), 0.60-0.02 (m, 5H); MS (ESI) m/z: Calculated for C$_{28}$H$_{29}$F$_3$N$_4$O$_2$: 510.2. found: 511.2 (M+H)$^+$.

Example 16

5-(1-(3-(Cyclopropylmethyl)-3-(3-(trifluoromethyl)-5,6,7,8-tetrahydro-1,6-naphthyridine-6-carbonyl)pyrrolidin-1-yl)ethyl)-1,3-dimethyl-1H-benzo[d]imidazol-2(3H)-one The title compound was prepared via the intermediate shown below using the procedures described below.

5-Acetyl-1,3-dimethyl-1H-benzo[d]imidazol-2(3H)-one

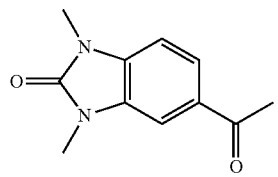

5-Acetyl-1H-benzo[d]imidazol-2(3H)-one (1 g, 5.67 mmol), methyl iodide (3.22 g, 22.71 mmol), and cesium carbonate (4.62 g, 14.19 mmol) were dissolved in DMF (2 mL). The reaction mixture was irradiated by microwave for 30 minutes at 100° C. The solvent was removed and extracted with dichloromethane. Purification by silica chromatography (ISCO) produced 5-acetyl-1,3-dimethyl-1H-benzo[d]imidazol-2(3H)-one (0.95 g, 82%). $^1$H NMR (400 MHz, CDCl$_3$): δ 7.79 (d, 1H), 7.61 (s, 1H), 7.00 (d, 1H), 3.50 (s, 6H), 2.62 (s, 3H); MS (ESI) m/z: Calculated for C$_{11}$H$_{12}$N$_2$O$_2$: 204.1. found: 205.2 (M+H)$^+$.

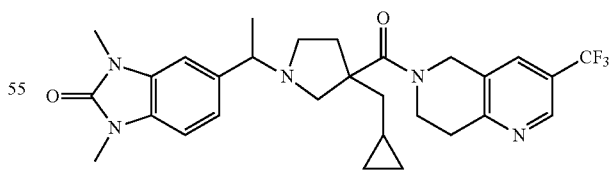

The title compound was prepared according to general procedures described in Scheme 6 using 1 equivalent of Ti(O-iPr)$_4$ (14 mg, 4% yield). $^1$H NMR (300 MHz, CDCl$_3$): δ 8.79 (s, 1H), 7.78 (s, 1H), 7.40-6.90 (m, 3H), 4.90-4.65 (m, 4H), 4.20-3.80 (m, 3H), 3.44 (s, 3H), 3.40 (s, 3H), 3.20-3.15 (m, 2H), 2.95-2.36 (m, 4H), 2.01-1.82 (m, 2H), 1.80 (d, 3H), 0.60-0.02 (m, 5H); MS (ESI) m/z: Calculated for C$_{29}$H$_{34}$F$_3$N$_5$O$_2$: 541.3. found: 542.4 (M+H)$^+$.

Example 17

(1-((1H-Indazol-5-yl)methyl)-3-(cyclopropylmethyl) pyrrolidin-3-yl)(3-(trifluoromethyl)-7,8-dihydro-1,6-naphthyridin-6(5H)-yl)methanone

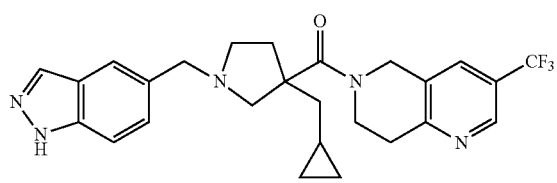 [SMILES: O=C(N1CCc2ncc(C(F)(F)F)cc2C1)C1(CC2CC2)CCN(Cc2ccc3[nH]ncc3c2)C1]

The title compound was prepared according to general procedures described in Scheme 5 (38 mg, 16% yield). $^1$H NMR (400 MHz, DMSO-d$_6$): δ 13.28 (bs, 2H), 9.94 (bs, 1H), 9.77 (bs, 1H), 8.78 (d, 1H), 8.19 (m, 2H), 7.94 (s, 1H), 7.63 (m, 1H), 7.48 (d, 1H), 4.85-1.78 (m, 16H), 0.49-0.32 (m, 3H), −0.01 (m, 2H), MS (ESI) m/z: Calculated for C$_{26}$H$_{28}$F$_3$N$_5$O: 483.2. found: 484 (M+H)$^+$.

Example 18

(3-(Cyclopropylmethyl)-1-(4-hydroxy-4-(6-methoxypyridin-3-yl)cyclohexyl)pyrrolidin-3-yl)(3-(trifluoromethyl)-7,8-dihydro-1,6-naphthyridin-6(5H)-yl)methanone

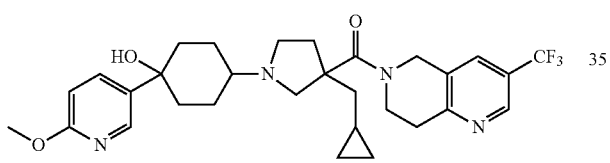

The title compound was prepared according to the procedures described in Example 30 (15 mg, 8% yield). $^1$H NMR (400 MHz, CD$_3$OD): δ 8.63 (s, 1H), 8.15 (s, 1H), 7.96 (s, 1H), 7.65 (d, 1H), 6.74 (d, 1H), 4.73 (s, 2H), 3.88-3.60 (m, 6H), 3.24-3.04 (m, 6H), 2.42-1.56 (m, 12H), 0.59-0.37 (m, 3H), −0.04-0.23 (m, 2H); MS (ESI) m/z: Calculated for C$_{30}$H$_{37}$F$_3$N$_4$O$_3$: 558.3. found: 559 (M+H)$^+$.

Example 19

6-((3-(Cyclobutylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one

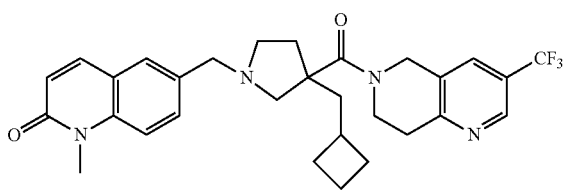 [SMILES: Cn1c(=O)ccc2cc(CN3CCC(CC4CCC4)(C(=O)N4CCc5ncc(C(F)(F)F)cc5C4)C3)ccc21]

The title compound was prepared according to the general procedures described in Scheme 5 (7.1 mg TFA-salt, 4% yield): $^1$H NMR (400 MHz, MeOH-d$_4$): δ 8.71 (s, 1H), 8.05 (m, 1H), 7.95 (d, 1H), 7.81 (d, 1H), 7.76 (s, 1H), 7.44 (d, 1H), 6.75 (d, 2H), 4.56 (m, 4H), 3.98 (m, 2H), 3.77 (s, 3H), 3.62-3.35 (m, 3H), 3.12 (m, 2H), 2.65 (s, 1H), 2.48 (m, 1H), 2.16 (m, 1H), 1.93 (m, 2H), 1.82-1.5 (m, 5H), 1.3-0.7 (m, 1H); MS (ESI) m/z: Calculated for C$_{30}$H$_{33}$F$_3$N$_4$O$_2$: 538.3. found 539.4 (M+H)$^+$.

Example 20

6-((3-Isopentyl-3-(3-(trifluoromethyl)-5,6,7,8-tetrahydro-1,6-naphthyridine-6-carbonyl)pyrrolidin-1-yl)methyl)-1-methylquinolin-2(1H)-one

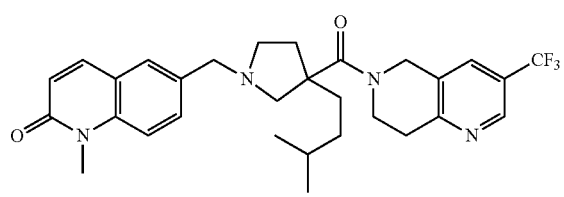 [SMILES: CC(C)CCC1(C(=O)N2CCc3ncc(C(F)(F)F)cc3C2)CCN(Cc2ccc3c(ccc(=O)n3C)c2)C1]

The title compound was prepared according to the general procedures described in Scheme 5 (9.0 mg TFA-salt, 2.4% yield): $^1$H NMR (400 MHz, MeOH-d$_4$): δ 8.71 (s, 1H), 8.07 (m, 1H), 7.95 (d, 1H), 7.82 (d, 1H), 7.77 (s, 1H), 7.44 (d, 1H), 6.75 (dd, 2H), 4.55 (m, 4H), 3.98-3.39 (m, 4H), 3.78 (s, 3H), 3.10 (m, 4H), 2.63-1.20 (m, 3H), 1.10-0.50 (m, 9H); MS (ESI) m/z: Calculated for C$_{30}$H$_{35}$F$_3$N$_4$O$_2$: 540.3. found 541.4 (M+H)$^+$.

Example 21

6-((3-Benzyl-3-(3-(trifluoromethyl)-5,6,7,8-tetrahydro-1,6-naphthyridine-6-carbonyl)pyrrolidin-1-yl) methyl)-1-methylquinolin-2(1H)-one

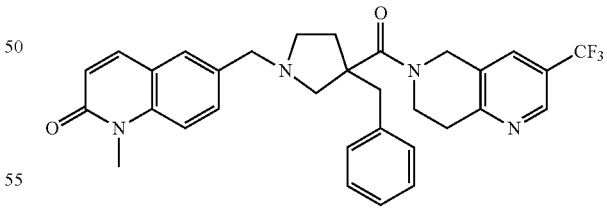

The title compound was prepared according to the general procedures described in Scheme 5 (17.0 mg TFA-salt, 3% yield): $^1$H NMR (400 MHz, DMSO-d$_6$): δ 8.81 (s, 1H), 8.17 (m, 1H), 7.94 (dd, 1H), 7.79 (m, 1H), 7.77 (s, 1H), 7.38 (m, 1H), 7.10 (m, 5H), 6.69 (d, 1H), 4.85 (m, 2H), 4.53 (m, 2H), 3.91 (m, 3H), 3.37 (s, 3H), 3.12 (m, 6H), 2.97 (m, 1H), 2.52 (m, 1H), 2.3 (m, 1H); MS (ESI) m/z: Calculated for C$_{32}$H$_{31}$F$_3$N$_4$O$_2$: 560.2. found 561.3 (M+H)$^+$.

Example 22

6-((3-(Cyclopropylmethyl)-3-(3-(trifluoromethyl)-5,6,7,8-tetrahydro-1,6-naphthyridine-6-carbonyl)pyrrolidin-1-yl)methyl)-1-methylquinolin-2(1H)-one

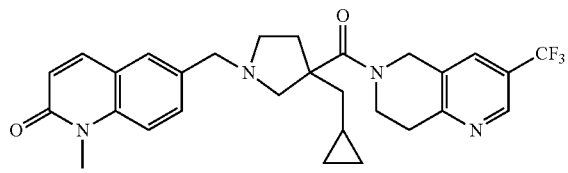 [SMILES: Cn1c(=O)ccc2cc(CN3CCC(CC4CC4)(C(=O)N4CCc5ncc(C(F)(F)F)cc5C4)C3)ccc21]

The title compound was prepared according to the general procedures described in Scheme 5 (21.0 mg TFA-salt, 15% yield): $^1$H NMR (400 MHz, DMSO-d$_6$): δ 8.82 (s, 1H), 8.20 (m, 1H), 7.96 (m, 1H), 7.87 (s, 1H), 7.78 (m, 1H), 7.67 (d, 1H), 6.71 (d, 1H), 4.80 (m, 2H), 4.48 (s, 2H), 4.35-3.77 (m, 3H), 3.67 (s, 3H), 3.51-3.27 (m, 5H), 3.03 (m, 2H), 1.85 (m, 2H), 0.58-0.00 (m, 5H); MS (ESI) m/z: Calculated for $C_{29}H_{31}F_3N_4O_2$: 524.2. found 525.1 (M+H)$^+$.

Example 23

5-((3-(Cyclopropylmethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

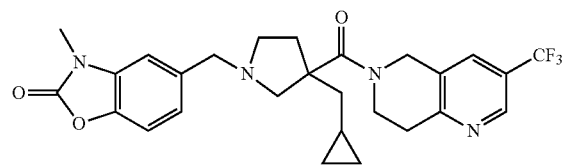 [SMILES: Cn1c(=O)oc2ccc(CN3CCC(CC4CC4)(C(=O)N4CCc5ncc(C(F)(F)F)cc5C4)C3)cc21]

The title compound was prepared according to the general procedures described in Scheme 5 (5.2 mg TFA-salt, 1% yield): $^1$H NMR (400 MHz, MeOH-d$_4$): δ 8.71 (s, 1H), 8.04 (s, 1H), 7.33 (m, 3H), 4.80 (m, 2H), 4.45 (m, 2H), 4.15-3.50 (m, 3H), 3.43 (s, 3H), 3.45-3.32 (m, 1H), 3.31-3.18 (m, 1H), 3.12 (m, 2H), 2.65 (s, 1H), 2.51 (m, 1H), 2.32-1.88 (m, 1H), 1.84 (m, 2H), 0.6-(−0.16) (m, 5H); MS (ESI) m/z: Calculated for $C_{27}H_{29}F_3N_4O_3$: 514.2. found 515.1 (M+H)$^+$.

Example 24

5-((3-Isobutyl-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

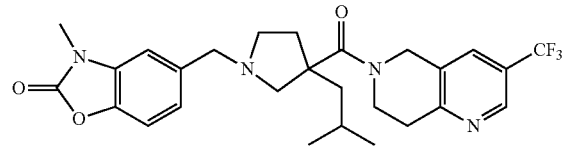 [SMILES: CC(C)CC1(C(=O)N2CCc3ncc(C(F)(F)F)cc3C2)CCN(Cc2ccc3oc(=O)n(C)c3c2)C1]

The title compound was prepared according to the general procedures described in Scheme 5 (21 mg TFA-salt, 19% yield): $^1$H NMR (400 MHz, MeOH-d$_4$): δ 8.71 (s, 1H), 8.11-8.00 (m, 1H), 7.37-7.23 (m, 3H), 4.85 (m, 2H), 4.49-4.43 (m, 4H), 4.15-3.90 (m, 4H), 3.60-3.47 (m, 2H), 3.43 (s, 3H), 3.25-3.12 (m, 2H), 2.48-1.36 (m, 2H), 0.89-0.60 (m, 7H); MS (ESI) m/z: Calculated for $C_{27}H_{31}F_3N_4O_3$: 516.2. found 517.2 (M+H)$^+$.

Example 25

7-((3-(Methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one The title compound was prepared via the intermediates shown below using the procedures described below.

1-tert-Butyl 3-methyl 3-(methoxymethyl)pyrrolidine-1,3-dicarboxylate

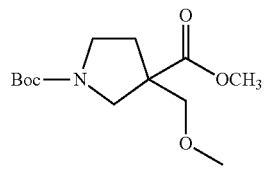 [SMILES: COCC1(C(=O)OC)CCN(C(=O)OC(C)(C)C)C1]

The title compound was prepared according to general procedure A described in connection with Scheme 2. 1-tert-Butyl 3-methylpyrrolidine-1,3-dicarboxylate (7.27 g, 31.7 mmol) was dissolved in 80 mL of THF under argon. 2M LDA in heptane/THF/Ethylbenzene (19 mL, 38 mmol) was added in 30 min. between −78° C. and −68° C. The reaction mixture was stirred at −78° C. for 45 min. Neat bromo(methoxy)methane (5.25 g, 41.2 mmol) was added over 11 min. at −78° C. The reaction was slowly warmed to RT and stirred for 20 h. The reaction mixture was cooled to −20° C. and quenched with 50 mL 10% NH$_4$Cl. The aqueous layer was extracted with 50 mL EtOAc. The organic layer was washed with 50 mL brine and then dried over Na$_2$SO$_4$. The solvent was evaporated and the resulting residue was purified by 2 flash chromatographies on silica gel using Hexanes/EtOAc 10:1 to 2:1 and 1/3 to give 4.5 g (52% yield) of the desired product. MS (ESI) m/z: Calculated for $C_{13}H_{23}NO_5$: 273.2. found: 295 (M+Na)$^+$.

1-(tert-Butoxycarbonyl)-3-(methoxymethyl)pyrrolidine-3-carboxylic acid, IIIc

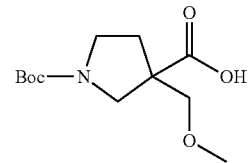

The title compound was prepared according to general procedure B described in connection with Scheme 2. 1-tert-Butyl 3-methyl 3-(methoxymethyl)pyrrolidine-1,3-dicarboxylate (4.5 g, 16.5 mmol) was dissolved in 30 mL of MeOH and a solution LiOH (0.79 g, 33 mmol) in 20 mL was added. The reaction mixture was microwaved at 130° C. for 25 min in 5 vials. The methanol was evaporated and the residue was acidified to pH 1-2 with KHSO₄ solid. The acid was extracted with EtOAc (3×50 mL). The combined organic fractions were washed with 1N KHSO₄ and with brine and then dried over Na₂SO₄. The solvent was evaporated to give 7.09 g of the desired acid (91% crude yield). ¹H NMR (400 MHz, CDCl₃): δ 10.70 (bs, 1H), 3.76 (d, 1H), 3.62-3.41 (m, 5H), 3.35 (s, 3H), 2.34-2.25 (m, 1H), 1.98-1.93 (m, 1H), 1.45 (s, 9H); MS (ESI) m/z: Calculated for $C_{12}H_{21}NO_5$: 259.1. found: 260 (M+1)⁺.

tert-Butyl 3-(methoxymethyl)-3-(3-(trifluoromethyl)-5,6,7,8-tetrahydro-1,6-naphthyridine-6-carbonyl)pyrrolidine-1-carboxylate Vc

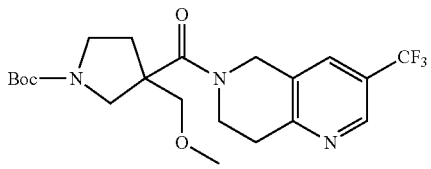 [SMILES: COCC1(C(=O)N2CCc3ncc(C(F)(F)F)cc3C2)CCN(C(=O)OC(C)(C)C)C1]

The title compound was prepared according to general procedure C described in connection with Scheme 2. To 1-(tert-butoxycarbonyl)-3-(methoxymethyl)pyrrolidine-3-carboxylic acid (3 g, 11.6 mmol) in dichloromethane (30 mL) was added 2M oxalyl chloride dichloromethane solution (17 mL, 34 mmole) and a few drops of DMF at room temperature. The mixture was stirred at RT for 2 hours and concentrated to dryness under the reduced pressure. 3-(Trifluoromethyl)-5,6,7,8-tetrahydro-1,6-naphthyridine dichloride (3.19 g, 11.6 mmole) in 30 dichloromethane and triethyl amine (3.1 g, 30 mmole) was added to the above residue at 0° C. The mixture was stirred at 0° C. for 1 h, diluted with dichloromethane (100 mL) and washed with sodium bicarbonate solution (2×50 mL) and water (3×100 mL), dried over sodium sulfate and purified by silica chromatography using 2.5% MeOH in CH₂Cl₂ as eluent to give product (1.7 g, 33% yield). ¹H NMR (400 MHz, CD₃OD): δ 8.70 (s, 1H), 7.68 (m, 1H), 4.80 (s, 2H), 4.10-2.95 (m, 13H), 2.40-2.15 (m, 2H), 1.48 (s, 9H); MS (ESI) m/z: Calculated for $C_{21}H_{28}F_3N_3O_4$: 443.2. found: 466 (M+Na)⁺.

(3-(Methoxymethyl)pyrrolidin-3-yl)(3-(trifluoromethyl)-7,8-dihydro-1,6-naphthyridin-6(5H)-yl)methanone 2,2,2-trifluoroacetate Vic The title compound was prepared via the following intermediate using the procedures described below.

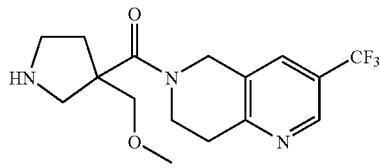 [SMILES: COCC1(C(=O)N2CCc3ncc(C(F)(F)F)cc3C2)CCNC1]

The title compound was prepared according to general procedure D described in connection with Scheme 2. tert-Butyl 3-(methoxymethyl)-3-(3-(trifluoromethyl)-5,6,7,8-tetrahydro-1,6-naphthyridine-6-carbonyl)pyrrolidine-1-carboxylate (1.7 g, 3.84 mmole) was dissolved in 50 mL CH₂Cl₂ and 16 mL TFA was added at RT. The reaction mixture was stirred for 17 h and the solvents evaporated. The residue was dissolved in CH₂Cl₂ and the organic layer was washed twice with 50 mL of saturated NaHCO₃ and then dried over Na₂SO₄. The solvent was evaporated to give product (1.3 g, quantitative yield) of the desired product. ¹H NMR (400 MHz, CDCl₃): δ 8.71 (s, 1H), 7.70 (s, 1H), 4.81 (s, 2H), 4.13-3.89 (m, 2H), 3.52-3.43 (m, 3H), 3.29 (s, 3H), 3.12-2.97 (m, 5H), 2.22-2.18 (m, 1H), 2.04-1.97 (m, 1H); MS (ESI) m/z: Calculated for $C_{16}H_{20}F_3N_3O_2$(free base): 343.2. found: 344 (M+H)⁺.

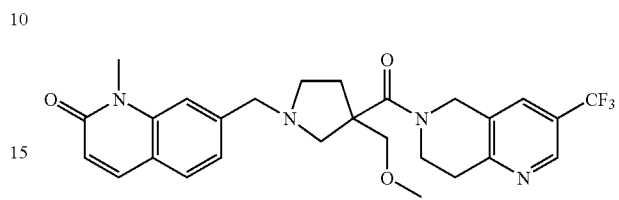

The title compound was prepared according to the general procedures described in Scheme 5. A mixture of (3-(methoxymethyl)pyrrolidin-3-yl)(3-(trifluoromethyl)-7,8-dihydro-1,6-naphthyridin-6(5H)-yl)methanone 2,2,2-trifluoroacetate (128.5 mg, 0.505 mmole), 7-(bromomethyl)-1-methylquinolin-2(1H)-one (289 mg, 0.505 mmole), K₂CO₃ (139 mg, 1 mmole) and DIEA (130 mg, 1 mmole) in DMF (3 mL) was microwaved at 100° C. for 30 min, diluted with ethyl acetate, washed with water, dried over sodium sulfate, filtered, concentrated and purified by reverse phase preparative HPLC to yield the desired final product with purity greater than 98% (32 mg TFA-salt, 8.5% yield). ¹H NMR (400 MHz, DMSO-d₆): δ 10.11 (s, 1H), 10.05 (s, 1H), 8.79 (s, 1H), 8.17 (s, 1H), 7.95 (d, 1H), 7.81 (d, 1H), 7.72 (d, 1H), 7.39 (d, 1H), 6.69 (d, 1H), 4.8-4.28 (m, 4H), 3.87-2.21 (m, 18H); MS (ESI) m/z: Calculated for $C_{27}H_{29}F_3N_4O_3$: 514.2. found: 515 (M+H)⁺.

Examples 26 and 27

(S)-7-((3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one and (R)-7-((3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one

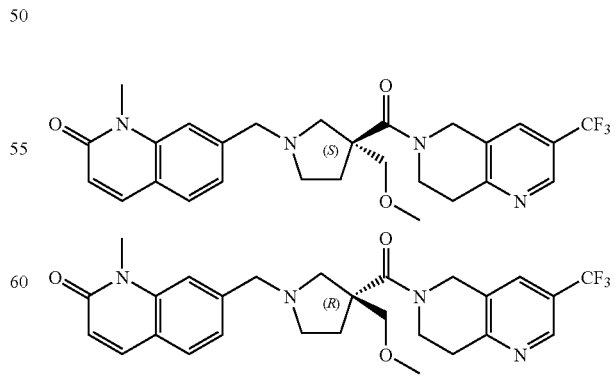

The racemic mixture (ca. 1:1 ratio) was separated into the two enantiomers by normal phase preparative HPLC using a

Example 28

5-((3-(Methoxymethyl)-3-(3-(trifluoromethyl)-5,6,7,8-tetrahydro-1,6-naphthyridine-6-carbonyl)pyrrolidin-1-yl)methyl)-3-methylbenzo[d]thiazol-2(3H)-one

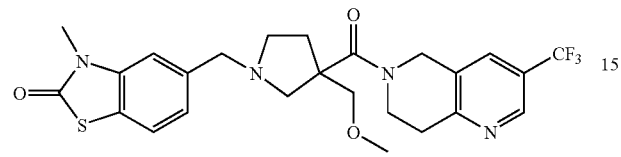

The title compound was prepared according to general procedures described in Scheme 5 using VIc (44.6 mg, 58.7% yield). $^1$H NMR (400 MHz, CD$_3$Cl$_3$): δ 8.74 (s, 1H), 7.74 (s, 1H), 7.45 (d, 1H), 7.39 (s, 1H), 7.16 (d, 1H), 4.78 (m, 2H), 4.31 (dd, 2H), 3.90 (m, 4H), 3.75-3.60 (m, 4H), 3.45 (m, 3H), 3.24 (m, 1H), 3.15 (m, 2H), 2.67 (s, 3H), 2.46 (s, 1H); MS (ESI) m/z: Calculated for C$_{25}$H$_{27}$F$_3$N$_4$O$_3$S: 520.2. found: 521.1 (M+H)$^+$.

Example 29

5-(1-(3-(Methoxymethyl)-3-(3-(trifluoromethyl)-5,6,7,8-tetrahydro-1,6-naphthyridine-6-carbonyl)pyrrolidin-1-yl)ethyl)-1,3-dimethyl-1H-benzo[d]imidazol-2(3H)-one

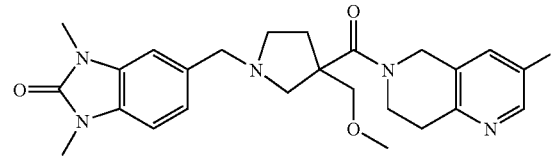

The title compound was prepared according to general procedures described in Scheme 6: A mixture of (3-(methoxymethyl)pyrrolidin-3-yl)(3-(trifluoromethyl)-7,8-dihydro-1,6-naphthyridin-6(5H)-yl)methanone VIc (50 mg, 0.146 mmol), 5-acetyl-1,3-dimethyl-1H-benzo[d]imidazol-2(3H)-one (30 mg, 0.146 mmol) and Ti(O$^i$Pr)$_4$ (51 mg, 0.182 mmol) in THF (2.5 mL) was irradiated in a Microwave instrument at 100° C. for 30 min (Personal Chemistry Emrys™ Optimizer microwave reactor). The reaction mixture was cooled and NaBH(OAc)$_3$ (93 mg, 0.438 mmol) was added. The mixture was stirred at room temperature overnight. The solvent was removed in vacuo. The residue was dissolved in 30 mL of ethyl acetate and washed with sat. NaHCO$_3$. The organic layer was washed with brine (×3), then dried over Na$_2$SO$_4$, filtered and concentrated under reduced pressure. The crude product was purified by reverse phase preparative HPLC to yield the desired final product as trifluoroacetic salt with purity greater than 95% (18.0 mg, 23.2% yield): $^1$H NMR (300 MHz, CD$_3$Cl$_3$): δ 8.71 (s, 1H), 7.72 (s, 1H), 7.29 (bs, 1H), 7.01 (bs, 1H), 6.92 (s, 1H), 5.23 (m, 2H), 4.87 (m, 1H), 4.73 (m, 1H), 4.10-3.86 (m, 4H), 3.71 (m, 3H), 3.40 (m, 3H), 3.32-3.24 (m, 6H), 3.12 (m, 3H), 2.91 (bs, 1H), 2.66 (d, 1H), 2.42 (s, 1H), 2.30 (s, 1H), 1.81 (m, 2H); MS (ESI) m/z: Calculated for C$_{27}$H$_{32}$F$_3$N$_5$O$_3$: 531.3. found: 532.0 (M+H)$^+$.

Example 30 and 31

4-Hydroxy-4-(6-methoxypyridin-3-yl)cyclohexanone

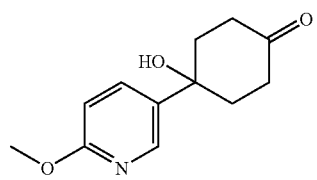 [SMILES: COc1ccc(C2(O)CCC(=O)CC2)cn1]

The title compound was prepared based on the procedures described in International Patent Application Publication No. WO 2004/050024, which is hereby incorporated by reference.

(1-(4-Hydroxy-4-(6-methoxypyridin-3-yl)cyclohexyl)-3-(methoxymethyl)pyrrolidin-3-yl)(3-(trifluoromethyl)-7,8-dihydro-1,6-naphthyridin-6(5H)-yl)methanone

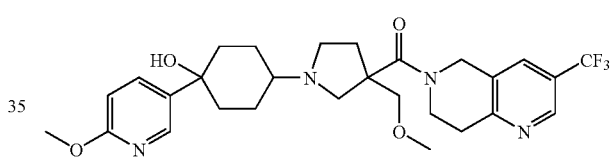

The title compound was prepared according to general procedures described in Scheme 2: A mixture of 4-hydroxy-4-(6-methoxypyridin-3-yl)cyclohexanone (71 mg, 0.32 mmol), (3-(methoxymethyl)pyrrolidin-3-yl)(3-(trifluoromethyl)-7,8-dihydro-1,6-naphthyridin-6(5H)-yl)methanone VIc (100 mg, 0.29 mmol) and acetic acid (20 µL, 0.34 mmol) in dichloroethane (3 mL) was stirred at room temperature for 0.5 h. Sodium triacetoxyborohydride (123 mg, 0.576 mmol) was added and the reaction mixture was stirred for 2 h at room temperature. After concentration of solvent under reduced pressure, the resulting residue was dissolved in ethyl acetate, then washed with NaHCO$_3$, water and brine. The organic extract was dried, filtered and concentrated. The crude product was obtained as a mixture of isomers which were further separated by reverse phase preparative HPLC to yield isomer A (eluted at 10.092 min) and isomer B (eluted at 11.269 min).

Isomer I (10.2 mg): $^1$H NMR (300 MHz, MeOH-d$_4$): δ 8.71 (s, 1H), 8.30 (s, 1H), 8.04 (s, 1H), 7.98 (d, 1H), 6.93 (d, 1H), 4.87 (m, 2H), 3.94 (m, 5H), 3.90 (s, 1H) 3.66 (m, 3H), 3.36 (m, 1H), 3.10 (bs, 2H), 2.65 (s, 7H), 2.36-2.33 (m, 5H), 1.82 (m, 2H), 1.68 (m, 2H); MS (ESI) m/z: Calculated for C$_{28}$H$_{35}$F$_3$N$_4$O$_4$: 548.3. found: 549.2 (M+H)$^+$.

Isomer II (4.4 mg): $^1$H NMR (300 MHz, MeOH-d$_4$): δ 8.72 (s, 1H), 8.25 (d, 1H), 8.05 (s, 1H), 7.88 (dd, 1H), 6.86 (d, 1H), 4.87 (m, 2H), 4.00 (t, 2H), 3.92 (s, 4H), 3.70-3.65 (m, 3H), 3.36 (m, 1H), 3.12 (t, 2H), 2.65 (s, 7H), 2.37-2.30 (m, 1H), 2.16 (m, 1H), 2.06 (m, 3H), 1.94 (m, 4H); MS (ESI) m/z: Calculated for C$_{28}$H$_{35}$F$_3$N$_4$O$_4$: 548.3. found: 549.2 (M+H)$^+$.

Example 32

6-((3-(Methoxymethyl)-3-(3-(trifluoromethyl)-5,6,7,8-tetrahydro-1,6-naphthyridine-6-carbonyl)pyrrolidin-1-yl)methyl)-4-methyl-2H-benzo[b][1,4]oxazin-3(4H)-one The title compound was prepared via the intermediate shown below using the procedures described below.

4-Methyl-3-oxo-3,4-dihydro-2H-benzo[b][1,4]oxazine-6-carbaldehyde

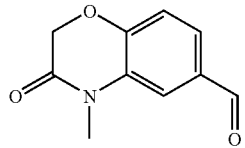

3-Oxo-3,4-dihydro-2H-benzo[b][1,4]oxazine-6-carbaldehyde (0.5 g, 2.82 mmol), methyl iodide (0.6 g, 4.23 mmol) and cesium carbonate (1.37 g, 4.23 mmol) were dissolved in dry dimethylformamide (2 mL). The reaction mixture was irradiated by microwave at 100° C. for 30 minutes. The solvent was removed and the residue was washed with water and extracted with dichloromethane. Purification by silica chromatography (ISCO) produced 4-methyl-3-oxo-3,4-dihydro-2H-benzo[b][1,4]oxazine-6-carbaldehyde (0.46 g, 85%). $^1$H NMR (400 MHz, DMSO-$d_6$): δ 9.95 (s, 1H), 7.62 (s, 1H), 7.59 (d, 1H), 7.20 (d, 1H), 4.80 (s, 2H), 3.34 (s, 3H); MS (ESI) m/z: Calculated for $C_{10}H_9NO_3$: 191.1. found: 192.1 (M+H)$^+$.

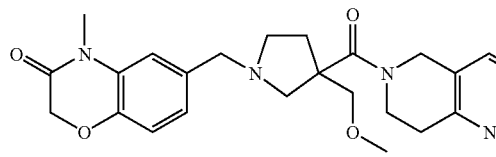

The title compound was prepared according to general procedures described in Scheme 5 using VIc (20 mg, 22% yield): $^1$H NMR (300 MHz, DMSO-$d_6$): δ 8.80 (s, 1H), 8.10 (s, 1H), 7.30 (br s, 1H), 7.20-7.00 (m, 2H), 4.80 (s, 2H), 4.70 (s, 2H), 4.33 (s, 2H), 3.90 (s, 2H), 3.50-3.01 (m, 10H), 3.52 (s, 3H), 3.31 (s, 3H); MS (ESI) m/z: Calculated for $C_{26}H_{29}F_3N_4O_4$: 518.2. found: 519.3 (M+H)$^+$.

Example 33

6-(1-(3-(Methoxymethyl)-3-(3-(trifluoromethyl)-5,6,7,8-tetrahydro-1,6-naphthyridine-6-carbonyl)pyrrolidin-1-yl)ethyl)-4-methyl-2H-benzo[b][1,4]oxazin-3(4H)-one The title compound was prepared via the intermediate shown below using the procedures described below.

6-Acetyl-4-methyl-2H-benzo[b][1,4]oxazin-3(4H)-one

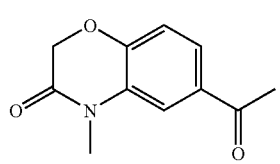

6-Acetyl-2H-benzo[b][1,4]oxazin-3(4H)-one (1 g, 5.23 mmol), methyl iodide (1.13 g, 7.84 mmol) and cesium carbonate (2.55 g, 7.84 mmol) were dissolved in DMF (2 mL). The reaction mixture was irradiated by microwave for 30 minutes at 100° C. The solvent was removed and extracted with dichloromethane. Purification by silica chromatography (ISCO) produced 6-acetyl-4-methyl-2H-benzo[b][1,4]oxazin-3(4H)-one (0.9 g, 84%). $^1$H NMR (400 MHz, CDCl$_3$): δ 7.63 (s, 1H), 7.60 (d, 1H), 7.01 (d, 1H), 4.70 (s, 2H), 3.42 (s, 3H), 2.60 (s, 3H); MS (ESI) m/z: Calculated for $C_{11}H_{11}NO_3$: 205.1. found: 206.1 (M+H)$^+$.

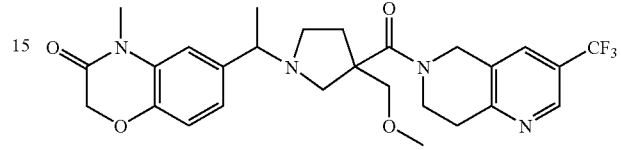

The title compound was prepared according to general procedures described in Scheme 6 using 1 equivalent of Ti(O-iPr)$_4$ (5 mg, 4% yield): $^1$H NMR (300 MHz, CDCl$_3$): δ 8.79 (s, 1H), 7.80 (s, 1H), 7.48-7.22 (m, 1H), 7.12-6.98 (m, 2H), 5.01-4.50 (m, 5H), 4.22-3.70 (m, 6H), 3.40-3.22 (m, 8H), 2.61-2.30 (m, 4H), 1.80 (d, 3H); MS (ESI) m/z: Calculated for $C_{27}H_{31}F_3N_4O_4$: 532.2. found: 533.2 (M+H)$^+$.

Example 34

5-(1-(3-(Methoxymethyl)-3-(3-(trifluoromethyl)-5,6,7,8-tetrahydro-1,6-naphthyridine-6-carbonyl)pyrrolidin-1-yl)ethyl)-3-methylbenzo[d]oxazol-2(3H)-one The title compound was prepared via the intermediate shown below using the procedures described below.

5-Acetyl-3-methylbenzo[d]oxazol-2(3H)-one

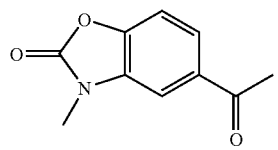

5-Acetylbenzo[d]oxazol-2(3H)-one (0.5 g, 2.82 mmol), methyl iodide (0.6 g, 4.23 mmol), and cesium carbonate (1.37 g, 4.23 mmol) were dissolved in DMF (2 mL). The reaction mixture was irradiated by microwave for 30 minutes at 100° C. The solvent was removed and extracted with dichloromethane. Purification by silica chromatography (ISCO) produced 5-acetyl-3-methylbenzo[d]oxazol-2(3H)-one (0.4 g, 74%). $^1$H NMR (400 MHz, CDCl$_3$): δ 7.89 (d, 1H), 7.80 (s, 1H), 7.00 (d, 1H), 3.48 (s, 3H), 2.60 (s, 3H); MS (ESI) m/z: Calculated for $C_{10}H_9NO_3$: 191.1. found: 192.1 (M+H)$^+$.

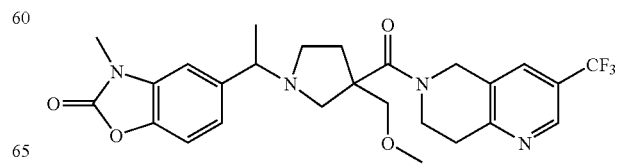

The title compound was prepared according to general procedures described in Scheme 6 using 1 equivalent of Ti(O-iPr)$_4$ (9 mg, 7% yield): $^1$H NMR (300 MHz, CDCl$_3$): δ 8.70 (s, 1H), 7.70 (s, 1H), 7.50-7.48 (m, 2H), 7.01 (m, 1H), 4.80-4.70 (m, 2H), 4.20-4.03 (m, 2H), 3.90-3.81 (m, 3H), 3.40 (s, 6H), 3.31-3.05 (m, 6H), 2.60-2.48 (m, 2H) 1.80 (d, 3H); MS (ESI) m/z: Calculated for C$_{26}$H$_{29}$F$_3$N$_4$O$_4$: 518.2. found: 519.2 (M+H)$^+$.

Example 35

(1-(4-Cyclopropyl-4-hydroxycyclohexyl)-3-(methoxymethyl)pyrrolidin-3-yl)(3-trifluoromethyl)-7,8-dihydro-1,6-naphthyridin-6(5H)-yl)methanone The title compound was prepared via the intermediates shown below using the procedures described below.

8-Cyclopropyl-1,4-dioxaspiro[4.5]decan-8-ol

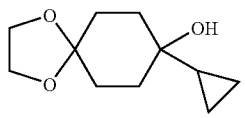

1,4-Dioxaspiro[4.5]decan-8-one (2 g, 12.80 mmol) was dissolved in dry tetrahydrofuran (20 mL). The reaction mixture was cooled to −78° C. Cyclopropylmagnesium bromide (51.2 mL, 25.61 mmol) was added dropwise over a period of 10 min. The reaction mixture was stirred for 4 h, quenched with sat. NH$_4$Cl and extracted with ethyl acetate. The solvent was evaporated and the crude product was used without further purification in the next step.

4-Cyclopropyl-4-hydroxycyclohexanone

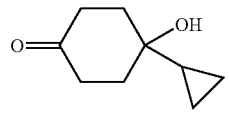

8-Cyclopropyl-1,4-dioxaspiro[4.5]decan-8-ol (1.8 g) was dissolved in acetone (30 mL). A solution of water (15 mL) and conc. HCl was added. The reaction mixture was stirred overnight. The reaction mixture was taken in ethyl acetate and washed with sat. NaHCO$_3$. Purification by silica chromatography produced 4-cyclopropyl-4-hydroxycyclohexanone (0.5 g, 27%). $^1$H NMR (400 MHz, CDCl$_3$): δ 2.80-2.69 (m, 2H), 2.50-2.42 (m, 2H), 1.99-1.78 (m, 4H), 1.01-0.99 (m, 1H), 0.50-0.47 (m, 4H); MS (ESI) m/z: Calculated for C$_9$H$_{14}$O$_2$: 154.1. found: 155.1 (M+H)$^+$.

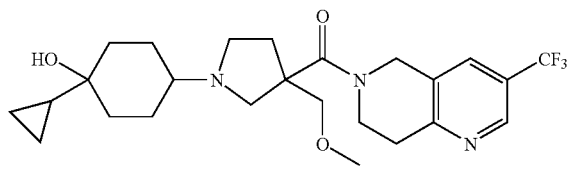 [SMILES: COCC1(C(=O)N2CCc3ncc(C(F)(F)F)cc3C2)CCN(C2CCC(O)(C3CC3)CC2)C1]

The title compound was prepared according to general procedures described in Scheme 8 (12 mg, 6% yield): $^1$H NMR (300 MHz, CDCl$_3$): δ 11.50 (br s, 1H), 8.80 (s, 1H), 7.82 (s, 1H), 4.90-4.68 (m, 4H), 3.99-3.03 (m, 8H), 3.35 (s, 3H), 2.77-2.72 (m, 1H), 2.60-1.50 (m, 10H), 0.05-0.01 (m, 5H); MS (ESI) m/z: Calculated for C$_{25}$H$_{34}$F$_3$N$_3$O$_3$: 481.3. found: 482.2 (M+H)$^+$.

Example 36

6-Chloro-7-((3-(methoxymethyl)-3-(3-(trifluoromethyl)-5,6,7,8-tetrahydro-1,6-naphthyridine-6-carbonyl)pyrrolidin-1-yl)methyl)-1-methylquinolin-2(1H)-one The title compound was prepared via the intermediates shown below using the procedures described below.

N-(4-Chloro-3-methylphenyl)cinnamamide

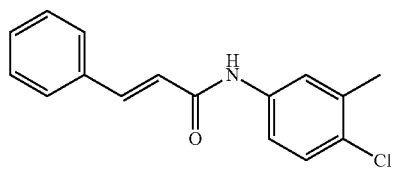 [SMILES: Cc1cc(NC(=O)/C=C/c2ccccc2)ccc1Cl]

To 4-chloro-3-methylaniline (3.33 g, 19.98 mmole) in dichloromethane (100 mL) and pyridine (20 mL) was added cinnamoyl chloride (2.83 g, 19.98 mmole) at 0° C. The mixture was stirred at room temperature for 2 h. Solvent and pyridine were removed by rotary evaporator under reduced pressure. The residue was diluted with ethyl acetate and washed 1N HCl (2×100 mL), water (2×100 mL), sodium bicarbonate solution (2×100 mL) and dried over sodium sulfate. After removing solvent a white solid was recovered (5.38 g, 99% yield). The product was used for the next step without further purification. $^1$H NMR (400 MHz, DMSO-d$_6$): δ 7.76-7.24 (m, 10H), 6.58 (d, 1H), 2.55 (s, 3H); MS (ESI) m/z: Calculated for C$_{16}$H$_{14}$ClNO: 271.1. found: 272 (M+H)$^+$.

6-Chloro-7-methylquinolin-2(1H)-one

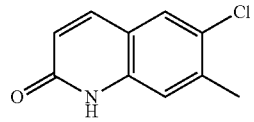

A mixture of N-(4-chloro-3-methylphenyl)cinnamamide (2.75 g, 10.15 mmole) and aluminum chloride (1.35 g, 10.15 mmole) was heated at 100° C. for 2 h. Ice was added to the reaction mixture. The mixture was extracted with dichloromethane, dried over sodium sulfate and purified by silica gel flash chromatography (eluted with 4% methanol in dichloromethane) to give a mixture of isomers (1:1) (600 mg), 6-chloro-7-methylquinolin-2(1H)-one and 6-chloro-5-methylquinolin-2(1H)-one. The mixture was used for the next step without further purification. MS (ESI) m/z: Calculated for $C_{10}H_8ClNO$: 193.0. found: 194 $(M+H)^+$.

6-Chloro-1,7-dimethylquinolin-2(1H)-one

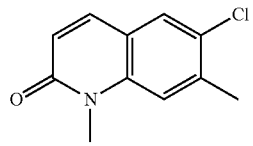

A mixture of 6-chloro-7-methylquinolin-2(1H)-one, 6-chloro-5-methylquinolin-2(1H)-one, $Cs_2CO_3$, and iodomethane in DMF was heated in a microwave reactor at 100° C. for 30 min. The mixture was diluted with dichloromethane, washed with water and dried over sodium sulfate. After removing the solvent the crude product (600 mg) was used in the next step without purification. MS (ESI) m/z: Calculated for $C_{11}H_{10}ClNO$: 207.1. found: 208 $(M+H)^+$.

7-(Bromomethyl)-6-chloro-1-methylquinolin-2(1H)-one

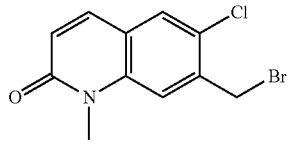

Crude 6-Chloro-1,7-dimethylquinolin-2(1H)-one (600 mg) dissolved in carbon-tetrachloride (30 ml) was added NBS (515.9 mg, 2.9 mmole) and AIBN (23.8 mg, 0.145 mmole). The mixture was heated under reflux for 3 h, diluted with dichloromethane, washed by sodium bicarbonate solution and water, dried over sodium sulfate, purified by silica chromatography (eluted with dichloromethane) to give a mixture of two isomers (550 mg). This mixture was used for the next step with out further purification. MS (ESI) m/z: Calculated for $C_{11}H_9BrClNO$: 285. found: 286 $(M+H)^+$.

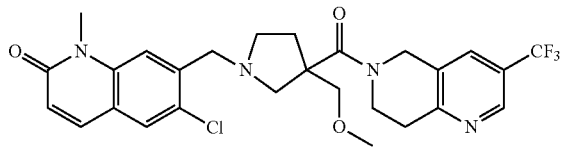 [SMILES: COCC1(C(=O)N2CCc3ncc(C(F)(F)F)cc3C2)CCN(Cc2cc3c(ccc(=O)n3C)cc2Cl)C1]

The title compound was prepared according to general procedures described in Scheme 5 using VIc (5 mg, 1% yield). $^1$H NMR (400 MHz, DMSO-$d_6$): δ 10.12 (bs, 1H), 10.05 (bs, 1H), 8.79 (s, 1H), 8.42 (d, 1H), 8.17 (s, 1H), 7.82 (m, 1H), 7.42 (s, 1H), 6.68 (d, 1H), 4.80-2.21 (m, 20H); MS (ESI) m/z: Calculated for $C_{27}H_{28}ClF_3N_4O_3$: 548.2. found: 549 $(M+H)^+$.

Example 37

6-Chloro-5-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

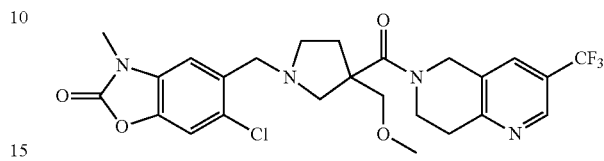

The title compound was prepared according to general procedures described in Scheme 5 using VIc (10 mg, 6% yield). $^1$H NMR (400 MHz, $CD_3OD$): δ 8.61 (s, 1H), 7.93 (s, 1H), 7.45 (s, 1H), 7.35 (s, 1H), 4.53 (s, 2H), 3.88-2.47 (m, 18H), 2.49-2.47 (m, 2H); MS (ESI) m/z: Calculated for $C_{25}H_{26}ClF_3N_4O_4$: 538.2. found: 539 $(M+H)^+$.

Example 38

5-((3-(Methoxymethyl)-3-(3-(trifluoromethyl)-5,6,7,8-tetrahydro-1,6-naphthyridine-6-carbonyl)pyrrolidin-1-yl)methyl)-1,3-dimethyl-1H-benzo[d]imidazol-2(3H)-one

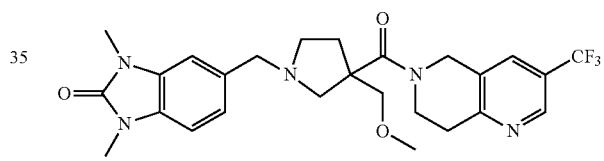

The title compound was prepared according to general procedures described in Scheme 5 (15 mg, 8% yield). $^1$H NMR (400 MHz, $CD_3OD$): δ 8.61 (s, 1H), 7.93 (s, 1H), 7.20-7.15 (m, 3H), 4.56 (s, 2H), 3.86-2.24 (m, 23H); MS (ESI) m/z: Calculated for $C_{26}H_{30}F_3N_5O_3$: 517.2. found: 518 $(M+H)^+$.

Example 39

5-((3-(Methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

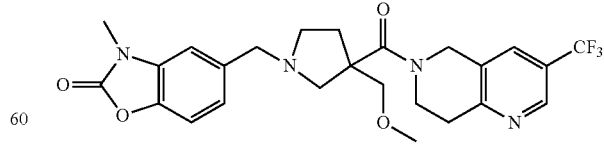

The title compound was prepared according to the general procedures described in Scheme 5 using VIc (15.3 mg TFA-salt, 17% yield): $^1$H NMR (400 MHz, MeOH-$d_4$): δ 8.70 (s, 1H), 8.03 (s, 1H), 7.33 (m, 3H), 4.84 (m, 2H), 4.45 (m, 4H), 3.95 (m, 4H), 3.78-3.52 (m, 4H), 3.43 (s, 3H), 3.40-3.20 (m, 1H), 3.09 (m, 2H), 2.65 (s, 2H); MS (ESI) m/z: Calculated for $C_{25}H_{27}F_3N_4O_4$: 504.2. found 505.1 (M+H)+.

Example 40 and 41

(R)-6-((3-(Methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one and (S)-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

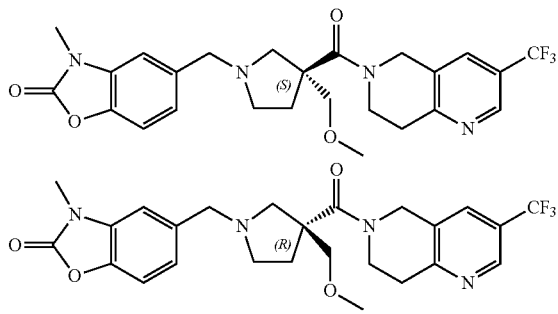

The racemic mixture (ca. 1:1 ratio) was separated into the two enantiomers by normal phase preparative HPLC using a chiral column, yielding enantiomer I (eluted at 6.98 min) and enantiomer II (eluted at 14.47 min).

Enantiomer I>99% ee; $^1$H NMR (300 MHz, CDCl$_3$): δ 8.69 (s, 1H), 7.65 (s, 1H), 7.12 (m, 3H), 7.06 (d, 1H), 6.98 (s, 1H), 4.82 (m, 2H), 4.04-3.99 (m, 2H), 3.98-3.62 (m, 4H), 3.23 (m, 3H), 3.08-2.96 (m, 3H), 2.78-2.74 (m, 2H), 2.51 (m, 1H), 2.25 (m, 1H), 2.06-2.00 (m, 1H), 1.63 (m, 1H); MS (ESI) m/z: Calculated for $C_{25}H_{27}F_3N_4O_4$: 504.54. found 505.1 (M+H)+.

Enantiomer II>98.6% ee; $^1$H NMR (300 MHz, CDCl$_3$): δ 8.69 (s, 1H), 7.61 (s, 1H), 7.12 (d, 1H), 7.06 (d, 1H), 6.98 (s, 1H), 4.83 (m, 2H), 4.06-3.74 (m, 2H), 3.64-3.57 (m, 4H), 3.23 (m, 3H), 3.08 (m, 2H), 3.06 (m, 2H), 2.97 (m, 1H), 2.78-2.71 (m, 2H), 2.52 (m, 1H) 2.30 (m, 1H), 2.06 (m, 1H), 1.62 (m, 1H); MS (ESI) m/z: Calculated for $C_{25}H_{27}F_3N_4O_4$: 504.54. found 505.1 (M+H)+.

Example 42

3-Ethyl-6-((3-(methoxymethyl)-3-(3-(trifluoromethyl)-5,6,7,8-tetrahydro-1,6-naphthyridine-6-carbonyl)pyrrolidin-1-yl)methyl)benzo[d]oxazol-2(3H)-one

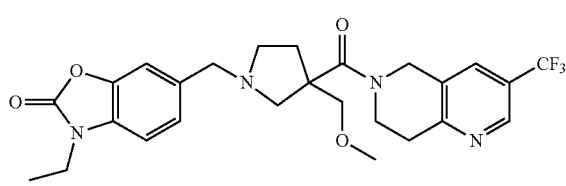 [SMILES: CCn1c(=O)oc2cc(CN3CCC(COC)(C(=O)N4CCc5ncc(C(F)(F)F)cc5C4)C3)ccc21]

The title compound was prepared according to the general procedures described in Scheme 5 using VIc (9.0 mg TFA-salt, 3% yield): $^1$H NMR (400 MHz, MeOH-d$_4$): δ 8.61 (s, 1H), 7.94 (s, 1H), 7.25 (m, 3H), 4.75 (m, 2H), 4.35 (m, 2H), 3.86 (m, 4H), 3.56 (m, 4H), 3.43 (s, 3H), 3.15 (m, 2H), 2.99 (m, 2H), 2.30 (m, 2H), 1.28 (t, 3H); $^1$H NMR (400 MHz, DMSO-d$_6$): δ 8.79 (s, 1H), 8.16 (s, 1H), 7.45 (m, 2H), 7.28 (m, 1H), 4.79 (m, 2H), 4.42 (m, 2H), 3.85 (m, 5H), 3.75-3.35 (m, 4H), 3.34-2.92 (m, 7H), 2.30-2.05 (m, 1H), 1.28 (t, 3H); MS (ESI) m/z: Calculated for $C_{26}H_{29}F_3N_4O_4$: 518.2. found 519.2 (M+H)+.

Example 43

5-Bromo-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

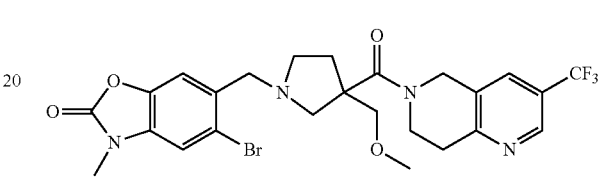

The title compound was prepared according to the general procedures described in Scheme 5 using VIc (45.0 mg TFA-salt, 3% yield): $^1$H NMR (300 MHz, MeOH-d$_4$): δ 8.61 (s, 1H), 7.94 (s, 1H), 7.61 (s, 1H), 7.36 (s, 1H), 4.76 (m, 2H), 4.54 (m, 2H), 3.86 (m, 2H), 3.60 (m, 3H), 3.45 (m, 3H), 3.33 (s, 3H), 3.25 (m, 3H), 3.01 (m, 2H), 2.54 (m, 2H); $^1$H NMR (300 MHz, DMSO-d$_6$): δ 8.79 (s, 1H), 8.17 (s, 1H), 7.86 (s, 1H), 7.58 (s, 1H), 4.81 (m, 2H), 4.70-4.30 (m, 3H), 3.88 (m, 3H), 3.80-3.50 (m, 4H), 3.34 (m, 3H), 3.30-3.10 (m, 3H), 3.01 (m, 2H), 2.60-2.20 (m, 2H); MS (ESI) m/z: Calculated for $C_{25}H_{26}BrF_3N_4O_4$: 582.1. found 583.2 (M+H)+.

Example 44

6-((3-(Methoxymethyl)-3-(3-(trifluoromethyl)-5,6,7,8-tetrahydro-1,6-naphthyridine-6-carbonyl)pyrrolidin-1-yl)methyl)-3,5-dimethylbenzo[d]oxazol-2(3H)-one

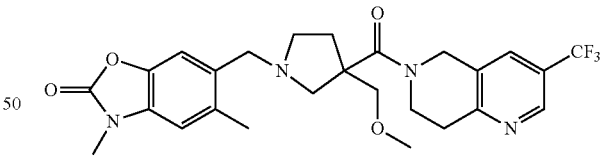

5-Bromo-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one (30 mg, 0.04 mmol) was dissolved in THF under nitrogen in a microwave tube. Methylzinc chloride (0.06 mL of a 2M solution, 0.12 mmol) and Pd(PtBu$_3$)$_2$ (1 mg, 0.002 mmol) were added. The reaction mixture was purged with nitrogen for 5 min and subsequently heated at 100° C. for 30 min under microwave irradiation (Personal Chemistry Emrys™ Optimizer). Upon completion of the reaction the mixture was diluted with ethyl acetate, washed with 1N HCl aqueous solution, brine and filtered through celite. The filtrate was dried over Na$_2$SO$_4$ and concentrated. The residue was purified by preparative HPLC to give the pure product (1 mg TFA-salt, 19% yield): $^1$H NMR (400 MHz, MeOH-d$_4$): δ 8.72 (s, 1H), 8.05 (s, 1H), 7.28 (m, 2H), 4.52 (m, 4H), 3.97 (m, 4H), 3.70 (m, 4H), 3.53-3.50 (m, 5H), 3.20-3.10 (m, 3H), 2.70-2.50 (m, 2H) 2.51 (s, 3H); MS (ESI) m/z: Calculated for C$_{26}$H$_{29}$F$_3$N$_4$O$_4$: 518.2. found 519.2 (M+H)$^+$.

Example 45

5-((3-(Ethoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

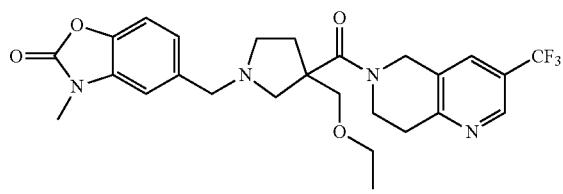 [SMILES: CCOCC1(C(=O)N2CCc3ncc(C(F)(F)F)cc3C2)CCN(Cc2ccc3oc(=O)n(C)c3c2)C1]

The title compound was prepared according to the general procedures described in Scheme 5 (110.0 mg): $^1$H NMR (400 MHz, CDCl$_3$): δ 8.69 (s, 1H), 7.64 (s, 1H), 7.58 (s, 1H), 7.13-6.94 (m, 3H), 4.60-4.03 (m, 2H), 3.83-3.78 (m, 1H), 3.62 (s, 3H), 3.58-3.55 (m, 2H), 3.40-3.26 (m, 5H), 3.10-3.03 (m, 2H), 2.96-2.93 (m, 1H), 2.78-2.73 (m, 2H), 2.55-2.46 (m, 1H), 2.30-2.23 (m, 1H), 2.09-2.02 (m, 1H), 1.02-0.98 (m, 3H); MS (ESI) m/z: Calculated for C$_{26}$H$_{29}$F$_3$N$_4$O$_4$: 518.53. found 519.2 (M+H)$^+$.

Example 46

Hydrochloride salt of 5-((3-(methoxymethyl)-3-(7-(trifluoromethyl)-1,2,3,4-tetrahydroisoquinoline-2-carbonyl)pyrrolidin-1-yl)methyl)-3-methylbenzo[d]oxazol-2(3H)-one

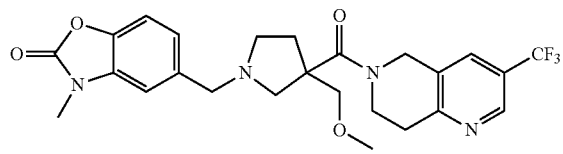 [SMILES: COCC1(C(=O)N2CCc3ncc(C(F)(F)F)cc3C2)CCN(Cc2ccc3oc(=O)n(C)c3c2)C1]

The title compound was prepared according to the general procedures described in Scheme 5 using VIc (100.0 mg): $^1$H NMR (400 MHz, DMSO-d$_6$): δ 7.69-7.61 (m, 2H), 7.55-7.51 (m, 2H), 7.00-6.92 (m, 2H), 4.80-4.63 (m, 2H), 4.40-4.32 (m, 2H), 3.80-3.60 (m, 4H), 3.50-3.40 (m, 2H), 3.38 (s, 3H), 3.36 (s, 3H), 3.20-3.01 (m, 2H), 2.95-2.88 (m, 1H), 2.77-2.74 (m, 1H), 2.44-2.41 (m, 1H), 2.30-2.20 (m, 1H); MS (ESI) m/z: Calculated for C$_{26}$H$_{28}$F$_3$N$_3$O$_4$: 503.51. found 504.2 (M+H)$^+$.

Example 47

Hydrochloride salt of 5-((3-isopropyl-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

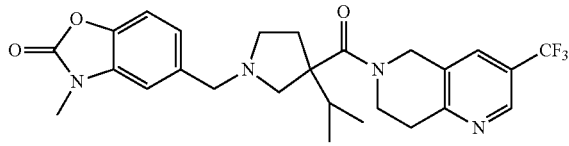 [SMILES: CC(C)C1(C(=O)N2CCc3ncc(C(F)(F)F)cc3C2)CCN(Cc2ccc3oc(=O)n(C)c3c2)C1]

The title compound was prepared according to the general procedures described in Scheme 5 (48.5 mg): $^1$H NMR (400 MHz, DMSO-d$_6$): δ 8.76 (s, 1H), 8.16 (s, 1H), 7.47-7.32 (m, 3H), 4.82-4.79 (m, 2H), 4.45-4.19 (m, 2H), 3.83-3.79 (m, 2H), 3.40-3.35 (m, 2H), 3.54 (s, 3H), 3.00-2.85 (m, 4H), 2.59-2.56 (m, 2H), 2.22-2.03 (m, 1H), 0.98 (d, 6H); MS (ESI) m/z: Calculated for C$_{26}$H$_{29}$F$_3$N$_4$O$_3$: 502.53. found 503.1 (M+H)$^+$.

Example 48

Hydrochloride salt of 2-(1-((3-methyl-2-oxo-2,3-dihydrobenzo[d]oxazol-5-yl)methyl)-3-(3-(trifluoromethyl)-5,6,7,8-tetrahydro-1,6-naphthyridine-6-carbonyl)pyrrolidin-3-yl)acetonitrile

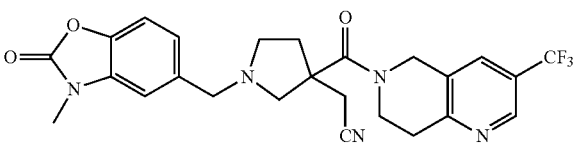 [SMILES: Cn1c(=O)oc2ccc(CN3CCC(CC#N)(C(=O)N4CCc5ncc(C(F)(F)F)cc5C4)C3)cc21]

The title compound was prepared according to the general procedures described in Scheme 5 (480.0 mg): $^1$H NMR (400 MHz, DMSO-d$_6$): δ 8.80 (s, 1H), 8.20 (s, 1H), 7.61-7.61-7.30 (m, 3H), 4.81-4.79 (m, 2H), 4.50-4.39 (m, 2H), 3.90-3.80 (m, 2H), 3.60-3.44 (m, 2H), 3.39 (s, 3H), 3.20-3.00 (m, 2H), 2.85-2.79 (m, 3H), 2.45-2.25 (m, 1H), 2.35-2.20 (m, 1H), 2.30-2.20 (m, 1H); MS (ESI) m/z: Calculated for C$_{25}$H$_{24}$F$_3$N$_5$O$_3$: 499.48. found 500.3 (M+H)$^+$.

Example 49

5-((3-(Hydroxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one

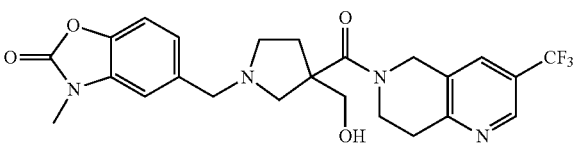

To a stirred solution of compound from Example 39 (770 mg, 1.52 mmol) in 14 mL of DCM at −78° C. was added a solution of BBr$_3$ (4.58 mmol) in DCM. After 1 hour, the reaction mixture was warned up to −25° C. and the reaction was monitored by TLC. After completion, the mixture was quenched with sat. NaHCO₃. The organic layer was separated and the aqueous layer was extracted with ethyl acetate (3×100 mL). The combinated organic layer were washed with brine, dried over MgSO₄ and concentrated to gave the crude product, which was purified by a flash column chromatography give 172 mg of the title compound (0.351 mmol, 23%): $^1$H NMR (400 MHz, CD₃OD): δ 8.63 (s, 1H), 7.89 (s, 1H), 7.20-7.15 (m, 3H), 4.83-4.79 (m, 2H), 4.15-3.85 (m, 2H), 3.81-3.60 (m, 2H), 3.40 (s, 2H), 3.35 (s, 3H), 3.30-3.00 (m, 3H), 2.80-2.60 (m, 3H), 2.32-2.20 (m, 1H), 2.10-1.99 (m, 1H); MS (ESI) m/z: Calculated for $C_{24}H_{25}F_3N_4O_4$: 490.47. found 491.1 (M+H)⁺.

Example 50 and 51

(3-(Methoxymethyl)-1-(4-(6-methoxypyridin-3-yl)cyclohexyl)pyrrolidin-3-yl)(3-(trifluoromethyl)-7,8-dihydro-1,6-naphthyridin-6(5H)-yl)methanone

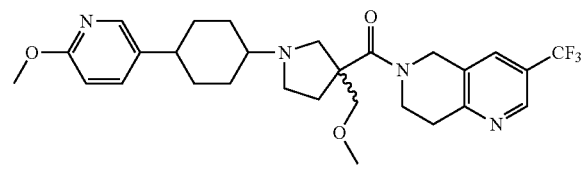 [SMILES: COCC1(C(=O)N2CCc3ncc(C(F)(F)F)cc3C2)CCN(C2CCC(c3ccc(OC)nc3)CC2)C1]

The title compound was prepared according to the procedures described in Scheme 8 (Step 2) using compounds from Examples 52 and 53: The crude product was obtained as a mixture of isomers which were further separated by reverse phase preparative HPLC to yield isomer I and isomer II.

Isomer I (1.3 mg): $^1$H NMR (300 MHz, CDCl₃): δ 8.70 (s, 1H), 8.00 (s, 1H), 7.67 (s, 1H), 7.42 (m, 1H), 6.68 (d, 1H), 4.89 (m, 2H), 3.91 (m, 2H), 3.50 (m, 3H), 3.26 (s, 3H), 3.11 (s, 3H), 2.75 (m, 3H), 2.258 (m, 8H), 1.50 (m, 6H); MS (ESI) m/z: Calculated for $C_{28}H_{35}F_3N_4O_3$: 532.60. found: 533.4 (M+H)⁺.

Isomer II (16.1 mg): $^1$H NMR (300 MHz, CDCl₃): δ 8.70 (s, 1H), 8.00 (s, 1H), 7.67 (s, 1H), 7.42 (m, 1H), 6.68 (d, 1H), 4.89 (m, 2H), 3.91 (m, 2H), 3.50 (m, 3H), 3.26 (s, 3H), 3.11 (s, 3H), 2.75 (m, 3H), 2.258 (m, 8H), 1.50 (m, 6H); MS (ESI) m/z: Calculated for $C_{28}H_{35}F_3N_4O_3$: 532.60. found: 533.2 (M+H)⁺.

Example 52 and 53

(1-(4-Hydroxy-4-(pyrimidin-5-yl)cyclohexyl)-3-(methoxymethyl)pyrrolidin-3-yl)(3-(trifluoromethyl)-7,8-dihydro-1,6-naphthyridin-6(5H)-yl)methanone

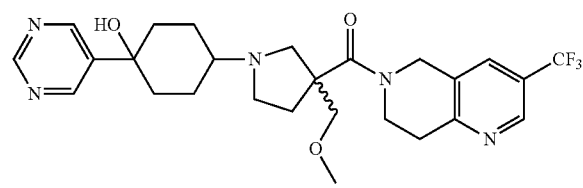 [SMILES: COCC1(C(=O)N2CCc3ncc(C(F)(F)F)cc3C2)CCN(C2CCC(O)(c3cncnc3)CC2)C1]

The title compound was prepared according to the procedure in Examples 30 and 31 (Scheme 8). The crude product was obtained as a mixture of isomers which were further separated by reverse phase preparative HPLC to yield isomer I and isomer II.

Isomer I: MS (ESI) m/z: Calculated for $C_{26}H_{32}F_3N_5O_3$: 519.56. found: 520 (M+H)⁺.

Isomer II: MS (ESI) m/z: Calculated for $C_{26}H_{32}F_3N_5O_3$: 519.56. found: 520 (M+H)⁺.

Example 54 and 55

(3-(Methoxymethyl)-1-(4-(pyrimidin-5-yl)cyclohexyl)pyrrolidin-3-yl)(3-(trifluoromethyl)-7,8-dihydro-1,6-naphthyridin-6(5H)-yl)methanone

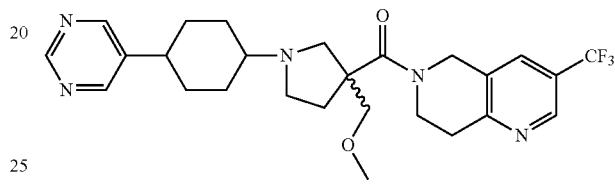

The title compound was prepared according to the procedures described in Scheme 8 (Step 2) using compounds from Examples 52 and 53. The crude product was obtained as a mixture of isomers which were further separated by reverse phase preparative HPLC to yield isomer I and isomer II.

Isomer I (33.8 mg): $^1$H NMR (400 MHz, CD₃OD): δ 8.89 (s, 1H), 8.74-8.70 (m, 2H), 8.69 (s, 1H), 8.10 (s, 1H), 4.85-4.82 (m, 2H), 4.10-3.90 (m, 2H), 3.70-3.57 (m, 2H), 3.40 (s, 3H), 3.00-2.70 (m, 4H), 2.55-2.12 (m, 3H), 2.10-1.90 (m, 5H), 1.80-1.65 (m, 4H), 1.40-1.25 (m, 2H); MS (ESI) m/z: Calculated for $C_{26}H_{32}F_3N_5O_2$: 503.55. found: 504 (M+H)⁺.

Isomer II: $^1$H NMR (400 MHz, CD₃OD): δ 8.99 (s, 1H), 8.71 (s, 2H), 8.68 (s, 1H), 8.01 (s, 1H), 4.90 (m, 2H), 4.05 (m, 1H), 3.94 (m, 1H), 3.60 (m, 2H), 3.30-1.35 (m, 23H); MS (ESI) m/z: Calculated for $C_{26}H_{32}F_3N_5O_2$: 503.56. found: 504 (M+H)⁺.

Example 56 and 57

(1-(4-(4-Fluorophenyl)cyclohexyl)-3-(methoxymethyl)pyrrolidin-3-yl)(3-(trifluoromethyl)-7,8-dihydro-1,6-naphthyridin-6(5H)-yl)methanone

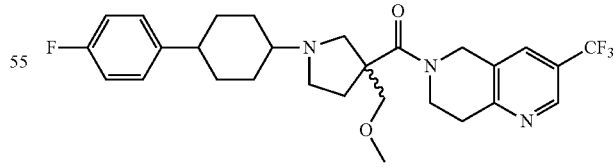

The title compounds were prepared according to the general procedures described in Scheme 8. The crude product was obtained as a mixture of isomers which were further separated by reverse phase preparative HPLC to yield isomer I and isomer II.

Isomer I (60 mg): $^1$H NMR (400 MHz, CD₃OD): δ 8.95 (d, 1H), 8.43 (d, 1H), 7.41 (m, 2H), 7.01 (m, 2H), 4.90 (m, 2H), 4.65 (m, 1H), 4.05 (m, 3H), 3.72 (m, 4H), 3.45-1.70 (m, 17H); MS (ESI) m/z: Calculated for $C_{28}H_{33}F_4N_3O_2$: 519.57. found: 520 (M+H)+.

Isomer II: (30 mg): $^1$H NMR (400 MHz, CD$_3$OD): δ 8.83 (s, 1H), 8.24 (s, 1H), 7.23 (m, 2H), 7.01 (m, 2H), 4.90 (m, 2H), 4.61 (m, 1H), 4.00 (m, 3H), 3.72 (m, 4H), 3.45-1.60 (m, 17H); MS (ESI) m/z: Calculated for $C_{28}H_{33}F_4N_3O_2$: 519.57. found: 520 (M+H)+.

Example 58

6-((4-Isobutyl-4-(3-(trifluoromethyl)-5,6,7,8-tetrahydro-1,6-naphthyridine-6-carbonyl)piperidin-1-yl)methyl)-3-methylbenzo[d]thiazol-2(3H)-one di-TFA salt

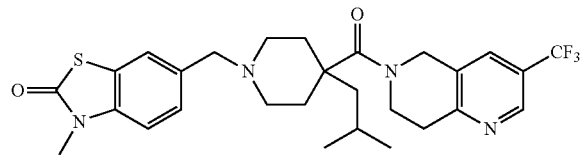 [SMILES: CC(C)CC1(C(=O)N2CCc3ncc(C(F)(F)F)cc3C2)CCN(Cc2ccc3c(c2)sc(=O)n3C)CC1]

The title compound was prepared according to the general procedures described in Scheme 4 (15 mg, 4.5% yield): $^1$H NMR (400 MHz, DMSO-d$_6$): δ 9.56 (bs, 2H), 8.77 (s, 1H), 8.22 (s, 1H), 7.79-7.73 (m, 1H), 7.43 (s, 1H), 7.30 (d, 1H), 5.00-4.84 (m, 2H), 4.31-4.30 (m, 2H), 4.02-3.90 (m, 2H), 3.48 (s, 3H), 3.34-2.80 (m, 6H), 2.20-1.31 (m, 7H), 0.90-0.80 (m, 6H); MS (ESI) m/z: Calculated for $C_{28}H_{33}F_3N_4O_2S$: 546.65. found 547 (M+H)+.

Example 59

6-((4-Isobutyl-4-(3-(trifluoromethyl)-5,6,7,8-tetrahydro-1,6-naphthyridine-6-carbonyl)piperidin-1-yl)methyl)-3-methylbenzo[d]oxazol-2(3H)-one

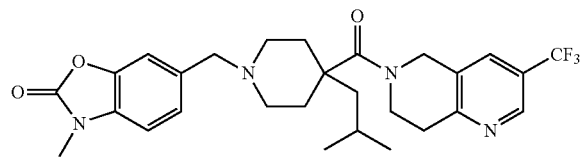 [SMILES: CC(C)CC1(C(=O)N2CCc3ncc(C(F)(F)F)cc3C2)CCN(Cc2ccc3c(c2)oc(=O)n3C)CC1]

The title compound was prepared according to the general procedures described in Scheme 4 (48 mg): $^1$H NMR (400 MHz, DMSO-d$_6$): δ 8.62 (s, 1H), 7.97 (s, 1H), 7.24-7.13 (m, 3H), 4.80 (m, 2H), 4.20 (s, 2H), 3.94 (s, 2H), 3.32 (m, 5H), 3.10 (m, 4H), 2.56 (d, 2H), 1.59 (m, 4H), 0.713 (m, 6H); MS (ESI) m/z: Calculated for $C_{28}H_{33}F_3N_4O_3$: 530.58. found 531.2 (M+H)+.

Example 60

The biological activity of the compounds described herein can be evaluated using assays known in the art, such as the AequoScreen™ assay.

General Procedures for AequoScreen™ Assay:

AequoScreen™ CCR2b (FAST-060A) cells grown to mid-log phase in culture media without antibiotics are detached with PBS-EDTA, centrifuged and resuspended in assay buffer (DMEM/HAM's F12 with HEPES, without phenol red+0.1% BSA protease free) at a concentration of $1×10^6$ cells/mL. Cells are incubated at room temperature for at least 4 hours with coelenterazine h. Dose response curves are performed before testing. The reference agonist is MCP-1.

For agonist testing, 50 μL of cell suspension is mixed with 50 μL of test compound in a 96-well plate. The resulting emission of light is recorded using a Hamamatsu Functional Drug Screening System 6000 (FDSS 6000).

Following an incubation of 15 minutes after the first injection, 100 μL of the resulting cell suspension containing the test compound is mixed with 100 μL of the reference agonist in the 96 well test plate. The resulting emission of light is recorded using the same luminometer as for agonist testing.

To standardize the emission of recorded light (determination of the "100% signal") across plates and across different experiments, some of the wells contained 100 μM digitonin, a saturating concentration of ATP (20 μM) and a concentration of reference agonist equivalent to the $EC_{50}$ obtained during test validation.

Agonist activity of a test compound can be expressed as a percentage of the activity of the reference agonist at its $EC_{100}$ concentration. Antagonist activity of a test compound can be expressed as a percentage of the inhibition of reference agonist activity at its $EC_{80}$ concentration.

Results:

Biological activity data for several compounds collected using the above method is provided in Table 2.

TABLE 2

| Example No. | Structure | $IC_{50}$ (μM) Ca++ flux |
|---|---|---|
| 1 | 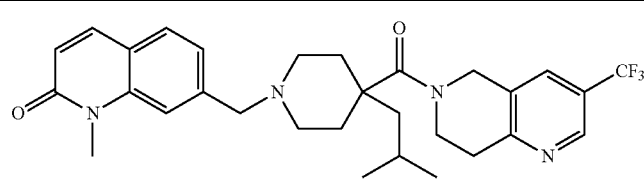 | ++ |

TABLE 2-continued

| Example No. | Structure | IC$_{50}$ (μM) Ca$^{++}$ flux |
|---|---|---|
| 2 | 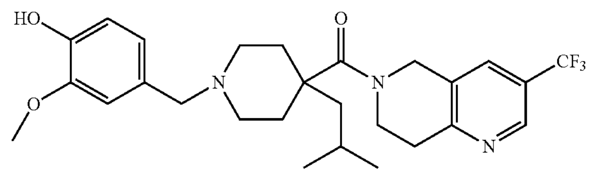 [SMILES: COc1cc(CN2CCC(CC(C)C)(C(=O)N3CCc4ncc(C(F)(F)F)cc4C3)CC2)ccc1O] | + |
| 3 | 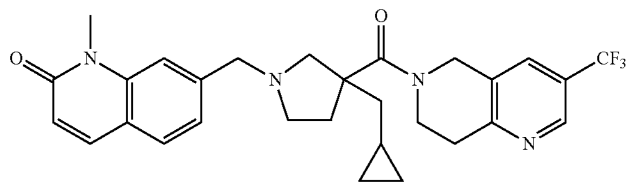 [SMILES: Cn1c(=O)ccc2ccc(CN3CCC(CC4CC4)(C(=O)N4CCc5ncc(C(F)(F)F)cc5C4)C3)cc21] | +++ |
| 4, 5 (Enantiomer I) | 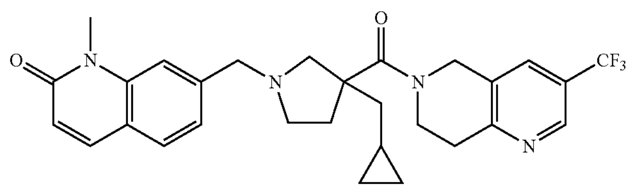 [SMILES: Cn1c(=O)ccc2ccc(CN3CCC(CC4CC4)(C(=O)N4CCc5ncc(C(F)(F)F)cc5C4)C3)cc21] | +++ |
| 4, 5 (Enantiomer II) | 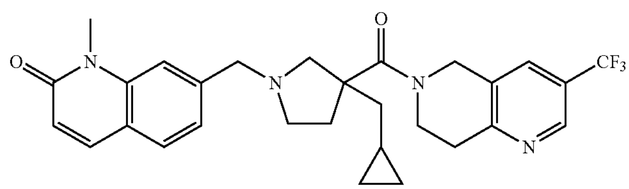 [SMILES: Cn1c(=O)ccc2ccc(CN3CCC(CC4CC4)(C(=O)N4CCc5ncc(C(F)(F)F)cc5C4)C3)cc21] | +++ |
| 6 | 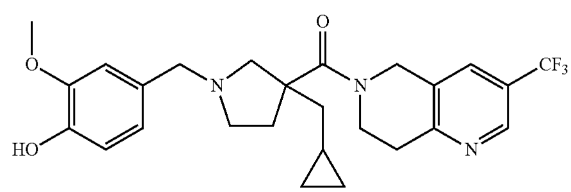 [SMILES: COc1cc(CN2CCC(CC3CC3)(C(=O)N3CCc4ncc(C(F)(F)F)cc4C3)C2)ccc1O] | ++ |
| 7 | 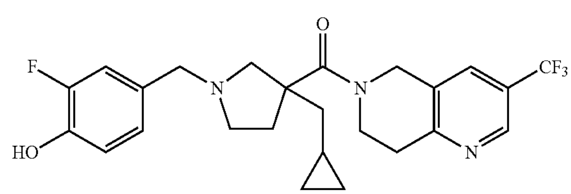 [SMILES: O=C(N1CCc2ncc(C(F)(F)F)cc2C1)C1(CC2CC2)CCN(Cc2ccc(O)c(F)c2)C1] | + |
| 8 | 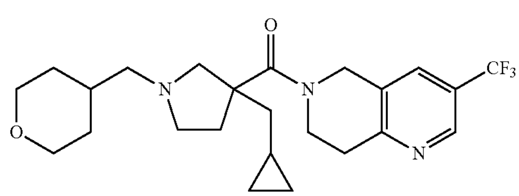 [SMILES: O=C(N1CCc2ncc(C(F)(F)F)cc2C1)C1(CC2CC2)CCN(CC2CCOCC2)C1] | ++ |
| 25 | 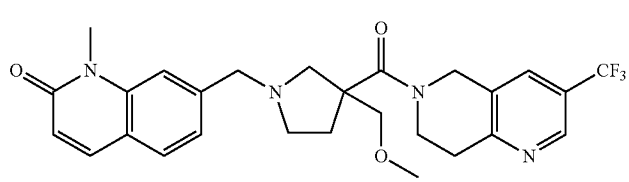 [SMILES: COCC1(C(=O)N2CCc3ncc(C(F)(F)F)cc3C2)CCN(Cc2ccc3ccc(=O)n(C)c3c2)C1] | +++ |

TABLE 2-continued

| Example No. | Structure | IC$_{50}$ (μM) Ca$^{++}$ flux |
|---|---|---|
| 9 | 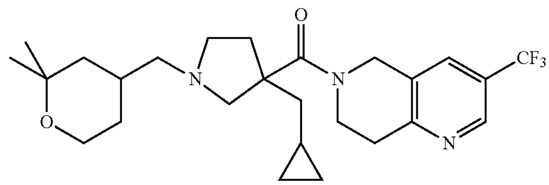 [SMILES: CC1(C)CC(CN2CCC(CC3CC3)(C(=O)N3CCc4ncc(C(F)(F)F)cc4C3)C2)CCO1] | ++ |
| 17 | 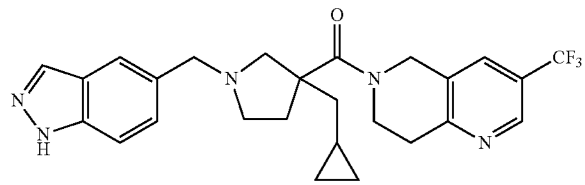 [SMILES: O=C(N1CCc2ncc(C(F)(F)F)cc2C1)C1(CC2CC2)CCN(Cc2ccc3[nH]ncc3c2)C1] | + |
| 10 | 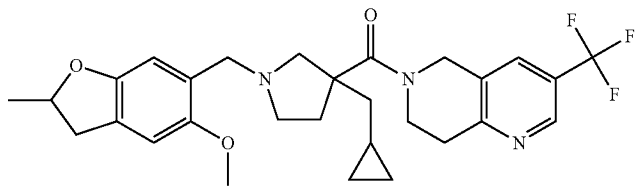 [SMILES: COc1cc2c(cc1CN1CCC(CC3CC3)(C(=O)N3CCc4ncc(C(F)(F)F)cc4C3)C1)OC(C)C2] | + |
| 26, 27 (Enantiomer II) | 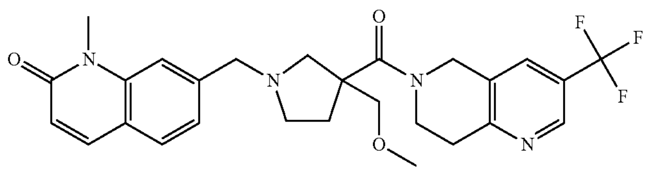 [SMILES: COCC1(C(=O)N2CCc3ncc(C(F)(F)F)cc3C2)CCN(Cc2ccc3ccc(=O)n(C)c3c2)C1] | + |
| 26, 27 (Enantiomer I) | 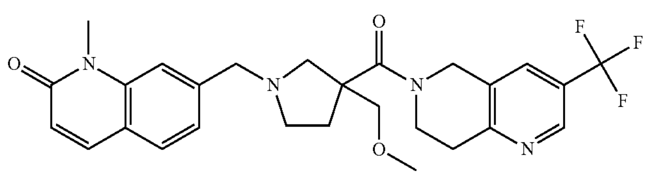 [SMILES: COCC1(C(=O)N2CCc3ncc(C(F)(F)F)cc3C2)CCN(Cc2ccc3ccc(=O)n(C)c3c2)C1] | +++ |
| 11 | 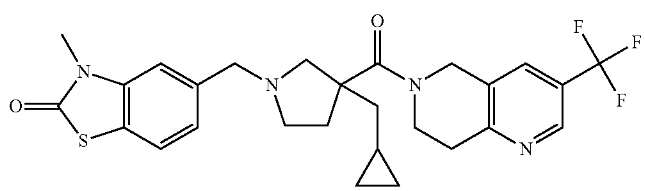 [SMILES: Cn1c(=O)sc2ccc(CN3CCC(CC4CC4)(C(=O)N4CCc5ncc(C(F)(F)F)cc5C4)C3)cc21] | +++ |
| 12 | 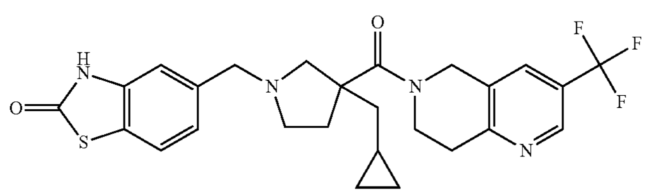 [SMILES: O=C(N1CCc2ncc(C(F)(F)F)cc2C1)C1(CC2CC2)CCN(Cc2ccc3sc(=O)[nH]c3c2)C1] | ++ |
| 22 | 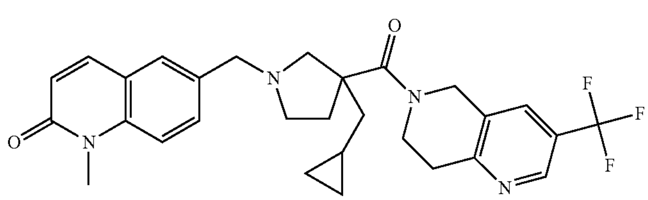 [SMILES: Cn1c(=O)ccc2cc(CN3CCC(CC4CC4)(C(=O)N4CCc5ncc(C(F)(F)F)cc5C4)C3)ccc21] | + |

TABLE 2-continued
| Example No. | Structure | IC$_{50}$ (μM) Ca$^{++}$ flux |
|---|---|---|
| 23 | 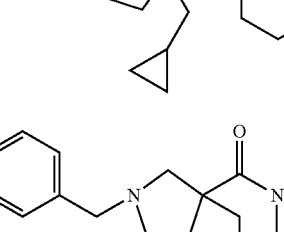 | +++ |
| 15 | 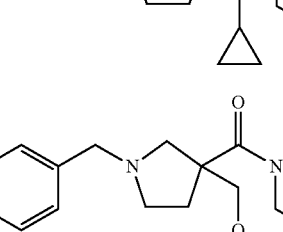 | + |
| 28 | 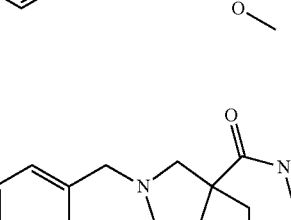 | +++ |
| 39 | 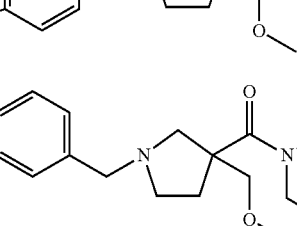 | +++ |
| 32 | 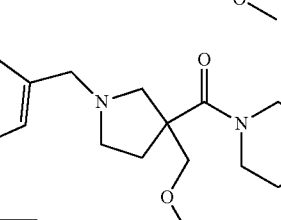 | +++ |
| 42 | 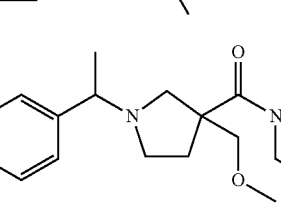 | +++ |
| 29 | 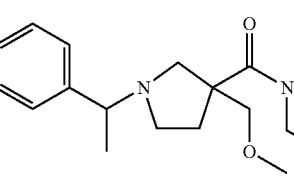 | +++ |
| 33 | 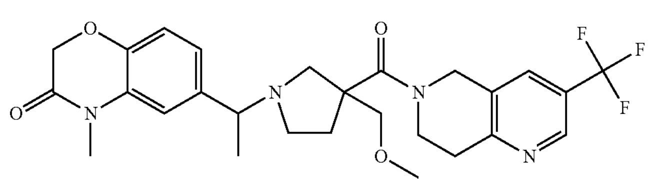 [SMILES: COCC1(C(=O)N2CCc3ncc(C(F)(F)F)cc3C2)CCN(C(C)c2ccc3c(c2)N(C)C(=O)CO3)C1] | +++ |

TABLE 2-continued

| Example No. | Structure | IC$_{50}$ (µM) Ca$^{++}$ flux |
|---|---|---|
| 36 | 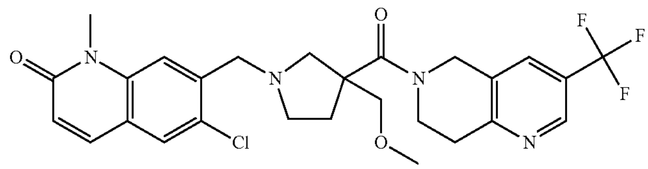 [SMILES: COCC1(C(=O)N2CCc3ncc(C(F)(F)F)cc3C2)CCN(Cc2cc3c(ccc(=O)n3C)cc2Cl)C1] | ++ |
| 34 | 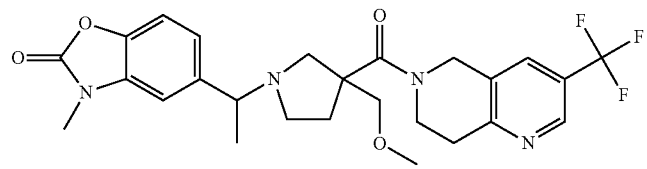 [SMILES: COCC1(C(=O)N2CCc3ncc(C(F)(F)F)cc3C2)CCN(C(C)c2ccc3oc(=O)n(C)c3c2)C1] | +++ |
| 40, 41 (Enantiomer I) | 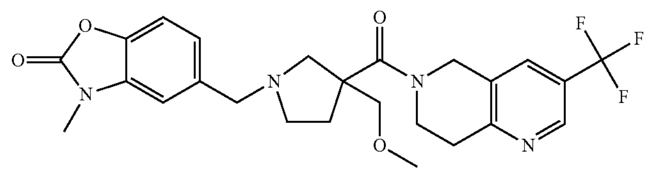 | +++ |
| 40, 41 (Enantiomer II) | 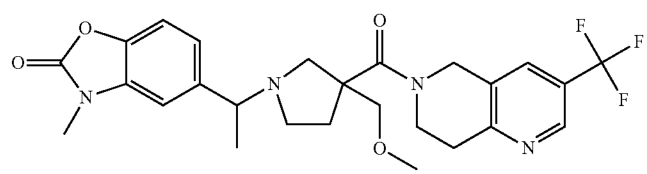 [SMILES: COCC1(C(=O)N2CCc3ncc(C(F)(F)F)cc3C2)CCN(C(C)c2ccc3oc(=O)n(C)c3c2)C1] | ++ |
| 37 | 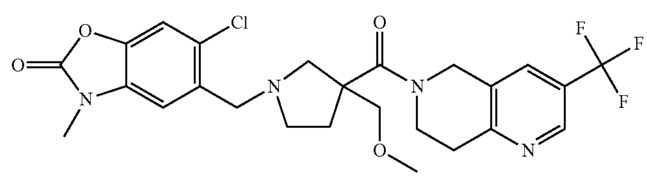 [SMILES: COCC1(C(=O)N2CCc3ncc(C(F)(F)F)cc3C2)CCN(Cc2cc3c(cc2Cl)oc(=O)n3C)C1] | +++ |
| 38 | 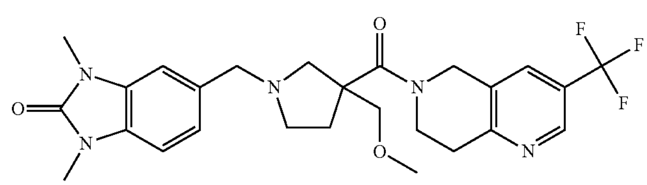 [SMILES: COCC1(C(=O)N2CCc3ncc(C(F)(F)F)cc3C2)CCN(Cc2ccc3c(c2)n(C)c(=O)n3C)C1] | + |
| 43 | 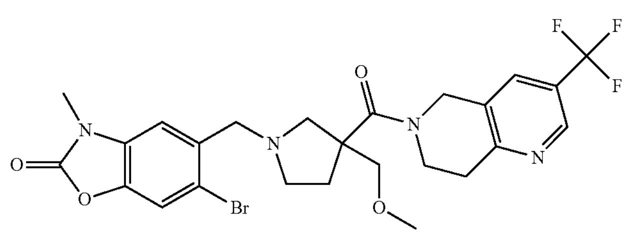 [SMILES: COCC1(C(=O)N2CCc3ncc(C(F)(F)F)cc3C2)CCN(Cc2cc3c(cc2Br)oc(=O)n3C)C1] | +++ |
| 44 | 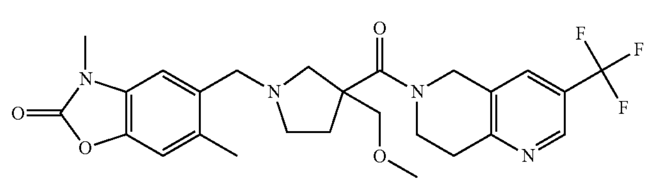 [SMILES: COCC1(C(=O)N2CCc3ncc(C(F)(F)F)cc3C2)CCN(Cc2cc3c(cc2C)oc(=O)n3C)C1] | +++ |

TABLE 2-continued

| Example No. | Structure | IC$_{50}$ (µM) Ca$^{++}$ flux |
|---|---|---|
| 35 | 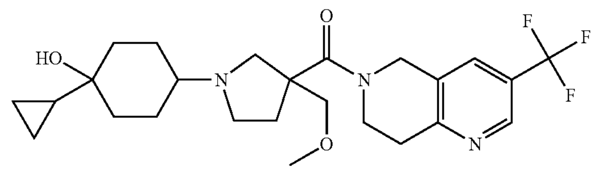 [SMILES: COCC1(C(=O)N2CCc3ncc(C(F)(F)F)cc3C2)CCN(C2CCC(O)(C3CC3)CC2)C1] | ++ |
| 30, 31 (Isomer I) | 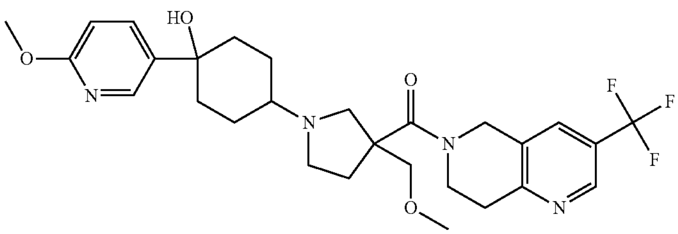 [SMILES: COCC1(C(=O)N2CCc3ncc(C(F)(F)F)cc3C2)CCN(C2CCC(O)(c3ccc(OC)nc3)CC2)C1] | +++ |
| 30, 31 (Isomer II) | 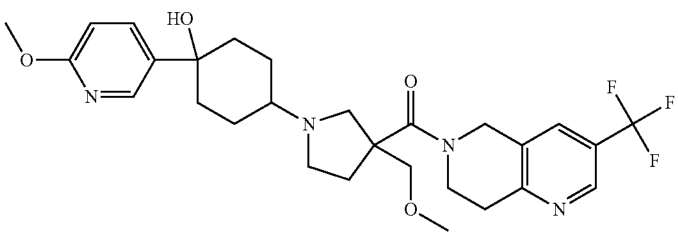 [SMILES: COCC1(C(=O)N2CCc3ncc(C(F)(F)F)cc3C2)CCN(C2CCC(O)(c3ccc(OC)nc3)CC2)C1] | + |
| 16 | 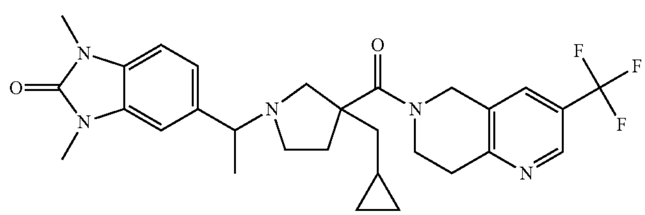 [SMILES: CC(c1ccc2c(c1)n(C)c(=O)n2C)N1CCC(CC2CC2)(C(=O)N2CCc3ncc(C(F)(F)F)cc3C2)C1] | + |
| 24 | 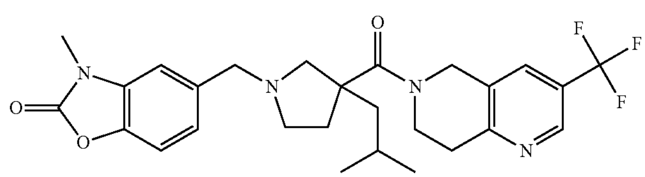 [SMILES: CC(C)CC1(C(=O)N2CCc3ncc(C(F)(F)F)cc3C2)CCN(Cc2ccc3oc(=O)n(C)c3c2)C1] | +++ |
| 45 | 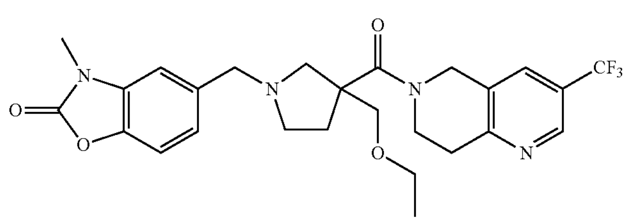 [SMILES: CCOCC1(C(=O)N2CCc3ncc(C(F)(F)F)cc3C2)CCN(Cc2ccc3oc(=O)n(C)c3c2)C1] | +++ |
| 46 | 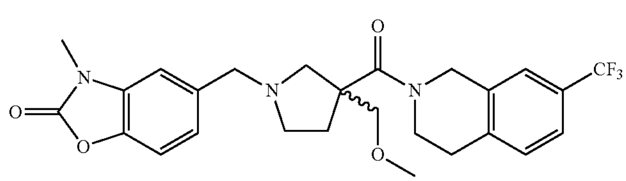 [SMILES: COCC1(C(=O)N2CCc3ccc(C(F)(F)F)cc3C2)CCN(Cc2ccc3oc(=O)n(C)c3c2)C1] | +++ |

TABLE 2-continued

| Example No. | Structure | IC$_{50}$ (μM) Ca$^{++}$ flux |
|---|---|---|
| 47 | 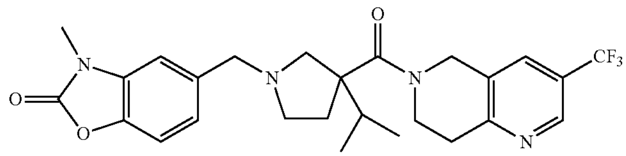 [SMILES: CC(C)C1(C(=O)N2CCc3ncc(C(F)(F)F)cc3C2)CCN(Cc2ccc3oc(=O)n(C)c3c2)C1] | +++ |
| 48 | 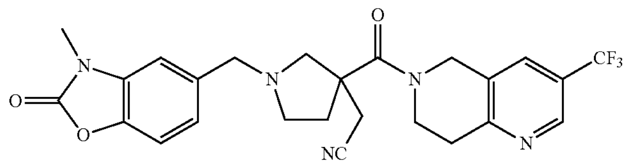 [SMILES: Cn1c(=O)oc2ccc(CN3CCC(CC#N)(C(=O)N4CCc5ncc(C(F)(F)F)cc5C4)C3)cc21] | ++ |
| 49 | 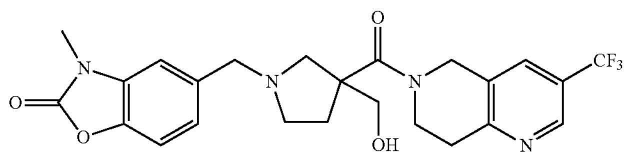 [SMILES: Cn1c(=O)oc2ccc(CN3CCC(CO)(C(=O)N4CCc5ncc(C(F)(F)F)cc5C4)C3)cc21] | + |
| 50, 51 (Isomer I) | 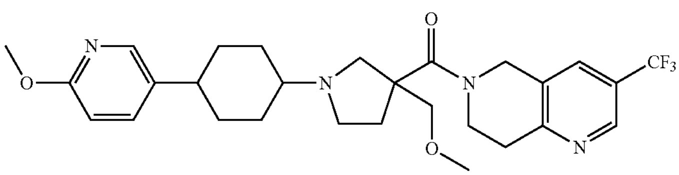 [SMILES: COCC1(C(=O)N2CCc3ncc(C(F)(F)F)cc3C2)CCN(C2CCC(c3ccc(OC)nc3)CC2)C1] | +++ |
| 50, 51 (Isomer II) | 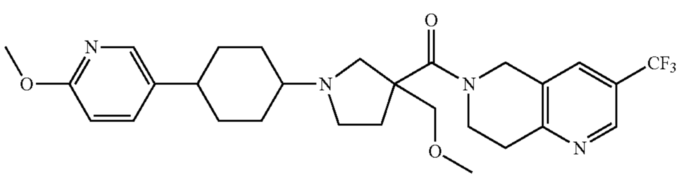 [SMILES: COCC1(C(=O)N2CCc3ncc(C(F)(F)F)cc3C2)CCN(C2CCC(c3ccc(OC)nc3)CC2)C1] | +++ |
| 52, 53 (Isomer II) | | ++ |
| 52, 53 (Isomer II) | | + |
| 54, 55 (Isomer II) | | ++ |
| 54, 55 (Isomer II) | | ++ |

TABLE 2-continued

| Example No. | Structure | IC$_{50}$ (μM) Ca$^{++}$ flux |
|---|---|---|
| 56, 57 (Isomer I) | | +++ |
| 56, 57 (Isomer I) | | +++ |
| 58 | | + | a. when IC$_{50}$ > 1000 nM: designated as "+"; when 1000 nM > IC$_{50}$ > 200 nM; designated as "++"; when IC$_{50}$ < 200 nM, designated as "+++".

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference for all purposes. The appropriate components, processes, and methods of those patents, applications and other documents may be selected for the invention and embodiments thereof.

The invention claimed is:
1. A compound of formula I-A:

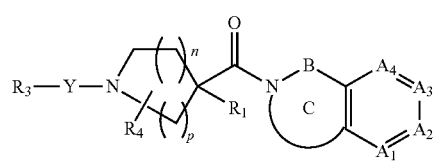

(I-A)

or a pharmaceutically acceptable salt thereof, wherein:
$R_1$ is hydrogen; alkyl, alkoxyalkyl, alkoxyphenyl, alkylthioalkyl, alkylamino, —SO$_2$(alkyl), C$_{3-6}$ cycloalkyl, C$_{3-6}$ heterocycloalkyl, aryl, heteroaryl, aralkyl, or heteroaralkyl, each of which is optionally substituted with 1, 2, or 3 R$_5$ substituents; or R$_1$ is optionally substituted (C$_1$-C$_6$alkylene)-R$_{1a}$, wherein R$_{1a}$ is C$_{3-6}$ cycloalkyl, C$_{3-6}$ heterocycloalkyl, aryl, or heteroaryl, each of which is optionally substituted with 1, 2, or 3 R$_5$ substituents;

Y is a direct bond or is CO, SO$_2$, —N(H)CO, —N(H)SO$_2$, C(=NH), C$_{1-4}$ alkylene, C$_{2-4}$ alkenylene, C$_{2-4}$ alkynylene, C$_{3-6}$ cycloalkylene, arylene, heterocycloalkylene, heteroarylene, —C(O)alkylene, —N(H)C(O)alkylene, or —O-alkylene; each of which may be optionally substituted with 1, 2, or 3 R$_5$ substituents;

R$_3$ is

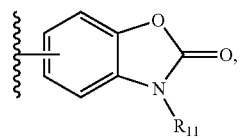

wherein R$_{11}$ is hydrogen or is C$_{1-6}$ alkyl, (C$_1$-C$_6$alkylene) cycloalkyl, aralkyl, or heteroaralkyl, any of which may be optionally substituted with halo, hydroxy, alkyl, alkenyl, cycloalkyl, C$_{1-3}$alkoxy, —CO$_2$H, —CO$_2$C$_{1-3}$alkyl, cyano, aryl, heteroaryl, —CF$_3$, —O—CF$_3$, —O—CH$_2$F, or —O—CHF$_2$;

R$_4$ is hydrogen; halo; C$_{1-8}$ alkyl, alkenyl, or alkynyl optionally interrupted by oxygen or sulfur; cycloalkyl; alkoxy; arylalkoxy; or heteroarylalkoxy;

R$_5$, when present, represents independently for each occurrence hydrogen, halo, hydroxy, alkyl, alkenyl, cycloalkyl, alkoxy, —CO$_2$H, —CO$_2$C$_{1-3}$alkyl, cyano, aryl, heteroaryl, aralkyl, heteroaralkyl, oxo, —CF$_3$, —O—CF$_3$, —O—CHF$_2$, —O—CH$_2$F, —O-aryl, —N(H)alkyl, —N(H)SO$_2$-alkyl, —N(H)C(O)alkyl, —SO$_2$N(H)alkyl, —SO$_2$N(alkyl)C(O)alkyl, or —C(O)N(H)SO$_2$alkyl;

n is 0 or 1;

p is 1;

A$_1$, A$_2$, A$_3$, and A$_4$ are independently N or C—R$_5$, provided that at least two of A$_1$, A$_2$, A$_3$, or A$_4$ are C—R$_5$; and

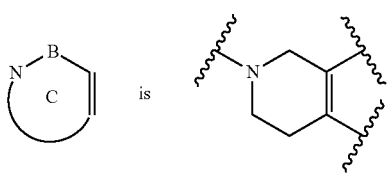 is 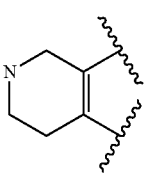

optionally substituted with 1 or 2 halo, methyl, or ethyl groups, or is geminally substituted to form a cyclopropyl ring.

2. The compound of claim 1, wherein $R_1$ is hydrogen; alkyl, alkoxyalkyl, alkoxy-$CHF_2$, alkoxy-$CH_2F$, alkoxy-$CF_3$, $C_{3-6}$ cycloalkyl, $C_{3-6}$ heterocycloalkyl, aryl, heteroaryl, or ($C_1$-$C_6$alkylene)-$R_{1a}$; wherein $R_{1a}$ is $C_{3-6}$ cycloalkyl, $C_{3-6}$ heterocycloalkyl, aryl, or heteroaryl, each of which may be independently optionally substituted with 1, 2, or 3 $R_5$ substituents.

3. The compound of claim 1, wherein $R_1$ is

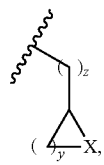

wherein z is 1, 2, or 3;

y is 1, 2, 3, or 4; and x is O, NH, $CH_2$, $CF_2$, or $N(C_{1-8}alkyl)$.

4. The compound of claim 1, wherein $R_1$ is —$CH_2$—O—$CH_3$, $CH_2$—O—$CF_3$, $CH_2$—O—$CHF_2$, $CH_2$—O—$CH_2F$, —$CH_2$—O—$CH_2$—$CH_3$, —$CH_2O$—CH—$(CH_3)_2$, or —$CH_2$—CN.

5. The compound of claim 1, wherein $R_1$ is methyl;

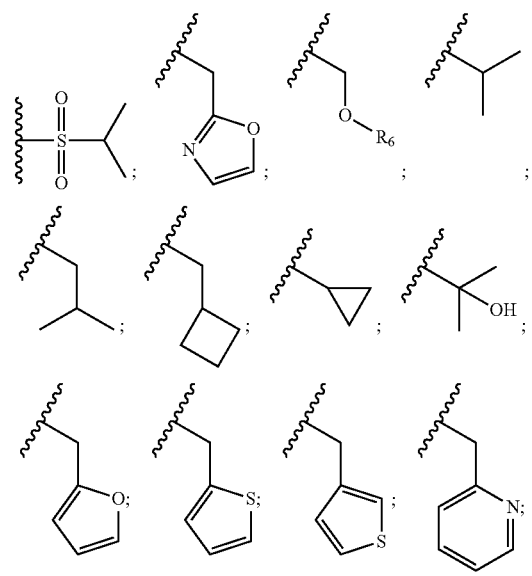

$R_6$ is alkyl;

$R_7$ represents independently for each occurrence hydrogen or $C_{1-3}$ alkyl; and $R_8$ is an alkyl group.

6. The compound of claim 1, wherein Y is $CH_2$,

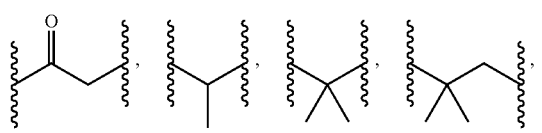

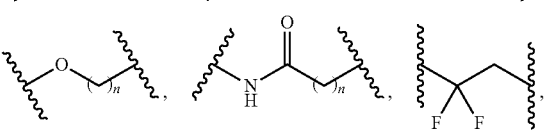

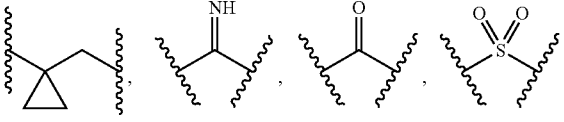

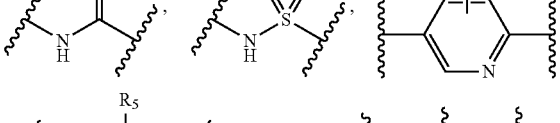

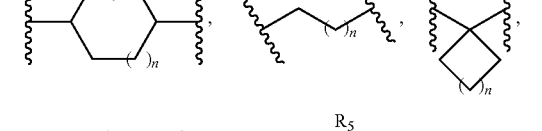

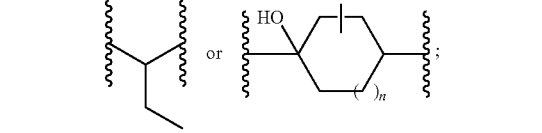

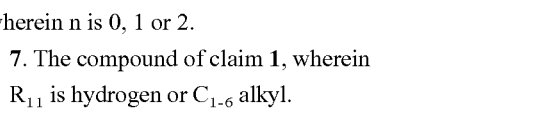

wherein n is 0, 1 or 2.

7. The compound of claim 1, wherein $R_{11}$ is hydrogen or $C_{1-6}$ alkyl.

8. A compound represented by the following formula:

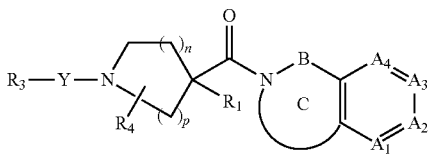

or a pharmaceutically acceptable salt thereof, wherein:
$R_1$ is hydrogen; alkyl, alkoxyalkyl, alkoxyphenyl, alkylthioalkyl, alkylamino, —$SO_2$(alkyl), $C_{3-6}$ cycloalkyl, $C_{3-6}$ heterocycloalkyl, aryl, heteroaryl, aralkyl, or heteroaralkyl, each of which is optionally substituted with 1, 2, or 3 $R_5$ substituents; or $R_1$ is optionally substituted ($C_1$-$C_6$alkylene)-$R_{1a}$, wherein $R_{1a}$ is $C_{3-6}$ cycloalkyl, $C_{3-6}$ heterocycloalkyl, aryl, or heteroaryl, each of which is optionally substituted with 1, 2, or 3 $R_5$ substituents;
Y is a direct bond or is CO, $SO_2$, —N(H)CO, —N(H)$SO_2$, C(=NH), $C_{1-4}$ alkylene, $C_{2-4}$ alkenylene, $C_{2-4}$ alkynylene, $C_{3-6}$ cycloalkylene, arylene, heterocycloalkylene, heteroarylene, —C(O)alkylene, —N(H)C(O)alkylene, or —O-alkylene; each of which may be optionally substituted with 1, 2, or 3 $R_5$ substituents;
$R_3$ is

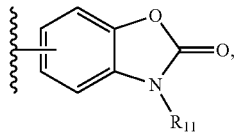

wherein $R_{11}$ is hydrogen or is $C_{1-6}$ alkyl, ($C_1$-$C_6$alkylene) cycloalkyl, aralkyl, or heteroaralkyl, any of which may be optionally substituted with halo, hydroxy, alkyl, alkenyl, cycloalkyl, $C_{1-3}$alkoxy, —$CO_2H$, —$CO_2C_{1-3}$alkyl, cyano, aryl, heteroaryl, —$CF_3$, —O—$CF_3$, —O—$CH_2F$, or —O—$CHF_2$;
$R_4$ is hydrogen; halo; $C_{1-8}$ alkyl, alkenyl, or alkynyl optionally interrupted by oxygen or sulfur; cycloalkyl; alkoxy; arylalkoxy; or heteroarylalkoxy;
$R_5$, when present, represents independently for each occurrence hydrogen, halo, hydroxy, alkyl, alkenyl, cycloalkyl, alkoxy, —$CO_2H$, —$CO_2C_{1-3}$alkyl, cyano, aryl, heteroaryl, aralkyl, heteroaralkyl, oxo, —$CF_3$, —O—$CF_3$, —O—$CHF_2$, —O—$CH_2F$, —O-aryl, —N(H)alkyl, —N(H)$SO_2$-alkyl, —N(H)C(O)alkyl, —$SO_2$N(H)alkyl, —$SO_2$N(alkyl)C(O)alkyl, or —C(O)N(H)$SO_2$alkyl;
n is 0 or 1;
p is 1;

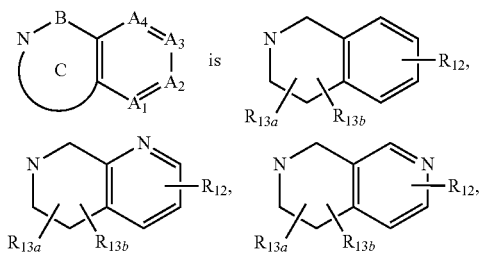

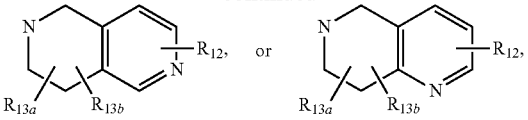

wherein $R_{12}$ is, independently for each occurrence, hydrogen, halo, alkyl, haloalkyl, haloalkoxy, alkoxy, or cyano; and
$R_{13a}$ and $R_{13b}$ are each independently hydrogen, halo, alkyl, haloalkyl, alkoxy, or haloalkoxy.

9. The compound of claim 1, which is a compound of formula I-A3:

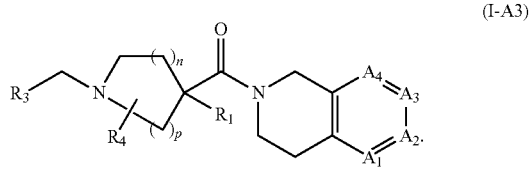

(I-A3)

10. The compound of claim 1, which is a compound of formula I-B1:

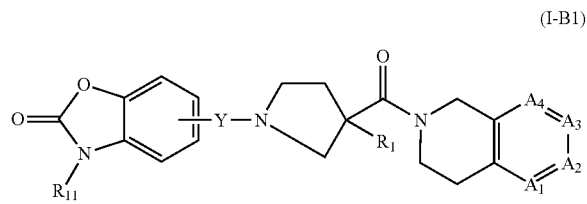

(I-B1)

or pharmaceutically acceptable salts thereof; and Y is $C_{1-4}$ alkylene.

11. The compound of claim 1, wherein $A_1$ is N or C—$R_5$; and $A_2$, $A_3$, and $A_4$ are C—$R_5$.

12. The compound of claim 1, which is:
5-((3-(cyclopropylmethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one;
5-((3-isobutyl-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 5-(1-(3-(methoxymethyl)-3-(3-(trifluoromethyl)-5,6,7,8-tetrahydro-1,6-naphthyridine-6-carbonyl)pyrrolidin-1-yl)ethyl)-3-methylbenzo[d]oxazol-2(3H)-one; 5-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; (R)-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; (S)-6-((3-(methoxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one;
3-ethyl-6-((3-(methoxymethyl)-3-(3-(trifluoromethyl)-5,6,7,8-tetrahydro-1,6-naphthyridine-6-carbonyl)pyrrolidin-1-yl)methyl)benzo[d]oxazol-2(3H)-one; 5-((3-(ethoxymethyl)-3-(3-(trifluoromethyl)-5,6,7,8-tetrahydro-1,6-naphthyridine-6-carbonyl)pyrrolidin-1- yl)methyl)-3-methylbenzo[d]oxazol-2(3H)-one; 5-((3-(methoxymethyl)-3-(7-(trifluoromethyl)-1,2,3,4-tetrahydroisoquinoline-2-carbonyl)pyrrolidin-1-yl)methyl)-3-methylbenzo[d]oxazol-2(3H)-one; 5-((3-isopropyl-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 2-(1-((3-methyl-2-oxo-2,3-dihydrobenzo[d]oxazol-5-yl)methyl)-3-(3-(trifluoromethyl)-5,6,7,8-tetrahydro-1,6-naphthyridine-6-carbonyl)pyrrolidin-3-yl)acetonitrile; 5-((3-(hydroxymethyl)-3-(3-(trifluoromethyl)-5,6,7,8-tetrahydro-1,6-naphthyridine-6-carbonyl)pyrrolidin-1-yl)methyl)-3-methylbenzo[d]oxazol-2(3H)-one; 6-((4-isobutyl-4-(3-(trifluoromethyl)-5,6,7,8-tetrahydro-1,6-naphthyridine-6-carbonyl)piperidin-1-yl)methyl)-3-methylbenzo[d]oxazol-2(3H)-one; 2-(3-(methoxymethyl)-1-((3-methyl-2-oxo-2,3-dihydrobenzo[d]oxazol-5-yl)methyl)pyrrolidine-3-carbonyl)-7-(trifluoromethyl)-1,2,3,4-tetrahydroisoquinoline-5-carbonitrile; 5-((3-(methoxymethyl)-3-(7-(trifluoromethyl)-1,2,3,4-tetrahydroisoquinoline-2-carbonyl)pyrrolidin-1-yl)methyl)-3-methylbenzo[d]oxazol-2(3H)-one; 6-(3-(methoxymethyl)-1-((3-methyl-2-oxo-2,3-dihydrobenzo[d]oxazol-5-yl)methyl)pyrrolidine-3-carbonyl)-5,6,7,8-tetrahydro-1,6-naphthyridine-3-carbonitrile; 5-((3-(methoxymethyl)-3-(1,2,3,4-tetrahydroisoquinoline-2-carbonyl)pyrrolidin-1-yl)methyl)-3-methylbenzo[d]oxazol-2(3H)-one; 5-(2-(3-(methoxymethyl)-3-(3-(trifluoromethyl)-5,6,7,8-tetrahydro-1,6-naphthyridine-6-carbonyl)pyrrolidin-1-yl)propan-2-yl)-3-methylbenzo[d]oxazol-2(3H)-one; 5-(1-(3-(methoxymethyl)-3-(3-(trifluoromethyl)-5,6,7,8-tetrahydro-1,6-naphthyridine-6-carbonyl)pyrrolidin-1-yl)cyclopropyl)-3-methylbenzo[d]oxazol-2(3H)-one; or a pharmaceutically acceptable salt thereof.

13. A pharmaceutical composition, comprising a compound of claim 1 and a pharmaceutically acceptable carrier.

14. A method of treating organ transplant rejection, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid, glomerulonephritides, vasculitides, hepatitis, allograft rejection, graft-versus-host disease, metabolic syndrome, or obesity, comprising administering to a patient in need thereof a therapeutically effective amount of a compound of claim 1.

15. A method of treating pain, comprising administering to a patient in need thereof a therapeutically effective amount of a compound of claim 1.

16. The compound of claim 1, wherein the compound is represented by

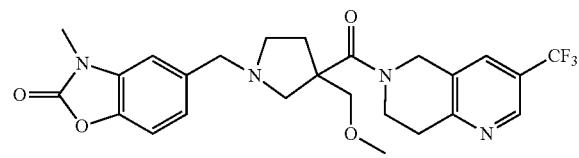 [SMILES: COCC1(C(=O)N2CCc3ncc(C(F)(F)F)cc3C2)CCN(Cc2ccc3oc(=O)n(C)c3c2)C1]

or a pharmaceutically acceptable salt thereof.

17. The compound of claim 1, wherein the compound is represented by

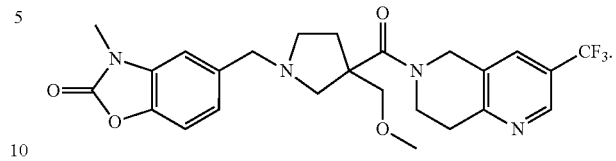

18. The compound of claim 1, wherein the compound is

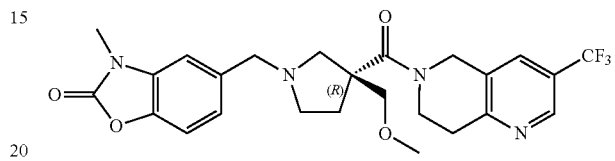

or a pharmaceutically acceptable salt thereof.

19. The compound of claim 1, wherein the compound is

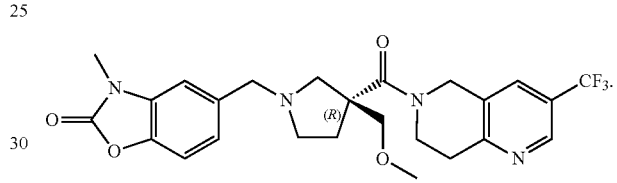

20. The compound of claim 1, wherein the compound is

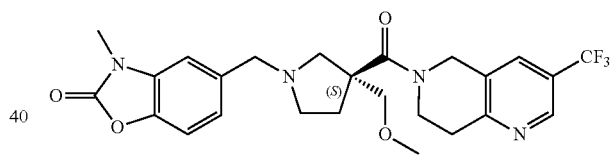

or a pharmaceutically acceptable salt thereof.

21. The compound of claim 1, wherein the compound is

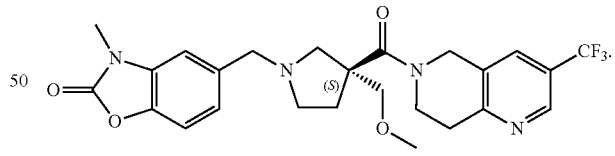

22. The compound of claim 1, wherein $R_1$ is alkoxyalkyl, and $R_{11}$ is hydrogen or alkyl.

23. The compound of claim 22, wherein Y is $C_{1-4}$ alkylene, and $R_4$ is hydrogen or $C_{1-8}$ alkyl, and $R_5$ represents independently for each occurrence hydrogen, halo, hydroxy, alkyl, alkoxy, or —$CF_3$.

24. The compound of claim 23, wherein n is 1.

25. The compound of claim 8, wherein $R_1$ is alkoxyalkyl, and $R_{11}$ is hydrogen or alkyl.

26. The compound of claim 25, wherein Y is $C_{1-4}$ alkylene, and $R_4$ is hydrogen or $C_{1-8}$ alkyl.

27. The compound of claim 26, wherein $R_5$ represents independently for each occurrence hydrogen, halo, hydroxy, alkyl, alkoxy, or —CF$_3$; R$_{12}$ is halo, alkyl, or haloalkyl; and R$_{13a}$ and R$_{13b}$ are each independently hydrogen, halo, alkyl, or haloalkyl.

28. The compound of claim 27, wherein

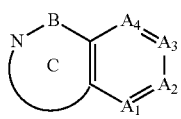 is 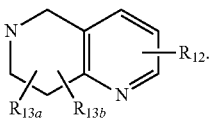

29. The compound of claim 27, wherein n is 1.

30. The compound of claim 9, wherein R$_1$ is alkoxyalkyl, and R$_{11}$ is hydrogen or alkyl.

31. The compound of claim 30, wherein R$_4$ is hydrogen or C$_{1-8}$ alkyl, and R$_5$ represents independently for each occurrence hydrogen, halo, hydroxy, alkyl, alkoxy, or —CF$_3$.

32. The compound of claim 31, wherein n is 1.

33. A pharmaceutical composition, comprising a compound of claim 8 and a pharmaceutically acceptable carrier.

34. A pharmaceutical composition, comprising a compound of claim 9 and a pharmaceutically acceptable carrier.

35. A pharmaceutical composition, comprising a compound of claim 28 and a pharmaceutically acceptable carrier.

* * * * *